US008697629B2

(12) United States Patent
Finlayson et al.

(10) Patent No.: US 8,697,629 B2
(45) Date of Patent: **\*Apr. 15, 2014**

(54) MODULATION OF INTRACELLULAR SIGNALING

(75) Inventors: Malcolm Finlayson, Solana Beach, CA (US); Bassam B. Damaj, San Diego, CA (US)

(73) Assignee: Angstrom Pharmaceuticals, Inc., Solana Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/041,198

(22) Filed: Mar. 4, 2011

(65) Prior Publication Data

US 2011/0217233 A1 Sep. 8, 2011

Related U.S. Application Data

(60) Provisional application No. 61/311,214, filed on Mar. 5, 2010.

(51) Int. Cl.
*A61K 38/00* (2006.01)
*C07K 7/06* (2006.01)

(52) U.S. Cl.
USPC ......... 514/1.1; 514/13.3; 514/18.9; 514/19.8; 514/21.6; 530/300; 530/328

(58) Field of Classification Search
None
See application file for complete search history.

(56) References Cited

U.S. PATENT DOCUMENTS

| | | | |
|---|---|---|---|
| 4,774,339 | A | 9/1988 | Haugland et al. |
| 5,187,288 | A | 2/1993 | Kang et al. |
| 5,248,782 | A | 9/1993 | Haugland et al. |
| 5,274,113 | A | 12/1993 | Kang et al. |
| 5,433,896 | A | 7/1995 | Kang et al. |
| 5,451,663 | A | 9/1995 | Kang et al. |
| 5,639,725 | A | 6/1997 | O'Reilly et al. |
| 5,863,540 | A | 1/1999 | Haynes et al. |
| 5,994,309 | A | 11/1999 | Mazar et al. |
| 6,432,405 | B1 | 8/2002 | Weinberg et al. |
| 6,696,416 | B1 | 2/2004 | Mazar et al. |
| 6,936,587 | B1 | 8/2005 | Mazar et al. |
| 6,963,587 | B2 | 11/2005 | Hannu et al. |
| 7,807,621 | B2 * | 10/2010 | Mazar et al. .................. 514/13.3 |
| 8,313,914 | B2 * | 11/2012 | Finlayson et al. ............. 435/7.1 |
| 2003/0223981 | A1 | 12/2003 | Mochly-Rosen et al. |
| 2004/0110933 | A1 | 6/2004 | Rondon et al. |
| 2005/0054593 | A1 | 3/2005 | Stromblad et al. |
| 2006/0228745 | A1 | 10/2006 | Mass |
| 2008/0194672 | A1 | 8/2008 | Hoveyda et al. |
| 2009/0143303 | A1 | 6/2009 | Mazar et al. |

FOREIGN PATENT DOCUMENTS

WO WO 2007/039761 4/2007

OTHER PUBLICATIONS

Piotrowicz et al Mol Cancer Ther 2011.*
Ahrens et al., "Soluble CD44 inhibits melanoma tumor growth by blocking cell surface CD44 binding to hyaluronic acid," *Oncogene* 20(26):3399-3408 (2001).
Aina et al., "eutic cancer targeting peptides," *Biopolymers* 66(3):184-199 (2002).
Albini et al., "A rapid in vitro assay for quantitating the invasive potential of tumor cells," *Cancer Res.* 47(12):3239-3245 (1987).
Allen et al., "The Cambridge Crystallographic Data Centre: Computer-Based Search, Retrieval, Analysis and Display of Information," *Acta Crystallogr.* B35:2331-2339 (1979).
Anderegg et al., "ADAM10 is the constitutive functional sheddase of CD44 in human melanoma cells," *J. Invest. Dermatol.* 129(6):1471-1482 (2009). (Epub Oct. 30, 2008).
Bazil and Horejsi, "Shedding of the CD44 adhesion molecule from leukocytes induced by anti-CD44 monoclonal antibody simulating the effect of a natural receptor ligand," *J. Immunol.* 149(3):747-753 (1992).
Bennett et al., "CD44 Isoforms Containing Exon V3 are Responsible for the Presentation of Heparin-binding Growth Factor," *J. Cell Biol.* 128(4):687-698 (1995).
Bertrand et al., "The BRET2/arrestin assay in stable recombinant cells: a platform screen for compounds that interact with G protein-coupled receptors (GPCRS)," *J. Recept. Signal Transduct. Res.* 22(1-4):533-541 (Feb.-Nov. 2002).
Blood and Zetter, "Tumor interactions with the vasculature: angiogenesis and tumor metastasis," *Biochim. Biophys. Acta.* 1032(1):89-118 (1990).
Borland et al., "Forms and functions of CD44," *Immunology* 93(2):139-148 (1998).
Bourguignon et al., "Hyaluronan-CD44 interaction stimulates Rac 1 signaling and PKNγ kinase activation leading to cytoskeleton function and cell migration in astrocytes," *J. Neurochem.* 101(4):1002-1017 (2007).
Bourguignon et al., "Hyaluronan-CD44 interaction with leukemia-associated RhoGEF and epidermal growth factor receptor promotes Rho/Ras co-activation, phospholipase CεCA2+ signaling, and cytoskeleton modification in head and neck squamous cell carcinoma cells," *J. Biol. Chem.* 281(20):14026-14040 (2006).
Bourguignon, "Hyaluronan-mediated CD44 activation of RhoGTPase signaling and cytoskeleton function promotes tumor progression," *Semin. Cancer Biol.* 18(4):251-259 (2008).
Bungaard, "Formation of Prodrugs of Amines, Amides, Ureides, and Imides," *Methods Enzymol.* 112:347-359 (1985).
Carlin et al., "Urokinase signal transduction and its role in cell migration," *FASEB J.* 19(2):195-202 (2005).

(Continued)

*Primary Examiner* — Cecilia J Tsang
*Assistant Examiner* — Li Lee
(74) *Attorney, Agent, or Firm* — Jones Day

(57) ABSTRACT

A method of treating a disease characterized by aberrant cell migration and/or invasion includes administering to a subject an effective amount of the peptide of SEQ ID NO:3, an Å6 polypeptide, or an isolated polypeptide consisting essentially of the Link region of human CD44 as indicated in FIG. 17 to modulate a FAK signal transduction pathway for a sufficient period of time to treat the disease. A method of diagnosing a condition characterized by aberrant cell migration and/or invasion includes measuring the effect of these polypeptides on FAK signal transduction activity; wherein a change in FAK signal transduction activity is indicative of said aberrant cell migration or invasion. A method of diagnosing a condition characterized by aberrant cell migration and/or invasion includes imaging FAK signal transduction activity in the presence of these polypeptides.

22 Claims, 23 Drawing Sheets

(56) References Cited

OTHER PUBLICATIONS

Casey et al., "CD44 and β1 integrins mediate ovarian carcinoma cell migration toward extracellular matrix proteins," *Clin. Exp. Metastasis* 18(1):67-75 (2000).

Chambers et al.,"The significance of urokinase-type plasminogen activator, its inhibitors, and its receptor in ascites of patients with epithelial ovarian cancer," *Cancer* 75(7):1627-1633 (1995).

Cheng et al., "A positive feedback loop couples Ras activation and CD44 alternative splicing," *Genes Dev.* 20(13):1715-1720 (2006).

Cichy et al., "Cytokines regulate the affinity of soluble CD44 for hyaluronan," *FEBS Lett.* 556(1-3):69-74 (2004).

Cichy et al., "The liberation of CD44," *J. Cell. Biol.* 161(5):839-843 (2003).

Crowley et al., "Prevention of metastasis by inhibition of the urokinase receptor," *Proc. Natl. Acad. Sci. U.S.A.* 90(11):5021-5025 (1993).

Endo et al., "The mechanism of action of ricin and related toxic lectins on eukaryotic ribosomes. The site and the characteristics of the modification in 28 S ribosomal RNA caused by the toxins," *J. Biol. Chem.* 262(12):5908-5912 (1987).

Frankel et al., "Prospects for immunotoxin therapy in cancer," *Ann. Rev. Med.* 37:125-142 (1986).

Frei III, E., "Clinical trials of antitumor agents: experimental design and timeline considerations," *Cancer J. Sc.i Am.* 3(3):127-136 (1997).

GenBank Accession: AAB13623; GI: 950416 (Aug. 13, 1996). [Retrieved from the Internet: Dec. 5, 2011: <http://www..ncbi.nlm.nih.gov/protein/950416>].

Gorelik et al., "Control of lung metastasis progression in mice: role of kinetics of 3LL Lewis lung carcinoma and host immune reactivity," *J. Natl. Cancer Inst.* 65(6):1257-1264 (1980).

Gorelik et al., "Host's immune state and kinetics of local tumor growth control—progression of postoperative lung metastasis," *Recent Results Cancer Res.* 75:20-28 (1980).

Guo et al., "A peptide derived from the nonreceptor binding region of urokinase plasminogen activator (uPA) inhibits tumor progression and angiogenesis and induces tumor cell death in vivo," *FASEB J.* 14(10):1400-1410 (2005).

Hefler et al., "Cytosol concentrations of CD44 isoforms in breast cancer tissue," *Int. J. Cancer (Pred. Oncol.)* 79(5):541-545 (1998).

Hilgard et al., "Oral anticoagulation in the treatment of a spontaneously metastasising murine tumour (3LL)," *Br. J. Cancer* 35(1):78-86 (1977).

Hoosein et al., "Involvement of urokinase and its receptor in the invasiveness of human prostatic carcinoma cell lines," *Cancer Commun.* 3(8):255-264 (1991).

Huang et al., "The microRNAs miR-373 and miR-520c promote tumour invasion and metastasis," *Nat. Cell. Biol.* 10(2):202-210 (2008).

Huse et al., "Generation of a large combinatorial library of the immunoglobulin repertoire in phage lambda," *Science* 246(4935):1275-1281 (1989).

International Preliminary Report on Patentability for International Application No. PCT/US2010/026428, dated Sep. 6, 2011.

International Preliminary Report on Patentability for International Application No. PCT/US2011/027125, dated Sep. 11, 2012.

International Search Report for International Application No. PCT/US2010/026428, Completion date of International Search, Sep. 2, 2010; date mailed, Nov. 19, 2010.

International Search Report for International Application No. PCT/US2011/027125, Completion date of International Search, Jun. 14, 2011; date mailed, Jun. 27, 2011.

Isakov et al., "An immune response against the alloantigens of the 3LL Lewis lung carcinoma prevents the growth of lung metastases, but not of local allografts," *Invasion Metastasis* 2(1):12-32 (1982).

Katagiri et al., "CD44 variants but not CD44s cooperate with betal-containing integrins to permit cells to bind to osteopontin independently of arginine-glycine-aspartic acid, thereby stimulating cell motility and chemotaxis," *Cancer Res.* 59(1):219-226 (1999).

Kohda et al., "Solution structure of the link module: a hyaluronan-binding domain involved in extracellular matrix stability and cell migration," *Cell* 86(5):767-775 (1996).

Lesley et al., "Binding of hyaluronic acid to lymphoid cell lines is inhibited by monoclonal antibodies against Pgp-1," *Exp. Cell. Res.* 187(2):224-233 (1990).

Lesley et al., "CD44 and its interaction with extracellular matrix," *Adv. Immunol.* 54:271-335 (1993).

Lesley et al., "Hyaluronan binding properties of a CD44 chimera containing the link module of TSG-6," *J. Biol. Chem.* 277(29):26600-26608 (2002).

Lesley et al., "Variant cell lines selected for alterations in the function of the hyaluronan receptor CD44 show differences in glycosylation," *J. Exp. Med.* 182(2):431-437 (1995).

Lessan et al., "CD44 and β1 integrin mediate ovarian carcinoma cell adhesion to peritoneal mesothelial cells," *Am. J. Pathol.* 154(5):1525-1537 (1999).

Li et al., "Beyond tumorigenesis: cancer stem cells in (2007). metastasis," *Cell. Res.* 17(1):3-14 (2007).

Li et al., "CD44-initiated cell spreading induces Pyk2 phosphorylation, is mediated by Src family kinases, and is negatively regulated by CD45," *J. Biol. Chem.* 276(31):28767-28773 (2001).

Liao et al., "Regulation of human CD44H and CD44E isoform binding to hyaluronan by phorbol myristate acetate and anti-CD44 monoclonal and polyclonal antibodies," *J. Immunol.* 151(11):6490-6499 (1993).

Lim et al., "Clinical application of functional glycoproteomics—dissection of glycotopes carried by soluble CD44 variants in sera of patients with cancers," *Proteomics* 8(16):3263-3273 (2008).

Lou et al., "Methylation of the CD44 metastasis suppressor gene in human prostate cancer," *Cancer Res.* 59(10):2329-2331 (1999).

Malavé et al., "Influence of inoculation site on development of the Lewis lung carcinoma and suppressor cell activity in syngeneic mice," *J. Natl. Cancer Inst.* 62(1):83-88 (1979).

Matsumura et al., "Significance of CD44 gene products for cancer diagnosis and disease evaluation," *Lancet* 340(8827):1053-1058 (1992).

Mayer et al., "De-novo expression of CD44 and survival in gastric cancer," *Lancet* 342(8878):1019-1022 (1993).

Merrifield, "Solid Phase Peptide Synthesis. I. The Synthesis of a Tetrapeptide," *J. Am. Chem. Soc.* 85:2149-2154 (1963).

Min et al., "Urokinase receptor antagonists inhibit angiogenesis and primary tumor growth in syngeneic mice," *Cancer Res.* 56(10):2428-2433 (1996).

Naor et al., "CD44: structure, function, and association with the malignant process," *Ad. Cancer Res.* 71:241-319 (1997).

Odedra and Weiss, "Low molecular weight angiogenesis factors," *Pharmacol. Ther.* 49(1-2):111-124 (1991).

Ohno et al., "Hyaluronan oligosaccharides induce matrix metalloproteinase 13 via transcriptional activation of NFκB and p38 MAP kinase in articular chondrocytes," *J. Biol. Chem.* 281(26):17952-17960 (2006).

Okamoto et al., "Proteolytic release of CD44 intracellular domain and its role in the CD44 signaling pathway," *J. Cell. Biol.* 155(5):755-762 (2001).

Olsnes et al., "Immunotoxins—entry into cells and mechanisms of action," *Immunol. Today* 10(9):291-295 (1989).

Parish et al., "A basement-membrane permeability assay which correlates with the metastatic potential of tumour cells," *Int. J. Cancer* 52(3):378-383 (1992).

Penfold et al., "The role of angiogenesis in the spread of oral squamous cell carcinoma," *Br. J. Oral Maxillofac Surg.* 34(1):37-41 (1996).

Peng et al., "CD44 crosslinking-mediated matrix metalloproteinase-9 relocation in breast tumor cells leads to enhanced metastasis," *Int. J. Oncol.* 31(5):1119-1126 (2007).

Peterson et al., "CD44 modulates Smad1 activation in the BMP-7 signaling pathway," *J. Cell. Biol.* 166(7):1081-1091 (2004).

Platt et al., "Anticancer Therapeutics: Targeting Macromolecules and Nanocarriers to Hyaluronan or CD44, a Hyaluronan Receptor," *Mol. Pharm.* 5(4):474-486 (2008).

Ponta et al., "CD44: From Adhesion Molecules to Signalling Regulators," *Nat. Rev. Mol. Cell. Biol.* 4(1):33-45 (2003).

(56) References Cited

OTHER PUBLICATIONS

Powell, "Chapter 30. Peptide Stability in Drug Development: in vitro Peptide Degradation in Plasma and Serum," *Annu. Rep. Med. Chem.* 28:285-294 (1993).

Rabbani et al.,"Prevention of prostate-cancer metastasis in vivo by a novel synthetic inhibitor of urokinase-type plasminogen activator (uPA)," *Int. J. Cancer* 63(6):840-845 (1995).

Ridley et al., "Cell migration: integrating signals from front to back," *Science* 302(5651):1704-1709 (2003).

Robbins et al., "MAP kinase pathways and calcitonin influence CD44 alternate isoform expression in prostate cancer cells," *BMC Cancer* 8:260 (2008).

Rusinko et al., "Using CONCORD to Construct a Large Database of Three-Dimensional Coordinates from Connection Tables," *J. Chem. Inf. Comput. Sci.* 29:251-255 (1989).

Sackstein et al., "Ex vivo glycan engineering of CD44 programs human multipotent mesenchymal stromal cell trafficking to bone," *Nat. Med.* 12(14):181-187 (2008).

Schnaper et al., "Plasminogen activators augment endothelial cell organization in vitro by two distinct pathways," *J. Cell. Physiol.* 165(1):107-118 (1995).

Sillanpää et al., "CD44 expression indicates favorable prognosis in epithelial ovarian cancer," *Clin. Cancer Res.* 9(14):5318-5324 (2003).

Spessotto et al., "Hyaluronan-CD44 interaction hampers migration of osteoclast-like cells by down-regulating MMP-9," *J. Cell. Biol.* 158(6):1133-1144 (2002).

Stirpe et al., "Ribosome-inactivating proteins up to date," *FEBS Lett.* 195(1-2):1-8 (1986).

Subramaniam et al., "CD44 regulates cell migration in human colon cancer cells via Lyn kinase and AKT phosphorylation," *Exp. Mol. Pathol.* 83(2):207-215 (2007).

Sugiura and Stock, "Studies in a tumor spectrum. III. The effect of phosphoramides on the growth of a variety of mouse and rat tumors," *Cancer Res.* 15(1):38-51 (1955).

Suzuki et al., "CD44 stimulation by fragmented hyaluronic acid induces upregulation and tyrosine phosphorylation of c-Met receptor protein in human chondrosarcoma cells," *Biochim. Biophys. Acta.* 1591(1-3):37-44 (2002).

Taher et al., "Signaling through CD44 is mediated by tyrosine kinases. Association with p56lck in T lymphocytes," *J. Biol. Chem.* 271(5):2863-2867 (1996).

Takeda et al., "Ligand-induced structural changes of the CD44 hyaluronan-binding domain revealed by NMR," *J. Biol. Chem.* 281(52):40089-40095 (2006).

Talmadge and Fidler, "Enhanced metastatic potential of tumor cells harvested from spontaneous metastases of heterogeneous murine tumors," *J. Natl. Cancer Inst.* 69(4):975-980 (1982).

Teriete et al., "Structure of the regulatory hyaluronan binding domain in the inflammatory leukocyte homing receptor CD44," *Mol Cell.* 13(4):483-496 (2004).

Terpe et al., "Expression of CD44 isoforms in renal cell tumors. Positive correlation to tumor differentiation," *Am. J. Pathol.* 148(2):453-463 (1996).

Thorne et al., "The role of the CD44 transmembrane and cytoplasmic domains in co-ordinating adhesive and signalling events," *J. Cell. Sci.* 117(Pt 3):373-380 (2004).

Underhill, "Interaction of hyaluronate with the surface of simian virus 40-transformed 3T3 cells: aggregation and binding studies," *J. Cell. Sci.* 56:177-189 (1982).

van der Voort et al., "Heparan sulfate-modified CD44 promotes hepatocyte growth factor/scatter factor-induced signal transduction through the receptor tyrosine kinase c-Met," *J. Biol. Chem.* 274(10):6499-6506 (1999).

Vigetti et al., "Hyaluronan-CD44-ERK1/2 regulate human aortic smooth muscle cell motility during aging," *J. Biol. Chem.* 283(7):4448-4458 (2008).

Vitetta et al., "Immunotoxins," *Annu. Rev. Immunol.* 3:197-212 (1985).

Written Opinion of the International Searching Authority for International Application No. PCT/US2010/026428, Completion date of this Opinion, Sep. 2, 2010; date mailed, Nov. 19, 2010.

Written Opinion of the International Searching Authority for International Application No. PCT/US2011/027125, Completion date of this Opinion, Jun. 14, 2011; date mailed Jun. 27, 2011.

Xing and Rabbini, "Overexpression of urokinase receptor in breast cancer cells results in increased tumor invasion, growth and metastasis," *Int. J. Cancer* 67(3):423-429 (1996).

Yokoyama and Ramakrishnan, "Improved biological activity of a mutant endostatin containing a single amino-acid substitution," *British Journal of Cancer* 90(8):1627-1635 (2004).

Yonemura et al., "Direct involvement of ezrin/radixin/moesin (ERM)-binding membrane proteins in the organization of microvilli in collaboration with activated ERM proteins," *J. Cell. Biol.* 145(7):1497-1509 (1999).

Yu et al., "Localization of matrix metalloproteinase 9 to the cell surface provides a mechanism for CD44-mediated tumor invasion," *Genes Dev.* 13(1):35-48 (1999).

Zheng et al., "Monoclonal antibodies to CD44 and their influence on hyaluronan recognition," *J. Cell. Biol.* 130(2):485-495 (1995).

Geran et al., "Protocols for Screening Chemical Agents and Natural Products Against Animal Tumors and Other Biological Systems (Third Edition)," *Cancer Chemoth. Reports* Pt 3, 3:1-112 (1972).

Hammerling et al., "Monoclonal Antibodies and T-Cell Hybridomas," *Elsevier*, pp. 563-587, New York, (1981).

Köhler and Milstein, "Continuous cultures of fused cells secreting antibody of predefined specificity," *Nature* 256(5517):495-497 (1975).

Moulds et al., "Immunology of Transfusion Medicine," *Marcel Dekker, Inc.*, pp. 273-297 New York, (1994).

Norderhaug et al., "Versatile vectors for transient and stable expression of recombinant antibody molecules in mammalian cells," *J. Immunol. Methods* 204(1):77-87 (1997).

Thakur et al., "Indium-111-labeled leukocytes for the localization of abscesses: preparation, analysis, tissue distribution, and comparison with gallium-67 citrate in dogs," *J. Lab. Clin. Med.* 89(1):217-228 (1977).

Ward et al., "Binding activities of a repertoire of single immunoglobulin variable domains secreted from *Escherichia coli*," *Nature* 341(6242):544-546 (1989).

\* cited by examiner

A6 – Binding Protein Amino Acid Sequence

CD44 Residues

| | 120 | 121 | 122 | 123 | 124 | 125 | 126 | 127 |
|---|---|---|---|---|---|---|---|---|
| CD44 | N | A | S | A | P | P | E | E |
| A6 | K | P | S | S | P | P | E | E |

MODULATION OF INTRACELLULAR SIGNALING

This application claims the benefit of priority of U.S. Provisional application Ser. No. 61/311,214, filed Mar. 5, 2010, the entire content of which is incorporated herein by reference.

BACKGROUND OF THE INVENTION

This invention relates generally to small molecules that modulate cell invasion and migration, more specifically to peptides that modulate cell invasion and migration by binding to CD44. CD44 is the main cell surface receptor for hyaluronate/hyaluronic acid (HA), as well as collagen and fibronectin. It plays a role in a diverse range of physiological and pathological processes, including cell-cell and cell-extracellular matrix interactions, cell migration, lymphocyte homing, leukocyte activation, hemopoiesis, presentation of chemokines and growth factors, and metastatic spread. CD44 is reported to have a fundamental role in promoting cell survival and the loss of CD44 expression is reported to be an important factor in the death program.

CD44 cell-surface receptor expresses multiple isoforms, some of which have been implicated in tumor growth and metastasis. The expression of metastatic CD44 variants can be found in human breast and colon tumors and can occur early during cancer progression.

Given the role of CD44 in cancer metastasis and other inflammatory processes, it would be beneficial to develop compounds that allow treatment, diagnosis and imaging of these conditions based on CD44 activation. The present invention satisfies these needs and provides related benefits as well.

SUMMARY OF THE INVENTION

In some aspects, embodiments disclosed herein relate to a method of treating a disease characterized by aberrant cell migration and/or invasion that includes administering to a subject an effective amount of the peptide of SEQ ID NO:3, an Å6 polypeptide, or an isolated polypeptide consisting essentially of the Link region of human CD44 as indicated in FIG. 17 to modulate a FAK signal transduction pathway for a sufficient period of time to treat the disease.

In some aspects, embodiments disclosed herein relate to a method of diagnosing a condition characterized by aberrant cell migration and/or invasion that includes measuring the effect of the peptide of SEQ ID NO:3, an Å6 polypeptide, or an isolated polypeptide consisting essentially of the Link region of human CD44 as indicated in FIG. 17 on FAK signal transduction activity; whereby the change is indicative of the aberrant cell migration or invasion.

In some aspects, embodiments disclosed herein relate to a method of diagnosing a condition characterized by aberrant cell migration and/or invasion that includes imaging the FAK signal transduction activity in the presence of the peptide of SEQ ID NO:3, an Å6 polypeptide, or an isolated polypeptide consisting essentially of the Link region of human CD44 as indicated in FIG. 17.

BRIEF DESCRIPTION OF THE DRAWINGS

FIG. 16 shows homology between Å6 (SEQ ID NO:1) and the peptide of SEQ ID NO:3 of the present invention.

DETAILED DESCRIPTION OF THE INVENTION

Figure 1:
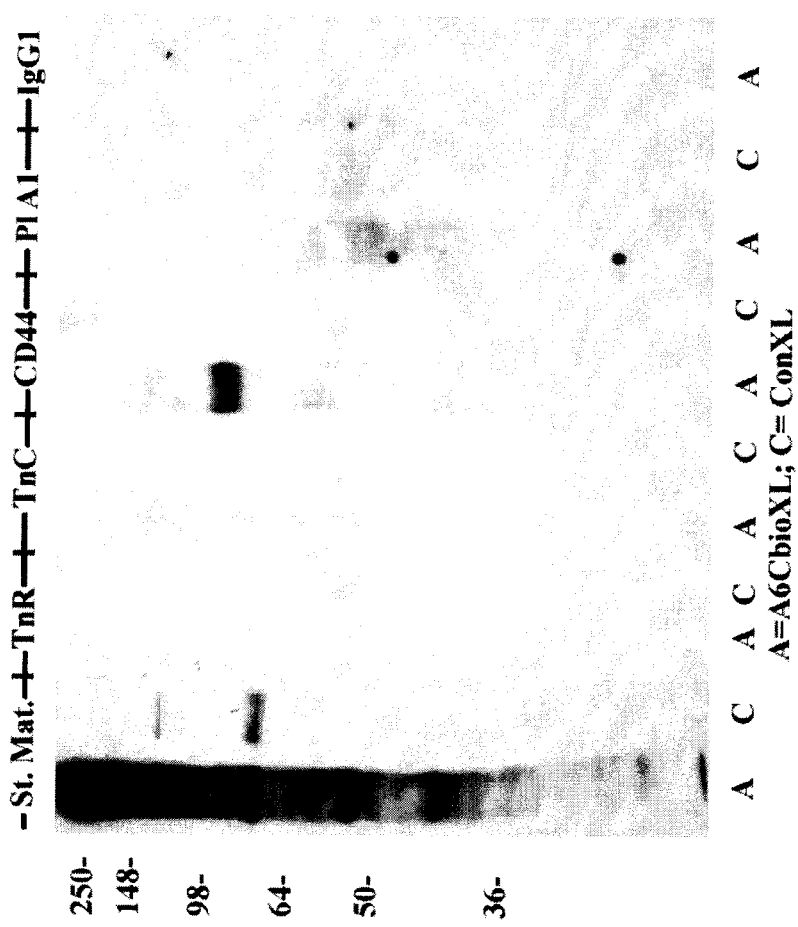
FIG. 1 shows immunoprecipitation of Å6CbioXL polypeptides using HRP-SA blotting.

The present disclosure is directed, in part, to peptides and their use in modulating cell migration and invasion. In one embodiment, the invention provides a peptide of SEQ ID NO:3=NASAPPEE and capped variants. The homologous peptide of SEQ ID NO:1=Ac-KPSSPPEE-Am=Å6, and related peptides (Å6 peptides) and peptidomimetics show the ability to inhibit chemotaxis. Embodiments disclosed herein relate to various treatment, diagnostic, imaging, and drug discovery methods based on the finding that SEQ ID NO:1 potentiates the binding of CD44 polypeptide expressing cells to hyaluronic acid (HA). In some embodiments, the present invention is also directed to the use of SEQ ID NO:3 and capped variants to potentiate the binding of CD44 to HA. Because of the involvement of CD44 in various signal transduction pathways related to cell motility it is a valuable target for the development of therapies for treating cancer, especially metastatic cancer, as well as a number of aberrant inflammatory processes such as arthritis, for example.

In still further embodiments, the present invention is directed to various complexes between Å6, Å6 peptides or peptidomimetics, or SEQ ID NO:3 or its capped variants with CD44 polypeptides. As demonstrated below in the Examples, the target of SEQ ID NO:1 is CD44. Furthermore, Example X below shows that upon binding of SEQ ID NO:1 to CD44, such complexes subsequently form CD44 clusters, including dimers and other higher molecular weight aggregates. The ability of SEQ ID NO:3 to inhibit migration in analogy with the Å6 peptides shown below in Example XIII.

As used herein, "CD44" or "CD4 polypeptide" refers to the wild-type CD44 or CD44 standard (CD44s) as well as splice variants, any of which can be biomarkers associated with tumor metastasis and/or cancer depending on the distribution and degree of expression. CD44 includes both membrane bound as well as "shed" soluble forms, sCD44, that are released extracellularly upon proteolysis of the membrane bound form. The term also encompasses various glycosylated derivatives of CD44s and CD44 variants. CD44 can also form intracellular cleavage products that distribute themselves in the cytosol. These cytosolic cleavage products can further stimulate transcription of CD44 polypeptides.

As used herein, a "condition characterized by aberrant cell migration and/or invasion" includes, without limitation, such processes as tumor metastasis, inflammatory processes and immune disorders. Conditions associated with aberrant cell migration and/or invasion also include vascular disease, mental retardation, fibrosis, and tumor formation.

As used herein, the term "binding" refers to the association of a compound with a target via non-covalent interactions including, for example, hydrogen bonding, salt bridges, van Der Waals attractive forces, and the like. In methods of the present invention, SEQ ID NO:1 and SEQ ID NO:3 or capped variants bind CD44 polypeptides.

As used herein, the term "Å6" or "Å6 polypeptide" is intended to mean a polypeptide having substantially the amino acid sequence Lys-Pro-Ser-Ser-Pro-Pro-Glu-Glu (also abbreviated in single letter amino acid code as KPSSPPEE, SEQ ID NO:2) or a substitution variant, addition variant, or chemical derivative thereof including peptidomimetics. An Å6 polypeptide is the subject matter of U.S. Pat. Nos. 5,994, 309; 6,696,416; and 6,963,587. An Å6 polypeptide of the invention exhibits one or more of the following activities: (a) at least about 20% of the biological activity of SEQ ID NO:1 or a capped variant as described below in one or more of the following in vitro bioassays: (i) invasion in a Matrigel® assay; (ii) endothelial tube formation on Matrigel®, or (iii) endothelial tube formation on a fibrin matrix in the presence of basic fibroblast growth factor and vascular endothelial growth factor; or (b) binding activity such that it competes with labeled SEQ ID NO:1 or a capped variant for binding to a cell or molecule which has a binding site for SEQ ID NO:1. A capped variant of an Å6 polypeptide of the invention refers to Å6 having chemical moieties at either or both of its amino or carboxyl termini. The moieties can include, for example, chemical groups such as acetyl (Ac) and amido (Am) groups.

A particularly useful capped Å6 polypeptide includes an acetyl group bound to the nitrogen at the amino-terminus and an amido group bound to the C-terminal carboxyl group. This capped polypeptide can be written as Ac-KPSSPPEE-Am. In specific embodiments, the invention also provides homologous Å6 polypeptide of SEQ ID NO:3.

The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids, and have an activity such as the selective homing activity of the peptide upon which the peptidomimetic is derived (see, for example, Goodman and Ro, *Peptidomimetics for Drug Design*, in "Burger's Medicinal Chemistry and Drug Discovery" Vol. 1 (ed. M. E. Wolff; John Wiley & Sons (1995), pages 803-861).

As used herein, the term "signal transduction pathway" refers to any process by which a cell converts one kind of signal or stimulus into another. A typical signal transduction involves an ordered sequence of biochemical reactions inside (and outside) the cell, which are carried out by enzymes, activated by second messengers, resulting in a signal transduction pathway. For example, CD44 is a transmembrane polypeptide that extracellularly binds hyaluronic acid (HA) which in turn can participate in a signal transduction pathway involving MAPK (ERK1/ERK2) or PI3K. Other signal transduction pathways include, without limitation, FAK, BMP-7, Src-family non-receptor protein tyrosine kinases (PTKs) such as Lck, Fyn, Lyn and Hck, calcium/calmodulin pathways, Ras, and Rho-family GTPases.

As used herein, "an effective amount" when used in connection with treating cancer is intended to qualify the amount of peptides used in the treatment of cancer and/or prophylaxis against cancer metastasis. This amount will achieve the goal of preventing, reducing, or eliminating cancer metastasis. An effective amount includes from about 1 mg/kg to about 1000 mg/kg in one embodiment and from about 5 mg/kg to about 500 mg/kg in another embodiment. When used in connection with treating inflammatory conditions, "an effective amount" is intended to qualify the amount of peptides used in the treatment of an inflammatory condition. This amount will achieve the goal of preventing, reducing, or eliminating inflammation. An effective amount includes from about 1 mg/kg to about 1000 mg/kg in one embodiment and from about 5 mg/kg to about 500 mg/kg in another embodiment.

The term "prodrug" refers to a compound that is made more active in vivo through metabolism of a precursor drug. Å6 polypeptides or the peptide of SEQ ID NO:3 or capped variants can exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the peptides described herein are structurally modified forms of the peptide that readily undergo chemical changes under physiological conditions to provide the active peptide. Additionally, prodrugs can be converted to the active peptide by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they can be easier to administer than the parent peptide. They may, for instance, be bioavailable by oral administration whereas the parent peptide is not. The prodrug can also have improved solubility in pharmaceutical compositions over the parent peptide. A wide variety of prodrug derivatives are known in the art, such as those that rely on hydrolytic cleavage or oxidative activation of the prodrug. An example, without limitation, of a prodrug would be a peptide which is administered as a C-terminal ester (the "prodrug"), but then is metabolically hydrolyzed to the C-terminal carboxylic acid, the active entity.

The term "therapeutically acceptable salt," as used herein, represents salts or zwitterionic forms of the peptides of the present invention which are water or oil-soluble or dispersible and therapeutically acceptable. The salts can be prepared during the final isolation and purification of the peptides or separately by adjusting the pH of the appropriate peptide formulation with a suitable acid or base.

As used herein, a "sufficient period" for treatment of cancer means a sufficient time pre- or post-operatively to reduce the chance of metastasis of cancer to other parts of the subject. Such an amount of time can be assessed, for example, by evaluating eradication and/or remission of the cancer. A "sufficient period" for the treatment of inflammation means a sufficient time such that the inflammatory process is reduced to a level the subject no longer suffers its debilitating effects. For a particular disorder, the frequency, dosage, and length of time can be determined in consultation with a physician.

In some embodiments, the present invention provides a peptide of SEQ ID NO:3, substitution and addition variants which maintain the ability to activate CD44. Measuring the ability to activate CD44 can be accomplished by the methods described below in the Examples, in particular Example X. Substitution variants include conservative substitutions as described further below. Addition variants include peptides having no more than 50 amino acids, in one embodiment, no more than 40 amino acids in another embodiment, or no more than 30, 20, 15, 14, 13, 12, 11, 10, or 9 amino acids in other embodiments, including all values in between.

Figure 17:
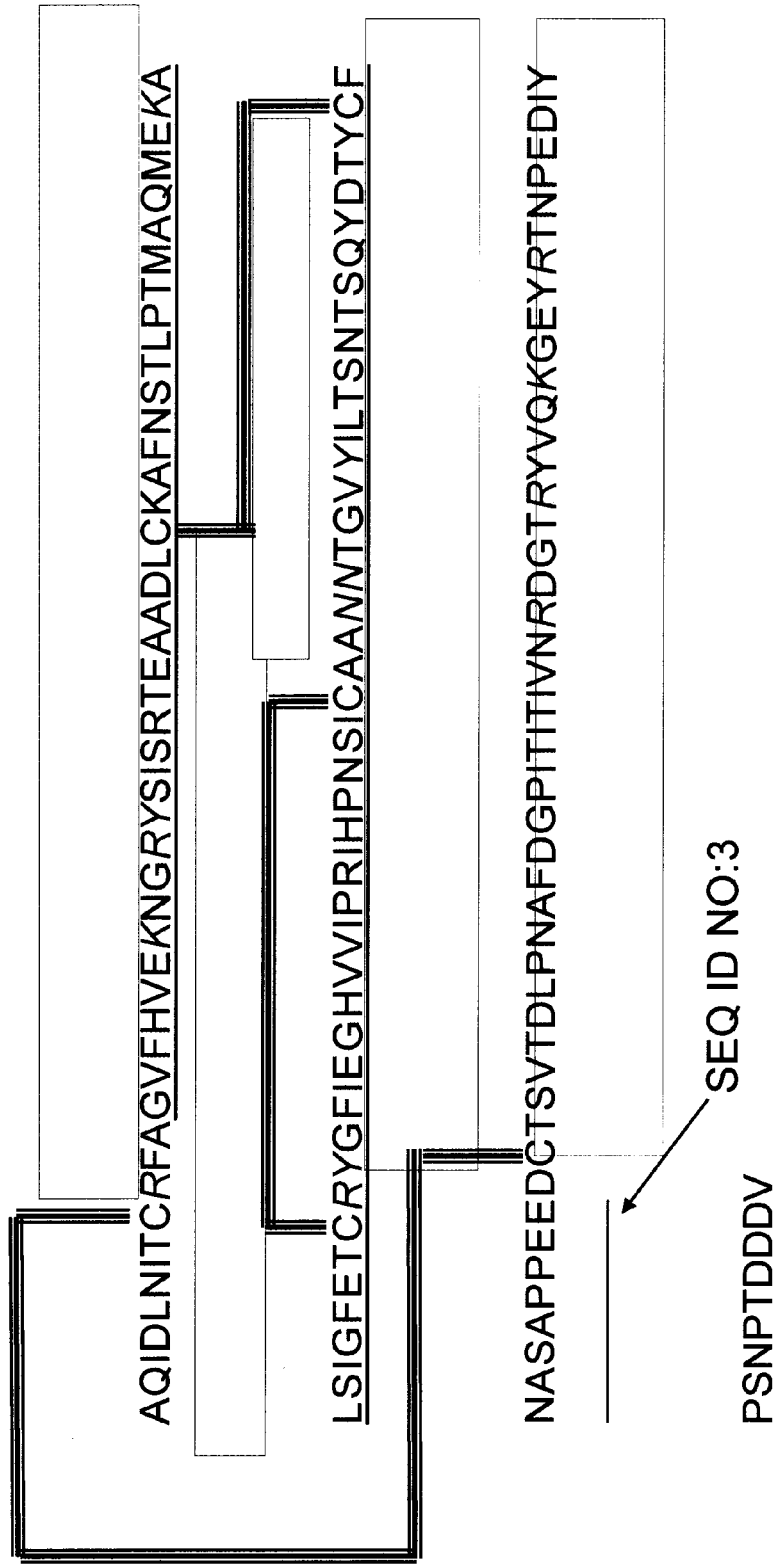
FIG. 17 shows the CD44 HA binding domain (SEQ ID NO:5). The CD44 Link module within the binding domain is indicated by the underlined amino acids.

In some embodiments, the present invention provides a peptide consisting essentially of sequence NASAPPEE (SEQ ID NO:3). The alignment of SEQ ID NO:3, corresponding to amino acids 120-127 of CD44, with SEQ ID NO: 1 is shown in FIG. 17. The high degree of homology between SEQ ID NO:1 and SEQ ID NO:3 indicates that such structures can exhibit analogous reactivity. Indeed, as shown in Example XIII below, SEQ ID NO:3 is capable of inhibiting migration of SKOV3 cells. Moreover, the presence of SEQ ID NO:3 within the context of a larger CD44 polypeptide indicates that this region of CD44 can serve as a site involved in CD44 aggregation and activation.

Modifications to SEQ ID NO:3 include capped variants in some embodiments. Like capped variants of the Å6 polypeptide, capped variants of SEQ ID NO:3 refers to the peptide having chemical moieties at either or both of its amino or carboxyl termini. The moieties can include, for example, chemical groups such as acetyl (Ac) and amido (Am) groups. In one embodiment, the capped peptide variant of SEQ ID NO:3 includes an acetyl group bound to the nitrogen at the amino-terminus and an amido group bound to the C-terminal carboxyl group. This capped polypeptide can be written as Ac-NASAPPEE-Am (SEQ ID NO:4). One skilled in the art will recognize that capping of a peptide can confer metabolic stability to the peptide.

The present invention also provides an Å6 polypeptide or SEQ ID NO:3 or capped variants as a complex bound to a CD44 polypeptide. The peptide-CD44 complex includes two CD44 polypeptides in some embodiments. In other embodiments, the peptide-CD44 complex includes more than two CD44 polypeptides, including trimers, tetramers, for example. In some embodiments, the peptide-CD44 complexes modulate binding of HA and thus, also modulate downstream cell signaling events.

The complex with CD44 polypeptide can be on the surface of a cell, in some embodiments. Such is the case for membrane bound CD44, for example. In other embodiments, the complex can occur with unbound CD44, such as soluble CD44 (sCD44). Any of the various complexes can be isolated in some embodiments.

In some embodiments, the present invention provides a method of treating a disease characterized by aberrant cell migration and/or invasion that includes administering to a subject an effective amount of the peptide of SEQ ID NO:1, addition variants thereof, substitution variants thereof, salts thereof, (collectively Å6 polypeptides) and combinations thereof, in a pharmaceutically acceptable vehicle, to bind a CD44 polypeptide to modulate a signal transduction pathway for a sufficient period of time to treat the disease.

In some embodiments, the present invention provides a method of treating a disease characterized by aberrant cell migration and/or invasion that includes administering to a subject an effective amount of the peptide of SEQ ID NO:3 and capped variants, in a pharmaceutically acceptable vehicle, to bind a CD44 polypeptide to modulate a signal transduction pathway for a sufficient period of time to treat the disease.

In some embodiments, treatment methods utilizing Å6 polypeptides or the peptide of SEQ ID NO:3 or capped variants are useful for inhibiting cell migration and invasion or migration-induced cell proliferation in a subject having a disease or condition associated with undesired cell migration, cell invasion, migration-induced proliferation, angiogenesis or metastasis. Cell migration processes include, for example, the locomotion of a cell from one point to another within the organism. Cell migration is well known in the art and generally involves cytoskeleton polymerization at the leading edge, local detachment from the ECM followed by movement, reattachment and depolymerization (Parsons et al., Science 302:1704-9, (2003)). Exemplary cell migration processes occur, for example, during normal development, throughout tissue growth and homeostasis and during aberrant proliferative conditions such as metastasis. For example, tissue formation during embryonic development, wound healing and immune responses all require the movement of cells in a particular direction to a specific location. Similarly, errors during this process can have deleterious consequences, including vascular disease, rheumatoid arthritis, tumor formation, metastasis and mental retardation.

Cell invasion processes include attachment and penetration of a cell into or through a tissue. Cell invasion can be related to cell migration because it involves cell locomotion. However, invasive processes can include a different profile of cell adhesion receptors and/or ECM polypeptides compared to cellular processes that are solely migratory. Cell invasion also can involve other cellular process such as proteolysis and matrix reorganization. An exemplary cell invasion process is the attachment to, proteolysis of penetration of a metastatic cell into or through a blood vessel or the basal lamina. Cellular locomotion into or through, for example, a blood vessel or basal lamina, can occur by cell migration. A variety of other cell invasion process also are well known in the art.

Cell metastasis is the transmission of neoplastic or cancerous cells from a primary site to one or more secondary sites elsewhere in the body resulting in a secondary cancerous growth. Transmission can occur, for example, by way of the blood vessels or lymphatics. Therefore, metastasis refers to the spread of cancer or other neoplastic cells from a primary to one or more secondary site and includes cell migration and invasion processes. The tumors produced by metastasis are responsible for 90% of the deaths caused by cancer.

Angiogenesis is the cellular process involving the growth of new blood vessels from pre-existing vessels. Angiogenesis is a normal process during growth and development, as well as in wound healing. However, angiogenesis also participates in the transition of tumors from a dormant state to a malignant state. Because tumors induce blood vessel growth, through growth factor secretion and induction of capillary growth into the tumor, angiogenesis supplies a tumor with the necessary nutrition for increased cellular growth. Angiogenesis also provides a means for single cancer cells to can break away from an established solid tumor, enter the blood vessel, and be transmitted to a distant secondary sites. An exemplary type of angiogenesis is sprouting angiogenesis which involves protease release by endothelial cells to degrade basement membrane, migration from the parent vessel walls and ultimately into a structure forming a vessel lumen.

Diseases or conditions that can be treated with Å6 polypeptides or the peptide of SEQ ID NO:3 or capped variants include primary growth or solid tumors or leukemias and lymphomas, metastasis, invasion and/or growth of tumor metastases, atherosclerosis, myocardial angiogenesis, post-balloon angioplasty vascular restenosis, neointima formation following vascular trauma, vascular graft restenosis, coronary collateral formation, deep venous thrombosis, ischemic limb angiogenesis, telangiectasia, pyogenic granuloma, corneal diseases, rubeosis, neovascular glaucoma, diabetic and other retinopathy, retrolental fibroplasia, diabetic neovascularization, macular degeneration, endometriosis, arthritis, fibrosis associated with chronic inflammatory conditions including psoriasis scleroderma, lung fibrosis, chemotherapy-induced fibrosis, wound healing with scarring and fibrosis; peptic ulcers, fractures, keloids, and disorders of vasculogenesis, hematopoiesis, ovulation, menstruation, pregnancy and placentation, or any other disease or condition in which invasion or angiogenesis is pathogenic.

A wide variety of different types of cancers can be treated with Å6 polypeptides or the peptide of SEQ ID NO:3 or capped variants, to inhibit the abnormal cell mobility processes. Categories of cancers that can be treated with Å6 polypeptides or the peptide of SEQ ID NO:3 or capped variants include carcinoma, sarcoma, leukemia, lymphoma, myeloma, and central nervous system cancers. Carcinoma refers to cancer that begins in the skin or in tissues that line or cover internal organs including adrenocortical carcinoma, basal cell carcinoma, lung carcinoma. Sarcoma refers to cancer that begins in bone, cartilage, fat, muscle, blood vessels, or other connective or supportive tissue including osteosarcoma, Ewing's sarcoma, malignant fibrous histiocytoma, and chondrosarcoma. Leukemia refers to cancer that starts in blood-forming tissue such as the bone marrow and causes large numbers of abnormal blood cells to be produced and enter the blood. Lymphoma and myeloma are cancers that begin in the cells of the immune system. Central nervous system cancers are cancers that begin in the tissues of the brain and spinal cord. Depending on the body part where a cancer is originated, different types of cancers include, for example, ovarian cancer, lung cancer, liver cancer, breast cancer, brain tumor, cervical cancer, colon cancer, prostate cancer, melanoma, pancreatic cancer, neuroblastoma, stomach cancer, or skin cancer. All the cancer patients, especially metastasis cancer patients, can benefit from treatment of an Å6 polypeptide or SEQ ID NO:3 or capped variants which exhibits anti-migration, anti-invasion, and anti-metastasis activities.

Without being bound by theory, an Å6 polypeptide or SEQ ID NO:3 or capped variants can induce conformational changes that can alter clustering, dimerization, oligomerization, lipid raft reorganization, and/or activation of CD44, as demonstrated in Example X below. As shown in the Examples below, the binding target of SEQ ID NO: 1 is CD44. Thus, complexes of the invention can subsequently form clusters of CD44 polypeptides, including dimers and oligomers which are induced by the binding of SEQ ID NO:1 or SEQ ID NO:3 or capped variants to the CD44 polypeptide. Such activation can be positive when followed by CD44 shedding since soluble CD44 (sCD44) activity can be anti-metastatic in some cancers. For example, it has been demonstrated that sCD44 inhibits melanoma tumor growth by blocking cell surface CD44 binding to HA (Ahrens et al., *Oncogene* 20:3399-3408 (2001)). Activation can also be positive in the absence of shedding when such activation blocks cell surface CD44 binding to HA.

As described above, Å6 polypeptides share a common motif found in CD44. The Å6 polypeptide having the structure Ac-KPSSPPEE-Am, SEQ ID NO:1 is related to SEQ ID NO:3, which appears as amino acids 120-127 in CD44 as shown in FIG. 17. Thus, CD44 polypeptides possesses a nested sequence with significant homology to Å6 and identical to the peptide of SEQ ID NO:3. One skilled in the art will recognize that acetyl-lysine of SEQ ID NO:1 shares structural similarities with asparagine (e.g., a carbonyl bonded to a primary or secondary amide) of SEQ ID NO:3 within the larger CD44 polypeptide. These amide moieties can impart similar conformational constraints and/or foster similar intra- or inter-molecular interactions. A similar structural feature is found in the peptide of SEQ ID NO:3 having an acetyl or similarly capped asparagine. The Å6-like sequence within CD44 polypeptides, which is identical to SEQ ID NO:3, straddles the splice junction of standard exons 3 and 4. Furthermore, the asparagine in SEQ ID NO:3 within CD44 is a potential site for N-linked glycosylation. This sequence in the CD44 polypeptide is proximal to the HA binding domain and there is a cysteine residue 2 residues N-terminal to the sequence that is involved in a disulfide bond. Because SEQ ID NO:1 is a binding ligand to CD44 and SEQ ID NO:1 shares this structural motif with SEQ ID NO:3, and SEQ ID NO: 3 is contained within CD44, these peptides can serve as a site of dimerization, for example, or other interaction that potentiates CD44 interaction with HA.

These dimerization events or interactions of CD44 and Å6 or SEQ ID NO:3 or capped variants can be modulated directly with Å6 or Å6 polypeptide agonists or SEQ ID NO:3 or capped variant agonists to treat conditions characterized by aberrant cell migration and invasion.

The CD44 polypeptide is a cell-surface glycoprotein involved in cell-cell interactions, cell adhesion and migration. It is a receptor for hyaluronic acid and can also interact with other ligands, such as osteopontin (Yohko et al., *Cancer Res.* 59:219-226 (1999)), collagens including as collagen 1, fibronectin, fibrin, laminin, and chondroitin sulfate (Naor et al., *Adv. Cancer Res.* 71:241-319 (1997)), growth factors including HB-EGF and b-FGF (Bennett et al., *J. Cell Biol.* 128:687-698 (1995)), matrix metalloproteinases (Yu et al., *Genes & Dev.* 13:35-48 (1999)) and cytokines (reviewed in Borland et al., *Immunology,* 93: 139-148 (1998), and Ponta et al., *Nature Rev. Mol. Cell Biol.* 4:33-45 (2003)). A specialized sialofucosylated glycoform of CD44 called HCELL is found natively on human hematopoietic stem cells, and is a highly potent E-selectin and L-selectin ligand. HCELL functions as a "bone homing receptor", directing migration of human hematopoietic stem cells and mesenchymal stem cells to bone marrow (Sackstein et al., *Nature Medicine* 14:181-187 (2008)).

CD44 participates in a wide variety of cellular functions including lymphocyte activation, recirculation and homing, hematopoiesis, and tumor metastasis. Transcripts for the CD44 gene undergo complex alternative splicing that results in many functionally distinct isoforms, however, the full length nature of some of these variants has not been determined. Alternative splicing is the basis for the structural and functional diversity of this polypeptide, and has been reported to be related to tumor metastasis as shown below. Splice variants of CD44 on colon cancer cells display the HCELL glycoform, which mediates binding to vascular E-selectin under hemodynamic flow conditions, a critical step in colon cancer metastasis. CD44 gene transcription is at least in part activated by beta catenin and Wnt signaling (also linked to tumor development).

Again, without being bound by theory, there are several mechanisms by which activation of CD44 can inhibit migration, including metastasis: 1) an Å6 polypeptide or a peptide of SEQ ID NO:3 or capped variant can cause prolonged activation/dimerization which can lead to desensitization of CD44 activity (for dimerization induced by Å6 see FIG. 13); 2) activation can induce shedding of soluble CD44; sCD44 has been shown to inhibit metastasis in some tumor cell lines as described above; and 3) CD44 activation with or without ligand binding can induce a secondary signal/intracellular association that can a) induce microfilament rearrangements that are inhibitory to migration (e.g. enhancement of cortical actin over stress fibers); b) modulate integrin activity; c) modulate migration-dependent signaling; and/or d) alter MMP expression, activity, and/or sequestering.

In some embodiments, an Å6 polypeptide or SEQ ID NO:3 or capped variant can cause prolonged activation-dimerization which can lead to desensitization of CD44 activity. Å6, SEQ ID NO:3 or capped variant binding to CD44 can reduce the efficiency of activation. Alternatively, Å6, SEQ ID NO:3 or capped variant binding to CD44 can reduce recycling. Å6, SEQ ID NO:3 or capped variant binding to CD44 can also uncouple the receptor's effector molecules, or may result in a down regulation of receptor expression.

In some embodiments, an Å6 polypeptide or SEQ ID NO:3 or a capped variant activates CD44 which in turn can induce shedding of soluble CD44 (sCD44). CD44 can undergo sequential proteolytic cleavage both extracellularly and intracellularly. The CD44 intracellular domain (ICD) fragment, CD44ICD, acts as a signal transduction molecule, where it translocates to the nucleus and activates transcription mediated through the 12-O-tetradecanoylphorbol 13-acetate-responsive element. Cells expressing CD44ICD produce high levels of CD44 messenger RNA, indicating that the CD44 gene is one of the potential targets for transcriptional activation by CD44ICD (Okamoto et al., *J. Cell Biol.* 155(5):755-762 (2001)).

Extracellular sCD44 has been shown to inhibit metastasis in some tumor cell lines. (For a general review see: Platt et al., *Mol. Pharm.* 4:474-86 (2008)). More specifically, it has been demonstrated that sCD44 can abolish the cell proliferation-promoting effect of HA on melanoma cell lines (Anderegg et al., *J Invest Dermatol.* e-pub ahead of print (2008)). In one embodiment, an Å6 polypeptide or SEQ ID NO:3 or a capped variant can enhance shedding via modulation of the protease ADAM10, an enzyme responsible for cleavage of membrane bound CD44 that generates sCD44 (Andergregg, supra). It has been further demonstrated that glycosylation patterns in sCD44 can serve as markers of malignancy and further indicates a role for glycosylation patterns in controlling shedding (Lim et al., *Proteomics* 16:3263-3273 (2008)). In some embodiments, an Å6 polypeptide or SEQ ID NO:3 or capped variant can modulate the shedding of sCD44 by modulating the interactions of the glycosylated portion of CD44 that are operative in the shedding process.

Various cytokine factors can regulate both the shedding of CD44, the subsequent interaction of sCD44 with HA and ultimately determine the impact of CD44 on physiologic and pathologic processes. For example, oncostatin M and transforming growth factor beta 1 (TGF-β1) are both capable of modulating the shedding of CD44 (Cichy et al., *FEBS Lett.* 556(1-3):69-74 (2004)). Thus, in some embodiments, an Å6 polypeptide or SEQ ID NO:3 or capped variant can enhance shedding via modulation of oncostatin M, while in other embodiments, an Å6 polypeptide or SEQ ID NO:3 or capped variant can enhance shedding via modulation of TGF-β1.

CD44 activation with or without ligand binding can induce a secondary signal/intracellular association that can (a) induce microfilament rearrangements that are inhibitory to migration for example by enhancement of cortical actin over stress fibers (Yonemura et al., *J. Cell Biol.* 145(7):1497-509 (1999)); (b) modulate integrin activity (Casey et al., *Clin. Exp. Med.* 18:67-75 (2000); Lesson et al., *Am. J. Path.* 154 (5):1525-1537 (1999)); (c) modulate migration-dependent signaling (Bourquiqnon, *Seminar Cancer Biol.* 8(4):251-9 (2008); Vitetti et al., *J. Biol. Chem.* 283(7):4448-58 (2008); Bourquiqnon, *J. Neurochem.* 101(4):1002-17 (2007); Thorne et al., *J. Cell Sci.* 117, 373-380 (2004)). For example, CD44 can act as a co-receptor for the ErbB family of receptor tyrosine kinases and for the c-Met receptor resulting in activation of receptor kinase activity and the regulation of diverse cellular processes, including cell survival, proliferation and differentiation, and/or (d) alter MMP expression, activity, and/or sequestering (Spessotto et. al., *J. Cell Biology* 158(6): 1133-1144 (2002); Peng et al., *Int. J. Oncol.* 31(5):1119-26 (2007); Ohno et. al., *J. Biol. Chem.* 281(26):17952-60 (2006)).

Because CD44 can function in a number of different settings to either promote or inhibit cell signaling and/or cellular functions, Å6 polypeptides or the peptide of SEQ ID NO:3 or capped variants can similarly promote or inhibit cellular functions to result in the inhibition of aberrant migration and invasion.

Thus, in some embodiments, an Å6 polypeptide or the peptide of SEQ ID NO:3 or capped variant can act as an agonist for CD44 activation. CD44 activation can trigger cell signaling events leading to inhibition of chemotaxis. In some embodiments, CD44 activation can turn off certain cell signaling events leading to inhibition of chemotaxis. In other embodiments, activated CD44 can modulate one or more signal transduction pathways to inhibit chemotaxis.

Alternatively, conformational changes associated with an Å6 polypeptide or SEQ ID NO:3 or capped variant binding to CD44 can alter CD44 binding to a native ligand, such as HA. In some embodiments, an Å6 polypeptide or SEQ ID NO:3 or capped variant can inhibit CD44 binding to HA, while in other embodiments, an Å6 polypeptide or SEQ ID NO:3 or capped variant can enhance CD44 binding to HA. For example, the peptides of the invention can enhance HA binding to sCD44 and/or inhibit binding of HA to cell surface CD44. Inhibition of cell surface CD44-HA binding can trigger cell signaling events leading to inhibition of chemotaxis. In other embodiments, inhibition of cell surface CD44-HA binding can turn off cell signaling events leading to inhibition of chemotaxis. In yet further embodiments, the inhibition of CD44-HA binding can modulate one or more signal transduction pathways to inhibit chemotaxis. Cell surface processing of CD44 is par of the migration process (Cichy et al., *J. Cell Biol.* 161:839-843 (2003)).

In some embodiments, enhancing CD44-HA binding can trigger cell signaling events leading to inhibition of chemotaxis. In other embodiments, enhancing CD44-HA binding can turn off cell signaling events leading to inhibition of chemotaxis. In yet further embodiments, the enhancing CD44-HA binding such as sCD44-HA binding, can modulate one or more signal transduction pathways to inhibit chemotaxis.

Alternatively, conformational changes associated with an Å6 polypeptide or SEQ ID NO:3 or capped variant binding to CD44 can alter CD44 interaction with other membrane bound proteins. In some embodiments, an Å6 polypeptide or SEQ ID NO:3 or capped variant can inhibit CD44 interaction with other membrane bound proteins, while in other embodiments, an Å6 polypeptide or SEQ ID NO:3 or capped variant can enhance CD44 interaction with other membrane bound proteins. Inhibition of CD44 interaction with other membrane bound proteins can trigger cell signaling events leading to inhibition of chemotaxis. In other embodiments, inhibition of CD44 interaction with other membrane bound proteins can turn off cell signaling events leading to inhibition of chemotaxis. In yet further embodiments, the inhibition of CD44 interaction with other membrane bound proteins can modulate one or more signal transduction pathways to inhibit chemotaxis.

In some embodiments, the present invention provides an isolated polypeptide having the Link region sequence of human CD44 as indicated by the underlined amino acids in FIG. 17, and functionally active fragments thereof which maintain the ability to bind to hyaluronic acid and/or activate CD44, including an isolated polypeptide consisting essentially of the Link region of human CD44 as indicated in FIG. 17. In some embodiments, the amino acids of the Link module can be substituted by conservative amino acid substitution as described herein. In still further embodiments, the isolated polypeptide can include addition variants, including up to 50 additional amino acids, including up to 40, 30, 20, 15, 14, 13, 12, 11, 10, 9, 8, 7, 6, 5, 4, 3, 2, and 1 additional amino acids, including all values in between. In still further embodiments, the present invention provides an isolated polypeptide consisting of the isolated hyaluronan-binding domain of CD44 as shown in FIG. 17.

CD44 has a hyaluronan-binding domain of about 160 amino acids, as shown in FIG. 17, and includes a single Link module, shown as underlined amino acids. The Link module is located extracellularly near the N-terminus of CD44 where it can interact with HA. Residues affecting HA binding, indicated in italics, have been identified through site directed mutagensis experiments. SEQ ID NO:3, homologous to Å6, appears as an extension off the Link module as shown in FIG. 17. Link modules are a superfamily of polypeptides that are ubiquitous in hyaluronan-binding proteins which include, for example, CD44, aggrecan, versican, neurocan, brevican, LYVE-1, TSG-6, KIA0527, CAB61358, and Stabilin-1. The CD44 Link module, in particular, is a domain of approximately 100 amino acids and includes four cysteines engaged in disulfide-bonds.

The three-dimensional structure of the Link module from human tumor necrosis factor-stimulated gene-6 (TSG-6) has been determined by nuclear magnetic resonance spectroscopy in solution (Kohda et al. Cell 86:767-775, (1996)). Link module alignments show a highly conserved sequence across the Link module superfamily, including the four cysteines residues. This has led to a 'consensus fold' for the Link module superfamily.

It has been demonstrated that a CD44 chimera which had its Link module replaced with that of failed to engage in rolling, which is characteristic of cellular migration processes (Lesley et al., J. Biol. Chem. 27:(29):26600-26608 (2002)). Furthermore, individual CD44 low avidity for HA plays a role in mediating the initial steps in cell migration. By contrast, the Link module of TSG-6 acts as a tether which is not compatible with leukocyte rolling. Thus, the rolling process associated with migration results from the reversible and multivalent nature of the CD44-HA interaction. TSG-6 has been indicated as a modulator of CD44-HA interactions.

Thus, in some embodiments, the present invention provides an isolated Link-polypeptide that includes the Link module of CD44. The isolated Link polypeptide can act as an inhibitor to HA binding to prevent rolling and subsequent extravasation, for example, associated with metastasis. In some embodiments, the present invention provides an isolated polypeptide consisting of the Link module of CD44. In some embodiments, the present invention provides an isolated Link polypeptide consisting essentially of the Link module of CD44. One skilled in the art will recognize that minor variations, including conservative amino acid substitutions in the Link module can be made while maintaining the ability to bind HA.

Furthermore, given the multivalent nature of the CD44-HA interaction in the biological context, the present invention also provides the Link polypeptide in multimeric form. Such multimeric displays of the Å6 polypeptide or SEQ ID NO:3 can function in a manner similar to the entire link module.

In some embodiments, enhancing CD44 interaction with other membrane bound proteins can trigger cell signaling events leading to inhibition of chemotaxis. In other embodiments, enhancing CD44 interaction with other membrane bound proteins can turn off cell signaling events leading to inhibition of chemotaxis. In yet further embodiments, enhancing CD44 interaction with other membrane bound proteins can modulate one or more signal transduction pathways to inhibit chemotaxis.

In yet still further embodiments, any combination of activation of CD44, inhibition or enhancement of ligand binding or interaction with other membrane bound proteins can modulate one or more signal transduction pathways to inhibit chemotaxis. In other embodiments, the binding of CD44 can be sufficient to treat the disease even in the absence of any effect on a particular signal transduction pathway.

The extracellular binding of CD44 with hyaluronic acid (HA), for example, can trigger a number of signal transduction pathways including, for example, MAPK (ERK1/ERK2), FAK, and PI3K. Other signal transduction pathways that CD44 can mediate include, without limitation, bone morphogenetic protein 7 (BMP-7), Src-family non-receptor protein tyrosine kinases (PTKs) such as Lck, Fyn, Lyn and Hck, calcium/calmodulin pathways, Ras, and Rho-family GTPases. Signal transduction pathways also include RTK, numerous GPCR pathways, including for example, G protein-coupled ion channel pathways and other ion channel pathways, intregrin pathways, such as those mediated via FAK, integrin-linked kinase (ILK), particularly interesting new cysteine-histidine rich protein (PINCH) and non-catalytic region of tyrosine kinase adaptor protein 2 (Nck2), and the Jak-STAT pathways mediated by various cytokines and growth factors. Thus, altering the binding of HA to CD44 in the presence of an Å6 polypeptide or SEQ ID NO:3 or capped variant can modulate any of these exemplary pathways.

Some cells can bind soluble HA such as murine NIH3T3 cells (Underhill, J. Cell Science 56:177 (1982)). However, many cells bind only immobilized HA (Lesley, Adv. Immun. 54:271-335 (1993)). SKOV3 used in the Examples below failed to bind FITC-HA but adhered to immobilized HA.

There are at least three states related to HA binding to CD44: 1) Non-active; 2) Inducible such as that associated with dimer formation, for example, by phorbol esters (Lesley et al., *Exp. Cell Research* 187:224-233 (1990); Liao et al., *J. Immun.* 151:6490-6499 (1993)); anti-CD44 crosslinking (Zheng et al., *J. Cell Bio.* 130: 485-495 (1995)); associated with deglycosylation, for example, inhibition of N-glycosylation/glycosidase treatment (Lesley et al., *J. Exp. Med.* 182: 431-437 (1995)); and 3) Constitutively Active. For example, CD44 binding to HA can be constitutively active depending on receptor number, glycosylation/deglycosylation and the ability to form dimers and other molecular associations. Although it is likely that SKOV3 CD44 does interact with soluble HA, it does so with an affinity and/or avidity that is too low for the association to be maintained and detected by the FACs assay presented in the Example below.

The adhesion assay allows the recruitment of CD44 molecules to bind multiple ligand molecules, allowing sufficient avidity for the interaction to be maintained and detected in the adhesion assay. This is similar to what is observed for the binding of adhesive glycoprotein (e.g., fibronectin, vitronectin) to integrin receptors. For other cell types, the CD44 receptor number, glycosylation state and ability to oligomerize can allow for sufficient avidity to allow the detection of soluble HA.

As shown in the Examples below, DF1485 (anti-CD44) immunoprecipitates an Å6Cbio-labeled polypeptide with the appropriate molecular weight. Furthermore, Å6 inhibits DF1485 anti-CD44 binding to SKOV3 cells. However, DF1485 does not blot Å6-crosslinked polypeptide and DF1485 does not bind Å6 in ELISA nor does DF1484 inhibit Rb anti-Å6-KLH in ELISA.

A variety of signaling pathways both upstream and downstream of CD44 can affect aberrant migration and invasion. It has been reported that MAP kinase pathways and calcitonin influence CD44 alternate isoform expression in prostate cancer (Robbins et al., *BMC Cancer* 8:260 (2008)). BMP-7 signal transduction occurs through the activation of intracellular Smad proteins. Smad1 was found to interact with the cytoplasmic domain of CD44. Pretreatment of chondrocytes with *Streptomyces* hyaluronidase inhibited BMP-7-mediated Smad1 phosphorylation, nuclear translocation of Smad1 or Smad4, and SBE4-luciferase reporter activation (Peterson et al., *J Cell Biol.* 166(7):1081-1091 (2004)). It has been indicated that signaling through CD44 is mediated by tyrosine kinases, in particular with p56$^{lck}$ in T lymphocytes (Taher et al., *J. Biol. Chem.* 271(5):2863-2867 (1996)). It has also been indicated that cancer associated splice variant CD44v3 possessing side-chain heparin sulfate (CD44-HS) promotes hepatocyte growth fact/scatter factor (HGF/SF)-induced signal transduction through the receptor tyrosine kinase c-Met (van der Voort et al., *J. Biol. Chem.* 274(10):6499-6506 (1999)). Furthermore, the overexpression of CD44-HS and c-Met were shown to be markers of tumor growth and metastasis. Alternative splice variant CD44v6 can serve as a coreceptor for growth factors that activate Ras (Cheng et al., *Genes Dev.* 20:1715-1720 (2006)). Cheng et al. identified a positive feedback loop in which Ras activation further promoted CD44v6 splicing.

In addition to ties to signaling pathways, variations in CD44 isoform expression have been shown to be markers of the cancer state. CD44 isoforms are reported as cell surface markers for some breast and prostate cancer stem cells, and has been implicated as an indicator of increased survival time in epithelial ovarian cancer patients. (Li et al., *Cell Research* 17:3-14 (2007); Sillanpää et al., *Clin Cancer Res.* 9(14):5318-24 (2003)) Splice variants of CD44 have been reported to be associated with metastases and have been reported to have potential in early detection (Matsumura et al., *Lancet* 340:1053-1058 (1992)). It was found that expression of CD44, which is not found in normal gastric mucosa and is found in only 49% of primary tumors, was associated with distant metastases at time of diagnosis and with tumor recurrence and increased mortality from gastric cancer. Serum CD44 is elevated in some patients with lymphoma (Mayer et al., *Lancet* 342:1019-1022 (1993)).

Several CD44 isoforms occur normally while others, termed CD44 variants (CD44v), are expressed in tumors. Isoforms CD44v7-10 were shown to be overexpressed in prostate cancer. Specific isoforms CD44v3-10 and CD44s exist in normal keratinocytes. Isoform CD44v3, however, has been identified in tumor tissue. CD44v5 and CD44v6 cytosol concentrations were found to be higher in breast cancer compared with fibroadenoma and normal breast tissue (Hefler et al., *Int. J. Cancer* 79(5):541-545 (1998)). An increase in expression of CD44s and several variant isoforms, including CD446v and CD449v, in the course of tumor differentiation in clear cell carcinomas has been observed (Terpe et al., *Am J. Pathol.* 148(2):453-463 (1996)). One skilled in the art will recognize that there are many other examples of aberrant expression of CD44s and CD44 variants, and various glycosylated forms thereof, that are associated with different tumor types, and that expression levels can vary according to the cancer type and stage of progression.

Human miR373 and miR520C stimulated cell migration and invasion in vitro and in vivo (Huang et al., *Nature Cell Biol.* 10:202-210 (2008)). Using expression array analysis, Huang et al. found that the migration phenotype of miR373- and miR520C-expressing cells depended on suppression of CD44. Upregulation of miR373 correlated inversely with CD44 expression in breast cancer metastasis samples. It was also noted that increased expression of the most common CD44 isoform correlates with overall survival of breast cancer patients. Similarly, it has been demonstrated that CD44 is a metastasis suppressor in human prostate cancer (Lou et al., *Cancer Res.* 59:2329-2331 (1999)). Studies of ligand-induced changes in CD44 determined by NMR provided a rationale for why proteolysis of the extracellular domain of CD44 can lead to enhanced tumor cell migration and invasion (Takeda et al., *J. Biol. Chem.* 281(52):40089-40095 (2006)).

Other conditions associated with aberrant migration and invasion include various inflammatory responses. Joint fluid from patients with inflammatory synovitis has higher than normal levels of soluble CD44 (Moulds et al., *Immunology of Transfusion Medicine*, New York, 273-297 (1994)).

Any of the foregoing CD44 polypeptides can be targeted by an Å6 polypeptide or SEQ ID NO:3 or capped variant to treat a condition characterized by aberrant migration and invasion. Such treatments can be monitored by a qualified physician, for example, to determine a treatment regimen regarding both dosage and determination of a sufficient period of time to treat the disease.

In an in vitro context, the effect of an Å6 polypeptide or SEQ ID NO:3 or capped variant on signaling events can be assessed by use of commercially available kits using a tissue sample. For example, a large array of kinase assay kits can be found on the worldwide web at biocompare.com/ProductCategories/1397/Kinase-Assays-Kits.html?sap=true. In some embodiments, the effect of modulating one or more of these signal transduction pathways via binding an Å6 polypeptide or SEQ ID NO:3 or capped variant to CD44 is the inhibition of cellular invasion and migration in a subject. Furthermore, assessing the signaling effects associated with an Å6 polypeptide or SEQ ID NO:3 or capped variant allows for the development of a multi-prong therapeutic approach through use of inhibitors of one or more signal transduction pathways.

In some embodiments the route of administration of an Å6 polypeptide or SEQ ID NO:3 or capped variant is systemic, although the pharmaceutical composition can also be administered topically or transdermally, e.g., as an ointment, cream or gel; orally; rectally; e.g., as a suppository, parenterally, by injection or continuously by infusion; intravaginally; intranasally; intrabronchially; intracranially intra-aurally; or intraocularly.

For topical application, the compound may be incorporated into topically applied vehicles such as a salve or ointment. The carrier for the active ingredient may be either in sprayable or nonsprayable form. Non-sprayable forms can be semi-solid or solid forms comprising a carrier indigenous to topical application and having a dynamic viscosity greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. In some embodiments, vehicles for nonsprayable topical preparations include ointment bases, e.g., polyethylene glycol-1000 (PEG-1000); conventional creams such as HEB cream; gels; as well as petroleum jelly and the like.

Also suitable for topic application are sprayable aerosol preparations wherein the compound, optionally in combination with a solid or liquid inert carrier material, is packaged in a squeeze bottle or in admixture with a pressurized volatile, normally gaseous propellant. The aerosol preparations can contain solvents, buffers, surfactants, perfumes, and/or antioxidants in addition to the compounds of the invention.

For the topical applications, especially for humans, one can administer an effective amount of the compound to an infected area, e.g., skin surface, mucous membrane, eyes, etc. This amount will generally range from about 0.001 mg to about 1 g per application, depending upon the area to be treated, the severity of the symptoms, and the nature of the topical vehicle employed.

In some embodiments an effective amount of an Å6 polypeptide or SEQ ID NO:3 or capped variant is used in the treatment of cancer and/or prophylaxis against cancer metastasis. This amount will achieve the goal of preventing, reducing, or eliminating cancer metastasis. An effective amount includes from about 1 mg/kg to about 1,000 mg/kg in one embodiment and from about 5 mg/kg to about 500 mg/kg in another embodiment. An effective amount can also be between about 10 mg/kg to about 250 mg/kg in yet another embodiment. An effective amount can be determined by a physician and can include such variables as age, weight, sex, and previous medical history of the subject. One skilled in the art will recognize that any amount between 1 mg/kg to about 1000 mg/kg can be administered including, without limitation, about 1, 2, 3, 4, 5, 6, 7, 8, 9, 10, 15, 20, 25, 30, 35, 40, 45, 50, 60, 70, 80, 90, 100, 120, 140, 150, 200, 250, 300, 350, 400, 450, 500, 550, 600, 650, 700, 750, 800, 850, 900, 950, and 1,000 mg/kg and any amount in between including fractions of a 1 mg/kg.

In some embodiments an effective amount of an Å6 polypeptide or SEQ ID NO:3 or capped variant is used in the treatment of an inflammatory condition. This amount will achieve the goal of preventing, reducing, or eliminating inflammation. An effective amount includes from about 1 mg/kg to about 1000 mg/kg in one embodiment and from about 5 mg/kg to about 500 mg/kg in another embodiment. An effective amount can also be between about 10 mg/kg to about 250 mg/kg in yet another embodiment. An effective amount can be determined by a physician and can include such variables as age, weight, sex, and previous medical history of the subject. One skilled in the art will recognize that any amount between 1 mg/kg to about 1000 mg/kg can be administered including, without limitation, about 1, 2, 3, 4, 5, 6, 7, 8, 9, 10, 15, 20, 25, 30, 35, 40, 45, 50, 60, 70, 80, 90, 100, 120, 140, 150, 200, 250, 300, 350, 400, 450, 500, 550, 600, 650, 700, 750, 800, 850, 900, 950, and 1,000 mg/kg and any amount in between including fractions of a 1 mg/kg.

Doses of the Å6 polypeptides or the peptide of SEQ ID NO:3 or capped variants include pharmaceutical dosage units comprising an effective amount of the peptide. An effective amount is meant an amount sufficient to achieve a steady state concentration in vivo which results in a measurable reduction in any relevant parameter of disease and may include growth of primary or metastatic tumor, any accepted index of inflammatory reactivity, or a measurable prolongation of disease-free interval or of survival. For example, a reduction in tumor growth in 20% of patients is considered efficacious (Frei III, E., *The Cancer Journal* 3:127-136 (1997)). However, an effect of this magnitude is not considered to be a minimal requirement for the dose to be effective in accordance with this invention.

In some embodiments, an effective dose is at least equal to, 10-fold and 100-fold higher than the 50% inhibitory concentration ($IC_{50}$) of the compound in an in vivo assay. The amount of active compound to be administered depends on the precise peptide or derivative selected, the disease or condition, the route of administration, the health and weight of the recipient, the existence of other concurrent treatment, if any, the frequency of treatment, the nature of the effect desired, for example, inhibition of tumor metastasis, and the judgment of the skilled practitioner. An exemplary dose for treating a subject, including a mammalian subject, such as a human, with a tumor is an amount of up to about 1,000 milligrams of active compound per kilogram of body weight or any of the amounts detailed above.

Typical single dosages of the peptide are between about 1 µg and about 1,000 mg/kg body weight. For topical administration, dosages in the range of about 0.01-20% concentration of the compound in one embodiment, and from 1-5%, in other embodiments. A total daily dosage in the range of about 10 milligrams to about 7 grams is possible for oral administration. The foregoing ranges are only suggestive, as the number of variables in regard to an individual treatment regime is large, and considerable excursions from these recommended values are expected. An effective amount or dose of the peptide for inhibiting invasion in vitro is in the range of about 1 picogram to about 0.5 nanograms per cell. Effective doses and dose ranges can be determined in vitro using the methods described herein.

Treatment methods can further utilize one or more additional compounds that are anti-tumor agents, such as mitotic inhibitors, e.g., vinblastine; alkylating agents, e.g., cyclophosphamide; folate inhibitors, e.g., methotrexate, piritrexim or trimetrexate; antimetabolites, e.g., 5-fluorouracil and cytosine arabinoside; intercalating antibiotics, e.g., adriamycin and bleomycin; enzymes or enzyme inhibitors, e.g., asparaginase; topoisomerase inhibitors, e.g., etoposide; or biological response modifiers, e.g., interferon. In fact, pharmaceutical compositions comprising any known cancer therapeutic in combination with the peptides disclosed herein are within the scope of this invention.

The formulations having an Å6 polypeptide or SEQ ID NO:3 or capped variant can also include one or more other medicaments, preferably anti-infectives such as antibacterial, anti-fungal, anti-parasitic, anti-viral, and anti-coccidial agents. Exemplary antibacterial agents include, for example, sulfonamides such as sulfamethoxazole, sulfadiazine or sulfadoxine; DHFR inhibitors such as trimethoprim, bromodiaprim or trimetrexate; penicillins; cephalosporins; aminoglycosides; bacteriostatic inhibitors of protein synthesis; the quinolonecarboxylic acids and their fused isothiazole analogs; and the like.

In another embodiment, the Å6 polypeptide or SEQ ID NO:3 or capped variant is therapeutically conjugated and used to deliver a therapeutic agent to the site of where the compounds home and bind, such as sites of tumor metastasis or foci of infection/inflammation. Therapeutically conjugated means that the Å6 polypeptide or SEQ ID NO:3 or capped variant is conjugated to a therapeutic agent. The therapeutic agents used in this manner act are directed either to the underlying cause or the components of the processes of tumor invasion, angiogenesis or inflammation. Examples of agents used to treat inflammation are the steroidal and non-steroidal anti-inflammatory drugs, many of which inhibit prostaglandin synthesis.

Other therapeutic agents which can be coupled to the compounds according to the methods of the invention are drugs, radioisotopes, lectins and other toxins. The therapeutic dosage administered is an amount which is therapeutically effective, and will be known to one of skill in the art. The dose is also dependent upon the age, health, and weight of the recipient, kind of concurrent treatment, if any, frequency of treatment, and the nature of the effect desired, such as, for example, anti-inflammatory effects or anti-bacterial effect.

Lectins are polypeptides, commonly derived from plants, that bind to carbohydrates. Among other activities, some lectins are toxic. Some of the most cytotoxic substances known are polypeptide toxins of bacterial and plant origin (Frankel et al., *Ann. Rev. Med.* 37:125-142 (1986)). These molecules binding the cell surface and inhibition cellular protein synthesis. The most commonly used plant toxins are ricin and abrin; the most commonly used bacterial toxins are diphtheria toxin and *Pseudomonas* exotoxin A. In ricin and abrin, the binding and toxic functions are contained in two separate protein subunits, the A and B chains. The ricin B chain binds to the cell surface carbohydrates and promotes the uptake of the A chain into the cell. Once inside the cell, the ricin A chain inhibits protein synthesis by inactivating the 60S subunit of the eukaryotic ribosome (Endo et al., *J. Biol. Chem.* 262:5908-5912 (1987)). Other plant derived toxins, which are single chain ribosomal inhibitory proteins, include pokeweed antiviral protein, wheat germ protein, gelonin, dianthins, momorcharins, trichosanthin, and many others (Strip et al., *FEBS Lett.* 195:1-8 (1986)). Diphtheria toxin and *Pseudomonas* exotoxin A are also single chain proteins, and their binding and toxicity functions reside in separate domains of the same protein chain with full toxin activity requiring proteolytic cleavage between the two domains. *Pseudomonas* exotoxin A has the same catalytic activity as diphtheria toxin. Ricin has been used therapeutically by binding its toxic α-chain, to targeting molecules such as antibodies to enable site-specific delivery of the toxic effect. Bacterial toxins have also been used as anti-tumor conjugates. As intended herein, a toxic peptide chain or domain is bound to a compound of this invention and delivered in a site-specific manner to a target site where the toxic activity is desired, such as a metastatic focus. Conjugation of toxins to such as antibodies or other ligands are known in the art (Olsnes et al, *Immunol. Today* 10:291-295 (1989); Vitetta et al., *Ann. Rev. Immunol.* 3:197-212 (1985)).

Examples of therapeutic radioisotopes which can be bound to the compound for use in accordance with according the methods of the invention, are 125 I, 131 I, 90Y, 67 Cu, 217 Bi, 211 At, 212 Pb, 47 Sc, and 109 Pd.

Cytotoxic drugs that interfere with critical cellular processes including DNA, RNA, and protein synthesis, have been conjugated to antibodies and subsequently used for in vivo therapy. Such drugs, including but are not limited to daunorubicin, doxorubicin, methotrexate, and Mitomycin C are also coupled to the compounds of this invention and use therapeutically in this form.

The Å6 polypeptides or the peptide of SEQ ID NO:3 or capped variants used in the methods of the invention may be further characterized as producing an inhibitory effect on cell migration and invasion, on angiogenesis, on tumor metastasis or on inflammatory reactions. The compounds are especially useful in producing an anti-tumor effect in a mammalian host, including humans, harboring a tumor.

Assays for assessing cell migration and invasion are well-known in the art and include the Boyden chamber assay discussed herein below. Other useful methods include those found in "Metastasis Research Protocols: Volume II: Analysis of Cell Behavior In Vitro and In Vivo," Methods in Molecular Medicine, Vol. 58, (2001).

The invention also provides a method of diagnosing a condition characterized by aberrant cell migration and/or invasion that includes determining the effects of binding of an Å6 polypeptide or SEQ ID NO:3 or capped variant on signal transduction activity. By determining a signal transduction activity one can diagnose the aberrant condition. For example, binding of an Å6 polypeptide or SEQ ID NO:3 or capped variant to a CD44 and subsequent determination of a signal linked to c-Met is a diagnostic marker of a metastatic state as described above. In practice, an Å6 polypeptide or SEQ ID NO:3 or capped variant can be added to a cell culture and a variety of assay kits can be used to determine its effect on signal transduction events.

In some embodiments, metastatic cancer is characterized by CD44 expression, including whether it is a membrane bound isoform or a shed form, and activation a signal transduction pathway. In such a case, an Å6- or SEQ ID NO:3 or capped variant-antagonist that binds CD44, for example, can be used to turn off this pathway. In diagnosis, an Å6- or SEQ ID NO:3 or capped variant-antagonist can be used to measure a turning off of a pathway to diagnose the metastatic condition. Thus, an in vitro measurement of inactivation of a pathway upon addition of an Å6- or SEQ ID NO:3 or capped variant-antagonist can also be used as a diagnostic of metastatic cancer.

In other embodiments, metastatic cancer is characterized by CD44, membrane bound or shed, causing a particular signal transduction pathway to be inactive. In such a case, an Å6 polypeptide or SEQ ID NO:3 or capped variant that binds CD44, for example, can be used to turn on this pathway. In diagnosis, such compounds can be used to measure a turning on of the pathway to diagnose the metastatic condition. Thus, an in vitro measurement of activation of such a pathway upon addition of an Å6 polypeptide or SEQ ID NO:3 or capped variant would indicate metastatic cancer. Hence, an Å6 polypeptide or SEQ ID NO:3 or capped variant can be used to treat or diagnose aberrant migration, including metastasis in many or all cancers.

The invention provides a method of diagnosing a condition characterized by aberrant cell migration and/or invasion that includes measuring the activity of an Å6 binding polypeptide or SEQ ID NO:3 or capped variant via a signal transduction pathway. In methods involving CD44 polypeptides, signal transduction pathways can include a MAPK pathway, for example. Thus, such diagnostic methods utilize downstream signals in the MAPK pathway to indicate CD44 modulation. Other pathways that involve CD44 include, for example, the PI3K pathway, BMP-7, Src-family non-receptor protein tyrosine kinases (PTKs) such as Lck, Fyn, Lyn and Hck, calcium/calmodulin pathways, Ras, and Rho-family GTPases.

The invention also provides a method of increasing the effectiveness of Å6 or SEQ ID NO:3 or capped variant therapeutic treatment by first determining the absence or presence of or measuring the a change in the amount or activity of Å6 therapeutic indicators in a subject or subpopulation of subjects suffering from a disease or condition mediated by uncontrolled cell mobility and then administering an Å6 polypeptide or SEQ ID NO:3 or capped variant to the subject or subpopulation of subjects, whose response to Å6 or SEQ ID NO:3 or capped variant therapeutic treatment differs from the response (to the same treatment) of a second subject or subpopulation of subjects suffering from the same disease or condition.

A population constitutes a plurality of two or more members. Populations can range in size from small, medium, to large. The size of small populations can range, for example, from a few members to tens of members. Medium populations can range, for example, from tens of members to about 100 members or hundreds of members. Large populations can range, for example, from hundreds of members to thousands, millions, and even greater number of member. The term "subpopulation" is intended to mean a subgroup that is part of a referenced population. Accordingly, the definition of the term "population" is intended to include all integer values greater than one. A subpopulation of the referenced population will contain at least one member less than the referenced population, for example, the subpopulation is at least 10%, 20%, 30%, 35%, 40%, 45%, 50%, 55%, 60%, 65%, 70%, 75%, 80%, 85% of the population, or any percentage in between.

Å6 therapeutic indicators include any of the variety of CD44 isoforms as disclosed herein that bind an Å6 polypeptide or SEQ ID NO:3 or capped variant, especially those isoforms that indicate a disease or disorder associated with aberrant cell migration or invasion. Å6 therapeutic indicators further include any signal transduction molecules within, for example, a particular CD44 isoform signal transduction pathway. For example, an increase in the activity of a CD44 isoform or a change in the signal transduction state within a particular CD44 isoform pathway can be used as an Å6 therapeutic indicator.

In accordance with various embodiments, isoforms CD44s, CD44v1, CD44v2, CD44v3, CD44v4, CD44v5, CD44v5, CD44v6, CD44v7, CD44v8, CD44v9, CD44v10, CD44-HS, and other glycosylated CD44 derivatives, such as those covalently linked with sialyl Lewis$^x$ are Å6 therapeutic indicators based on which a subject or a subpopulation of subjects responsive to Å6 or SEQ ID NO:3 or capped variant therapeutic treatment can be identified. Knowing whether a subject responds to an Å6 or SEQ ID NO:3 or capped variant therapeutic treatment in advance of commencing the treatment will increase the efficacy of the treatment in a subpopulation of subjects suffering from a disease mediated by uncontrolled cell mobility. In an exemplary embodiment of the invention, the effectiveness of Å6 or SEQ ID NO:3 or capped variant therapeutic treatment is increased in a subpopulation of subjects suffering from a disease mediated by uncontrolled cell mobility, who are identified to express CD44v3 differently with respect to, for example, amount or activity when compared to subjects with similar disease who are not responsive to the treatment or when compared to normal subjects.

Accordingly, in an embodiment, the invention provides a method of identifying a subpopulation of Å6 or SEQ ID NO:3 or capped variant-responsive subjects with an agent specific for an Å6 therapeutic indicator. A detection of one or more Å6 therapeutic indicators can be used to identify subjects responsive to Å6 SEQ ID NO:3 or capped variant treatment. A diagnostic or prognostic method depending on one therapeutic indicator can fail for a number of reasons. For example, a selected indicator could fail to identify a positive responder because the selected indicator is not present in a subject, but other indicators are. A selected indicator could also fail to identify a positive responder because the agent recognizing the indicator is not sensitive enough. It is also possible that an indicator fails to identify a positive Å6 or SEQ ID NO:3 or capped variant responder because it is not the right timing for detecting the indicator in a subject who can benefit from Å6 or SEQ ID NO:3 or capped variant treatment. Using a set of therapeutic indicators which is present or activated in different signal transduction pathways or at different stages of the same signal transduction pathway can minimize the above pitfalls of using one therapeutic indicator. The selection of a therapeutic indicator in a set will depend on, for example, the type of the disease and/or the genetic background of a subject. For example, isoforms CD44v7-10 were shown to be overexpressed in prostate cancer, choosing any combination of these isoforms in a set is appropriate for an prostate cancer patient. Using a large number of therapeutic indicators, for example, more than 10 indicators, can be advantageous for providing a molecular profile of molecules in cell mobility signal pathways for a subject so as to better determine disease stages and decide on a better therapeutic strategy.

The number of indicators in a set can be at least two, three, four, five, six, seven, or ten, eleven, more. In some embodiments, at least one indicator in a set is chosen from CD4 variants and at least one indicator of the set is chosen from a signal transduction pathway. Although the presence of either indicator provides an indicator for Å6 or SEQ ID NO:3 or capped variant responsiveness, presence of two indicators provides higher confidence in the predicted Å6 or SEQ ID NO:3 or capped variant responsiveness. A method with a set of more than one Å6 therapeutic indicators can therefore provide a more accurate and reliable prediction.

Once one or more particular Å6 therapeutic indicators are identified in a subject, the subject can be classified with those with similar indicator profiles in a subpopulation responding similarly to Å6 or SEQ ID NO:3 or capped variant therapeutic treatment. A subpopulation of subjects can be grouped based on, for example, the presence/absence, activity or amount of a particular Å6 therapeutic indicators in the subjects. Knowing in advance if a subpopulation of subjects responds to Å6 or SEQ ID NO:3 or capped variant therapy will increase the effectiveness of Å6 or SEQ ID NO:3 or capped variant therapeutic treatment in the subjects having or suspected of having a disease mediated by uncontrolled cell mobility.

Knowing the identity of a subpopulation based on Å6 therapeutic indicators will further allow selection of an effective Å6 or SEQ ID NO:3 or capped variant therapeutic regimen for subjects suffering from a particular disease mediated by uncontrolled cell mobility. In an exemplary embodiment, an effective Å6 or SEQ ID NO:3 or capped variant therapeutic treatment can be selected for a subpopulation of subjects responsive to Å6 or SEQ ID NO:3 or capped variant therapy such as cancer subjects, immune system disorders, and aberrant inflammatory conditions, such as arthritis. In another exemplary embodiment, an effective Å6 or SEQ ID NO:3 or capped variant therapeutic treatment can be selected for a subpopulation of subjects responsive to Å6 or SEQ ID NO:3 or capped variant therapy, whose disease is at a particular stage such as, for example, subjects with metastasic cancers.

In another embodiment, the invention provides a method of identifying a subpopulation of subjects responsive to Å6 or SEQ ID NO:3 or capped variant therapeutic treatment. The method includes the following steps. First, contact a plurality of samples from different subjects of a population having or suspected of having a disease mediated by uncontrolled cell mobility with an agent specific for an Å6 therapeutic indicator. Second, determine the binding of the agent to the Å6 therapeutic indicator in the samples, with the binding being indicative of the presence of the indicator. Third, select subjects from the population having the Å6 therapeutic indicator present in the samples to identify a subpopulation responsive to Å6 or SEQ ID NO:3 or capped variant therapeutic treatment.

Å6 therapeutic indicators are employed in the invention to identify subjects that respond to an Å6 or SEQ ID NO:3 or capped variant treatment. Å6 therapeutic indicators include macromolecules such as polypeptides and their activities that are associated with the positive responses to Å6 or SEQ ID NO:3 or capped variant treatment. Å6 therapeutic indicators are used as identifiers to select subjects who can positively respond to Å6 or SEQ ID NO:3 or capped variant treatment. An Å6 polypeptide or SEQ ID NO:3 or capped variant exhibits activities to inhibit mobility processes such as cell migration and invasion. Å6 therapeutic indicators of the invention are macromolecules relate to cell mobility processes, which are classified into CD44 polypeptides and their associated signal transduction pathway member polypeptides.

The detection of a particular Å6 therapeutic indicator is determined by contacting samples from patients with an agent specifically recognizes the indicator and detecting the specific binding of the agent. An agent specifically recognizes the indicator can be an antibody, a ligand, an interacting polypeptide, a substrate of the indicator, or a nucleic acid complementary to the nucleic acid encoding the indicator. The specific agent should bind with sufficient binding affinity for the indicator or the nucleic acid encoding the indicator, preferably with lower affinity to molecules other than the indicator. Methods for detecting the indicator, either in the form of protein or nuclei acid, are well known in the art. The methods to detect a protein using an antibody, for example, include immunoblotting, ELISA assays, immunocytochemistry, immunohistochemistry, immunoprecipitation, FACS analysis (Harlow and Lane, *Using Antibodies: A Laboratory Manual*, Cold Spring Harbor Press (1999)). Various immunoassays are well known to the skilled in the art and can be modified as desired. All of these methods involve using an antibody specifically recognizes and binds the indictor molecule with sufficient affinity. For example, the antibody can be rendered detectable by incorporation of, or by conjugation to, a detectable moiety, or binding to a secondary molecule that is itself detectable or detectably labeled. Different antibodies can be attached to an array, making it possible to simultaneously detect multiple samples or multiple indictors. In another example, the recognizing agent can also be a substrate of an enzymatic indicator or a detectable ligand that binds to the indicator. The detection of the product of the enzymatic reaction and the labeled ligand can be used to determine the presence of or the change of the amount and activity of the indicator. In another example, the recognizing agent can be a polypeptide that specifically binds to the indicator of interest. The recognizing polypeptide can be used to separate and/or enrich the indicator from the sample. The isolated indicator can be further detected by an antibody. Or the binding of the indicator and the recognizing polypeptide partner can be directly detected by induced conformation change of the recognizing polypeptide, for example, the binding can make non-fluorescent recognizing polypeptide fluorescent.

For example, a sample, preferably a tissue sample is mounted onto a solid surface for histochemical analysis. The presence of detectable, accessible Å6 therapeutic indicator indicates that Å6 therapeutic indicator is present in certain amount or with certain activity. This leads to a favorable diagnosis or prognosis, i.e., the subject is responsive to Å6 or SEQ ID NO:3 or capped variant therapeutic treatment. If, on the other hand, the antibody does not react with the Å6 therapeutic indicator in the tissue section, then there is an expectation that the Å6 therapeutic indicator is not present. This leads to a unfavorable diagnosis or prognosis, i.e., the subject is not responsive to Å6 or SEQ ID NO:3 or capped variant therapeutic treatment.

Methods for producing antibodies are well known in the art. An antibody specific for the polypeptide of the invention can be easily obtained by immunizing an animal with an immunogenic amount of the polypeptide. Therefore, an antibody recognizing the polypeptide of the invention embraces polyclonal antibodies and antiserum which are obtained by immunizing an animal, and which can be confirmed to specifically recognize the polypeptide of the invention by Western blotting, ELISA, immunostaining or other routine procedure known in the art.

It is well known that if a polyclonal antibody can be obtained by sensitization, a monoclonal antibody secreted by a hybridoma can be obtained from the lymphocytes of the sensitized animal (Chapter 6, Antibodies A Laboratory Manual, Cold Spring Harbor Laboratory Press, (1988)). Therefore, monoclonal antibodies recognizing the polypeptide of the invention are also provided. Methods of producing polyclonal and monoclonal antibodies are known to those of skill in the art and described in the scientific and patent literature, see, e.g., Harlow and Lane., *Antibodies: A Laboratory Manual*, Cold Spring Harbor Laboratory Press (1989); Hammerling, et al., in: *Monoclonal Antibodies and T-Cell Hybridomas* 563-681, Elsevier, New York (1981); Harlow et al., *Using Antibodies: A Laboratory Manual*, Cold Spring Harbor Laboratory Press (1999); and *Antibody Engineering: A Practical Guide*, Borrebaeck Ed., W.H. Freeman and Co., Publishers, New York, pp. 103-120 (1991); Coligan, *Current Protocols in Immunology*, Wiley/Green, New York (1991); Stites eds., *Basic and Clinical Immunology* (7th ed.) Lange Medical Publications, Los Altos, Calif., and references cited therein (Stites); Goding, *Monoclonal Antibodies: Principles and Practice* (2nd ed.) Academic Press, New York, N.Y. (1986); and Kohler, *Nature* 256:495 (1975)). Such techniques include selection of antibodies from libraries of recombinant antibodies displayed in phage or similar on cells. See, Huse, *Science* 246:1275 (1989) and Ward, *Nature* 341:544 (1989). Recombinant antibodies can be expressed by transient or stable expression vectors in mammalian cells, as in Norderhaug, *J. Immunol. Methods* 204:77-87 (1997).

In this invention, an antibody also embraces an active fragment thereof. An active fragment means a fragment of an antibody having activity of antigen-antibody reaction. Specifically named, these are active fragments, such as F(ab')2, Fab', Fab, and Fv. For example, F(ab')2 results if the antibody of this invention is digested with pepsin, and Fab results if digested with papain. Fab' results if F(ab')2 is reduced with a reagent such as 2-mercaptoethanol and alkylated with monoiodoacetic acid. Fv is a mono active fragment where the variable region of heavy chain and the variable region of light chain are connected with a linker. A chimeric antibody is obtained by conserving these active fragments and substituting the fragments of another animal for the fragments other than these active fragments. In particular, humanized antibodies are envisioned.

Detection of the presence of an indictor can also be done by detecting the mRNA of the indicator. Various methods to detect a nucleic acid are well known to people skilled in the art (Ausubel et al., *Current Protocols in Molecular Biology*, John Wiley and Sons, Inc. (2007)), including, for example, northern blot hybridization, in situ hybridization, polymerase chain reaction (PCR), quantitative polymerase chain reaction (QPCR), microArray analysis. The mRNA of the indicator can be isolated using standard protocol for RNA isolation or can be directly detected in situ in the sample. Depending on the amount of the mRNA of the interest, it can be detected with or without amplification with PCR. QPCR is an effective method for using to quantitate the change of mRNA amount in different samples.

By using therapeutic indictors associated with positive response to Å6 or SEQ ID NO:3 or capped variant treatment in the samples of subjects, a subpopulation of subjects is selected that are responsive to treatment with an Å6 polypeptide or SEQ ID NO:3 or capped variant. The selected subpopulation could have, for example, at least 10%, 20%, 30%, 40%, 50%, 60%, or up to 100% of the population tested, including any percent in between. This method of invention enables doctors to match the Å6 or SEQ ID NO:3 or capped variant therapy to responsive patients, increase therapeutic effectiveness and minimize the side effects. The subpopulation of subjects can be further classified depending on the Å6 therapeutic indicators present in the samples, for example, a subgroup with Å6 or SEQ ID NO:3 or capped variant binding CD44 variants, and a subgroup with any downstream (or upstream) signal transduction pathway polypeptides. Or the subpopulation can be further classified depending on the expression levels of an Å6 therapeutic indicators such as low, medium, and high. The range of levels of an Å6 therapeutic indicators needs to be determined with a large enough population of patient data, for example, at least 6 to 10 samples in each group, to be meaningful in clinical application. Once the subgroups are determined from patient data, this information can further guide doctors in making decision on dosing schedules tailored to individual patients.

In yet another embodiment, the invention provides a method of identifying a subpopulation of subjects responsive to Å6 or SEQ ID NO:3 or capped variant therapeutic treatment. This method includes the following steps. First, contact a plurality of samples from different subjects of a population having or suspected of having a disease mediated by uncontrolled cell mobility with an agent specific for an Å6 therapeutic indicator. Second, measure a change in the amount or activity of the Å6 therapeutic indicator in the samples compared to an amount or activity from a normal individual. Third, select subjects from the population having the change in the amount or activity of the Å6 therapeutic indicator in the samples to identify a subpopulation responsive to Å6 or SEQ ID NO:3 or capped variant therapeutic treatment.

The method of the invention provides a method of selecting a subpopulation of subjects responsive to Å6 or SEQ ID NO:3 or capped variant treatment by measuring a change in the amount or activity of a Å6 therapeutic indicator in samples of the subjects compared with the amount or activity from a normal individual. A change in the amount or activity of an Å6 therapeutic indicator can be an increase or a decrease of the amount or activity of the Å6 therapeutic indicator. The change is measured between samples of subjects having or subjected to having a disease mediated by uncontrolled cell mobility and samples from a normal individual. If samples of the same subject in his/her normal state is available, these samples are the preferred samples to be compared with. A comparison between samples of the same subject in his/her early and late stage of disease also can be made for prognostic purposes. When a change in the amount or activity of an Å6 therapeutic indicator is indicative of abnormal cell mobility activity, the change can also be used as indicative for positive response to an Å6 treatment.

An Å6 therapeutic indicator wherein an increase of the Å6 therapeutic indicator in a subject is indicative of the positive response to an Å6 or SEQ ID NO:3 or capped variant treatment can be selected from a CD44 polypeptide and a signal transduction pathway polypeptide. CD44 polypeptides that are increased in cells with uncontrolled mobility can be used as Å6 therapeutic indicators. Some signal transduction pathway polypeptides are up-regulated in certain cancers, for examples c-Met (vide supra).

An Å6 therapeutic indicator wherein an change of activity of the Å6 therapeutic indicator in a subject is indicative of the positive response to an Å6 or SEQ ID NO:3 or capped variant treatment can be selected from a CD44 polypeptide and a signal transduction pathway polypeptide.

The amount and/or activity of an Å6 therapeutic indicator in the sample can be determined by detecting the Å6 therapeutic indicator protein using methods known in the art. In this invention, there are no limitations on the type of assay used to measure the amount and/or activity of an Å6 therapeutic indicator. For example, an Å6 therapeutic indicator can be detected by immunoassays using antibodies specific for the Å6 therapeutic indicator. The antibody can be used, for example, in Western blots of two dimensional gels where the protein is identified by enzyme linked immunoassay or in dot blot (Antibody Sandwich) assays of total cellular protein, or partially purified protein.

Methods for sample concentration and protein purification are described in the literature and are known by those skilled in the art. For example, if desired, the Å6 therapeutic indicator present in the sample can be concentrated, by precipitating with ammonium sulfate or by passing the extract through a commercially available protein concentration filter, e.g., an Amicon or Millipore, ultrafiltration unit. The extract can be applied to a suitable purification matrix, such as an anion or a cation exchange resin, or a gel filtration matrix, or subjected to preparative gel electrophoresis. In such cases, the protein yield after each purification step needs to be considered in determining the amount of the Å6 therapeutic indicator in a sample.

An Å6 therapeutic indicator can be detected using an antibody specific for the Å6 therapeutic indicator, and a control assay can be carried out using an antibody specific for another molecule. Optionally, the method can further comprise correlating in an increase or decrease in an Å6 therapeutic indicator in the sample relative to healthy tissue. For example, the binding of an antibody to an Å6 therapeutic indicator in a tumor tissue can be detected and compared it with the antibody binding to any Å6 therapeutic indicator expressed (or non-specific reaction) in healthy tissue.

In accordance with the present invention, there are provided methods for measuring the activity, such as a biological activity, of Å6 therapeutic indicators. Such biological activity can include any measurable activity, such as chemical reactivity, catalytic ability, binding to specific structures and receptors, acting as a receptor, or just being present in a membrane of a cell and therefore available as a target site for antibodies or other agents. Any such indicator polypeptides can thus provide a target for an agent specific for an Å6 therapeutic indicator.

In an embodiment, the change in biological activity of an Å6 therapeutic indicator is a decrease in biological activity. In another embodiment, the change in biological activity an Å6 therapeutic indicator is an increase in biological activity. In these embodiments, the biological activity can be an enzyme activity, such as where the enzyme is one selected from the group kinase, protease, peptidase, phosphodiesterase, phosphatase, dehydrogenase, reductase, carboxylase, transferase, deacetylase and polymerase.

Assays for these enzymes are available, such as for phosphodiesterases (the most pharmacologically relevant phosphodiesterases are those that hydrolyze cyclic nucleotides. See, for example, cAMP and cGMP assays available from Perkin-Elmer®. Protein phosphatases remove phosphate residues from proteins. For example, a non-radioactive phosphatase assay system is available from Promega® Biotech. Dehydrogenases oxidize or reduce small molecular weight metabolites, for example, steroid hormones, or that they generally use or generate NAD or NADP. A commercial assay to test dehydrogenases activity is available from Cayman Chemical®.

In certain embodiments, the Å6 therapeutic indicator is a kinase, a protein kinase, a serine or threonine kinase, or a receptor tyrosine protein kinase. Where the indicator is a protein kinase, especially involving tyrosine kinase, various assays for activity are available. Protein kineses add phosphate groups to serine, threonine or tyrosine residues on proteins. The activity of protein kinases is commonly measured with phospho-serine, threonine, or tyrosine-specific antibodies; generation of radiolabeled substrate; consumption of ATP; phosphorylation of (synthetic) small peptides; or measuring downstream enzyme activity and gene transcription. Such assays are commercially available. (See, for example, the tyrosine kinase assay from Roche Molecular Biochemicals®). Assays for serine/threonine kineses are also available at Upstate Biotechnology®, Inc. and from Applied BioSystems®. In other embodiments, the Å6 therapeutic indicator is a serine protease, cysteine protease or aspartic acid protease. The Å6 therapeutic indicator can also be a methyltransferase, a cytosine methyltransferase or an adenine methyltransferase. The Å6 therapeutic indicator can be a deacetylase, e.g., histone deacetylase; a carboxylase, e.g., y-carboxylase; a peptidase, e.g., zinc peptidase; or a polymerase, e.g., DNA polymerase or RNA polymerase. The activity of the above enzymes can be measured by directly measuring cleavage product or generation of (fluorescent) light after cleavage of synthetic substrates.

In one embodiment, the biological activity an Å6 therapeutic indicator is a receptor activity, where the receptor is a G-protein-coupled receptor (GPCR). GPCRs are transmembrane proteins that wind 7 times back and forth through a cell's plasma membrane with a ligand binding site located on the outside of the membrane surface of the cell and the effector site being present inside the cell. These receptors bind GDP and GTP. In response to ligand binding, GPCRs activate signal transduction pathways which induce a number of assayable physiological changes, e.g., an increase in intracellular calcium levels, cyclic-AMP, inositol phosphate turnover, and downstream gene transcription (directly or via reporter-assays) along with other translocation assays available for measuring GPCR activation when the polypeptide encoded by a gene of the invention is a GPCR. Thus, such proteins work through a second messenger. The result is activation of CREB, a transcription factor that stimulates the production of gene products. One useful assay is the so-called BRET2/arrestin assay, useful in screening for compounds that interact with GPCRs. (See: Bertrand et al, *J. Recept. Signal Transduct Res.*, 22:533-541 (February-November 2002)). In addition, numerous assays are commercially available, such as the Transfluor Assay™, available from Norak Biosciences®, Inc.

In another embodiment, the invention provide a method of further treating the above mentioned subpopulation of Å6 or SEQ ID NO:3 or capped variant responders with therapeutic levels of Å6 polypeptide or SEQ ID NO:3 or capped variant compositions. Since an Å6 polypeptide or SEQ ID NO:3 or capped variant is effective at inhibiting undesired cell mobility, it can ameliorate a disease, pathological condition, or abnormal trait that is mediated by uncontrolled cell mobility. An Å6 polypeptide or SEQ ID NO:3 or capped variant can also be employed to prevent the occurrence or reduce the onset of such a disease, pathological condition, or abnormal trait. In some cases, the selection of a method of Å6 or SEQ ID NO:3 or capped variant therapeutic treatment, i.e., a therapeutic regimen, can incorporate selection of a specific Å6 or SEQ ID NO:3 or capped variant therapy alone or in combination with one or more medical therapies available against a disease mediated with uncontrolled cell mobility. Likewise the selection can be the choice of a therapeutic regimen, which is safer than certain other methods of treatment in the subject.

It is recognized that many treatment methods, e.g., administration of certain compounds or combinations of compounds, can produce side-effects or other deleterious effects in patients. Such effects can limit or even preclude use of the treatment method in particular patients, or can even result in irreversible injury, dysfunction, or death of the patient. Thus, in certain embodiments, the Å6 therapeutic indicator information is used to select an effective Å6 or SEQ ID NO:3 or capped variant therapeutic treatment with reduced general toxicity or reduced side effect.

In a related aspect, the invention concerns a method for providing a correlation or other statistical test of relationship between a subject with Å6 therapeutic indicator and effectiveness of the Å6 or SEQ ID NO:3 or capped variant therapeutic treatment. In one embodiment, an effective Å6 or SEQ ID NO:3 or capped variant treatment regimen can be assessed by determining the presence/absence, amount or activity of a particular Å6 therapeutic indicator in a subject suffering from a disease mediated by uncontrolled cell mobility, and providing a result indicating the expected effectiveness of a treatment for the disease or condition. The result can be formulated by comparing the subpopulation of the subject with a list of Å6 therapeutic indicators indicative of the effectiveness of a treatment, e.g., administration of Å6 polypeptide or SEQ ID NO:3 or capped variant described herein. The determination can be by methods as described herein or other methods known to those skilled in the art.

Thus, the invention is also directed to selecting an effective Å6 or SEQ ID NO:3 or capped variant treatment regimen for administration to a subject suffering from a disease or condition mediated by uncontrolled cell mobility. In an embodiment, the selection of a effective Å6 or SEQ ID NO:3 or capped variant treatment regimen involves selecting a dosage level or frequency of administration or route of administration of Å6 polypeptides or the peptide of SEQ ID NO:3 or capped variants combinations of those parameters. In other embodiments, Å6 polypeptides or the peptide of SEQ ID NO:3 or capped variants are administered with one or more other compounds in compositions, and the selecting involves selecting a method of administration for Å6 polypeptides or the peptide of SEQ ID NO:3 or capped variants with one, two, or more than two other compounds, jointly, concurrently, or separately. As understood by those skilled in the art, such plurality of compounds can be used in combination therapy, and thus can be formulated in a single drug, or can be separate drugs administered concurrently, serially, or separately.

In various embodiments, concurrently with selecting populations having Å6 therapeutic indicators and identifying a subpopulation responsive to Å6 or SEQ ID NO:3 or capped variant therapeutic treatment, the invention provides the following methods for determining the efficacy of Å6 or SEQ ID NO:3 or capped variant therapeutic treatment in the subpopulation of subjects. See also U.S. Pat. No. 6,936,587.

The compounds of the invention are tested for their anti-invasive capacity in a Matrigel™ invasion assay system as described in detail by Albini et al., *Cancer Res.,* 47:3239-3245 (1987) and Parish et al., *Int. J. Cancer,* 52:378-383 (1992), which references are hereby incorporated by reference in their entirety. The assay is performed with a cell line, more preferably a tumor cell line, most preferably the rat breast cancer (Mat BIII) line or the human prostate cancer (PC-3) line (Xing et al. *Int. J. Cancer,* 67(3):423-429 (1996); Hoosein et al., *Cancer Commun.* 8:255-64 (1991)).

Matrigel™ is a reconstituted basement membrane containing type IV collagen, laminin, heparan sulfate proteoglycans such as perlecan, which bind to and localize bFGF, vitronectin as well as transforming growth factor-β (TGFβ), urokinase-type plasminogen activator (uPA), tissue plasminogen activator (tPA), and the serpin known as plasminogen activator inhibitor type I (PAI-1) (Chambers et al., *Cancer* 75(7): 1627-33 (1995)). It is accepted in the art that results obtained in this assay for compounds which target extracellular receptors or enzymes are predictive of the efficacy of these compounds in vivo (Rabbani et al., *Int. J. Cancer,* 63:840-845 (1995)).

The peptides of this invention are tested for their anti-angiogenic activity in one of two different assay systems in vitro. Endothelial cells, for example, human umbilical vein endothelial cells (HUVEC) or human microvascular endothelial cells (HMVEC) which can be prepared or obtained commercially, are mixed at a concentration of $2 \times 10^5$ cells/mL with fibrinogen (5 mg/mL in phosphate buffered saline (PBS) in a 1:1 (v/v) ratio). Thrombin is added (5 units/mL final concentration) and the mixture is immediately transferred to a 24-well plate (0.5 mL per well). The fibrin gel is allowed to form and then VEGF and bFGF are added to the wells (each at 5 ng/mL final concentration) along with the test compound (e.g., Å6 polypeptide compound or compositions). The cells are incubated at 37° C. in 5% $CO_2$ for 4 days at which time the cells in each well are counted and classified as either rounded, elongated with no branches, elongated with one branch, or elongated with 2 or more branches. Results are expressed as the average of 5 different wells for each concentration of compound. Typically, in the presence of angiogenic inhibitors, cells remain either rounded or form undifferentiated tubes (e.g. 0 or 1 branch). This assay is recognized in the art to be predictive of angiogenic (or anti-angiogenic) efficacy in vivo (Min et al., *Cancer Res.* 56(10):2428-33 (1996)).

In an alternate assay, endothelial cell tube formation is observed when endothelial cells are cultured on Matrigel™ (Schnaper et al., *J. Cell. Physiol.* 165(1):107-118 (1995)). Endothelial cells ($1 \times 10^4$ cells/well) are transferred onto Matrigel™ coated 24-well plates, and tube formation is quantitated after 48 hrs. Inhibitors (i.e., Å6 polypeptide or SEQ ID NO:3 or capped variant compositions) are tested by adding them either at the same time as the endothelial cells or at various time points thereafter. This assay models angiogenesis by presenting to the endothelial cells a particular type of basement membrane, namely the layer of matrix which migrating and differentiating endothelial cells might be expected to first encounter. In addition to bound growth factors, the matrix components found in Matrigel™ (and in basement membranes in situ) or proteolytic products thereof can also be stimulatory for endothelial cell tube formation which makes this model complementary to the fibrin gel angiogenesis model previously described (Blood and Zetter, *Biochim. Biophys. Acta.* 1032(1):89-118 (1990); Odedra et al., *Pharmacol. Ther.* 49(1-2):111-124 (1991)). The compounds of this invention (i.e., Å6 polypeptide or SEQ ID NO:3 or capped variant compositions) inhibit endothelial cell tube formation in both assays, which suggests that the compounds will also have anti-angiogenic activity.

The peptides, peptidomimetics and conjugates are tested for therapeutic efficacy in several well established rodent models which are considered to be highly representative of a broad spectrum of human tumors. The approaches are described in detail in Geran et al., *Canc. Chemother. Reports,* Pt 3, 3:1-112, which is hereby incorporated by reference in its entirety. All general test evaluation procedures, measurements and calculations are performed in accordance with this reference, including mean survival time, median survival time, calculation of approximate tumor weight from measurement of tumor diameters with vernier calipers; calculation of tumor diameters; calculation of mean tumor weight from individual excised tumors; and ratios between treated and control groups ratio for any measure (T/C ratios).

The effects of the compounds are tested on tumor progression in a rat syngeneic model of breast cancer (Xing and Rabbani, (1996) supra). Mat BIII rat breast tumor cells ($1 \times 10^6$ cells in PBS, 0.1 mL per rat) are inoculated into the mammary fat pads of female Fisher rats. The test compound is dissolved in PBS (200 mM stock), sterile filtered and dispensed in vivo at a dose of up to about 100 mg/kg/day) using a 14-day Alza osmotic mini-pump implanted intraperitoneally at the time of inoculation. Control animals receive vehicle (PBS) alone. Animals are euthanized at day 14 and examined for metastasis in the spleen, lungs, liver, kidney and lymph nodes. In addition, the primary tumors are excised, quantitated, and prepared for immunohistochemistry.

3LL Lewis Lung Carcinoma arose spontaneously in 1951 as carcinoma of the lung in a C57BL/6 mouse (Kanematsu et al. *Cancer Res* 15:38-51 (1955)). See, also Malave et al., *J. Nat'l. Canc. Inst.* 62:83-88 (1979)). It is propagated by passage in C57BL/6 mice by subcutaneous (sc) inoculation and is tested in semiallogeneic C57BL/6xDBA/2 $F_1$ mice or in allogeneic C3H mice. Typically six animals per group for subcutaneously (sc) implant, or ten for intramuscular (im) implant are used. Tumor can be implanted sc as a 2-4 mm fragment, or im or sc as an inoculum of suspended cells of about $0.5-2 \times 10^6$ cells. Treatment begins 24 hours after implant or is delayed until a tumor of specified size (usually approximately 400 mg) can be palpated. The test compound is administered intraperitoneal (ip) daily for 11 days.

Animals are followed by weighing, palpation, and measurement of tumor size. Typical tumor weight in untreated control recipients on day 12 after inoculation is 500-2500 mg. Typical median survival time is 18-28 days. A positive control compound, for example cyclophosphamide at 20 mg/kg/injection per day on days 1-11 is used. Results computed include mean animal weight, tumor size, tumor weight, survival time for confirmed therapeutic activity, the test composition should be tested in two multi-dose assays.

The following lung cancer model has been utilized by a number of investigators. See, for example, Gorelik et al., *J.*

Nat'l. Canc. Inst. 65:1257-1264 (1980); Gorelik et al., *Rec. Results Canc. Res.* 75:20-28 (1980); Isakov et al., *Invasion Metas.* 2:12-32 (1982); Talmadge et al., *J. Nat'l. Canc. Inst.* 69:975-980 (1982); Hilgard et al., *Br. J. Cancer* 35:78-86 (1977)). Test mice are male C57BL/6 mice, 2-3 months old. Following sc, im, or intra-footpad implantation, this tumor produces metastases, preferentially in the lungs. With some lines of the tumor, the primary tumor exerts anti-metastatic effects and must first be excised before study of the metastatic phase (see also U.S. Pat. No. 5,639,725).

Single-cell suspensions are prepared from solid tumors by treating minced tumor tissue with a solution of 0.3% trypsin. Cells are washed 3 times with PBS (pH 7.4) and suspended in PBS. Viability of the 3LL cells prepared in this way is generally about 95-99% (by trypan blue dye exclusion). Viable tumor cells ($3\times10^4$-$5\times10^6$) suspended in 0.05 ml PBS are injected subcutaneously, either in the dorsal region or into one hind foot pad of C57BL/6 mice. Visible tumors appear after 3-4 days after dorsal sc injection of $10^6$ cells. The day of tumor appearance and the diameters of established tumors are measured by caliper every two days. The treatment is given as one or two doses of peptide or derivative, per week. In another embodiment, the peptide is delivered by osmotic minipump.

In experiments involving tumor excision of dorsal tumors, when tumors reach about 1500 mm$^3$ in size, mice are randomized into two groups: (1) primary tumor is completely excised; or (2) sham surgery is performed and the tumor is left intact. Although tumors from 500-3000 mm$^3$ inhibit growth of metastases, 1500 mm$^3$ is the largest size primary tumor that can be safely resected with high survival and without local regrowth. After 21 days, all mice are sacrificed and autopsied.

Lungs are removed and weighed. Lungs are fixed in Bouin's solution and the number of visible metastases is recorded. The diameters of the metastases are also measured using a binocular stereoscope equipped with a micrometer-containing ocular under 8× magnification. On the basis of the recorded diameters, it is possible to calculate the volume of each metastasis. To determine the total volume of metastases per lung, the mean number of visible metastases is multiplied by the mean volume of metastases. To further determine metastatic growth, it is possible to measure incorporation of $^{125}$IdUrd (iododeoxyuridine) into lung cells (Thakur et al., *J. Lab. Clin. Med.* 89:217-228 (1977)). Ten days following tumor amputation, 25 μg of fluorodeoxyuridine is inoculated into the peritoneums of tumor-bearing (and, if used, tumor-resected mice). After 30 min, mice are given 1 μCi of $^{125}$IdUrd. One day later, lungs and spleens are removed and weighed, and a degree of $^{125}$IdUrd incorporation is measured using a gamma counter.

In mice with footpad tumors, when tumors reach about 8-10 mm in diameter, mice are randomized into two groups: (1) legs with tumors are amputated after ligation above the knee joints; or (2) mice are left intact as nonamputated tumor-bearing controls. (Amputation of a tumor-free leg in a tumor-bearing mouse has no known effect on subsequent metastasis, ruling out possible effects of anesthesia, stress or surgery). Mice are killed 10-14 days after amputation. Metastases are evaluated as described above.

Statistics: Values representing the incidence of metastases and their growth in the lungs of tumor-bearing mice are not normally distributed. Therefore, non-parametric statistics such as the Mann-Whitney U-Test can be used for analysis.

Study of this model by Gorelik et al., supra showed that the size of the tumor cell inoculum determined the extent of metastatic growth. The rate of metastasis in the lungs of operated mice was different from primary tumor-bearing mice. Thus in the lungs of mice in which the primary tumor had been induced by inoculation of larger doses of 3LL cells ($1$-$5\times10^6$) followed by surgical removal, the number of metastases was lower than that in nonoperated tumor-bearing mice, though the volume of metastases was higher than in the nonoperated controls. Using $^{125}$IdUrd incorporation as a measure of lung metastasis, no significant differences were found between the lungs of tumor-excised mice and tumor-bearing mice originally inoculated with $1\times10^6$ 3LL cells. Amputation of tumors produced following inoculation of $1\times10^5$ tumor cells dramatically accelerated metastatic growth. These results were in accord with the survival of mice after excision of local tumors. The phenomenon of acceleration of metastatic growth following excision of local tumors had been repeatedly observed (for example, see U.S. Pat. No. 5,639,725). These observations have implications for the prognosis of patients who undergo cancer surgery.

The compounds of this invention are also tested for inhibition of late metastasis using an experimental metastasis model (Crowley et al., *Proc. Natl. Acad. Sci. U.S.A.*, 90(11): 5021-5025 (1993)). Late metastasis involves the steps of attachment and extravasation of tumor cells, local invasion, seeding, proliferation and angiogenesis.

Human prostatic carcinoma cells (PC-3) transfected with a reporter gene, preferably the green fluorescent protein (GFP) gene, but as an alternative with a gene encoding the enzymes chloramphenicol acetyl-transferase (CAT), luciferase or LacZ. This permits utilization of either of these markers (fluorescence detection of GFP or histochemical colorimetric detection of enzymatic activity) for following the fate of these cells. Cells are injected, preferably iv, and metastases identified after about 14 days, particularly in the lungs but also in regional lymph nodes, femurs and brain. This mimics the organ tropism of naturally occurring metastases of prostate cancer. For example, GFP-expressing PC-3 cells ($1\times10^6$ cells per mouse) are injected iv into the tail veins of nude (nu/nu) mice. Animals are also implanted with mini-pumps (subdermally on the back) dispensing either the test compound (at least about 100 mg/kg/day) or vehicle. The animals are euthanized after 14 days and their organs prepared for histological examination. Single metastatic cells and foci are visualized and quantitated by fluorescence microscopy or light microscopic histochemistry or by grinding the tissue and quantitative colorimetric assay of the detectable label.

For a compound to be useful in accordance with this invention, it should demonstrate anti-tumor activity in the above models, for example, blocking tumor progression, angiogenesis and/or metastasis.

Angiogenesis is measured by determining microvessel density using immunostaining for CD31 (also known as platelet-endothelial cell adhesion molecule or PECAM). Results are reported as the average microvessel density of 5 fields each from 5 different sections (Penfold et al., 1996). Typically, the whole tumor is excised, sectioned and the sections examined histologically for microvessel density using appropriate stains or labels for other markers.

The present invention also provides a method of diagnosing a condition characterized by aberrant cell migration and/or invasion that includes imaging the binding or downstream activity of an Å6 polypeptide or SEQ ID NO:3 or capped variant. Imaging can be accomplished by providing an Å6 polypeptide or SEQ ID NO:3 or capped variant covalently bound to an imaging agent.

Å6 polypeptides or the peptide of SEQ ID NO:3 or capped variants can be labeled for detection and/or quantification in methods of the invention, for example, to detect a binding site for the peptide on the surface or in the interior of a cell. Thus, the fate of the peptide can be followed in vitro or in vivo by using the appropriate method to detect the label. The labeled peptide can also be utilized in vivo for diagnosis and prognosis, for example to image occult metastatic foci or for other types of in situ evaluations.

Examples of suitable detectable labels are radioactive, fluorogenic, chromogenic, or other chemical labels. Useful radiolabels, which are detected by a gamma counter or a scintillation counter or by autoradiography include isotopic labels such as $^3H$, $^{125}I$, $^{131}I$, $^{35}S$ and $^{14}C$. In addition, $^{131}I$ is also useful as a therapeutic isotope.

Common fluorescent labels include fluorescein isothiocyanate, rhodamine, phycoerythrin, phycocyanin, allophycocyanin, o-phthaldehyde and fluorescamine.

The fluorophore, such as the dansyl group, can be excited by light of a particular wavelength to fluoresce. (See, for example, Haugland, Handbook of Fluorescent Probes and Research Chemicals, Sixth Edition, Molecular Probes, Eugene, Oreg., 1996). In general, a fluorescent reagent is selected based on its ability to react readily with an amino function. Examples of such fluorescent probes include the Bodipy (4,4-difluoro-4-bora-3a,4a-diaza-5-indacene) fluorophores which span the visible spectrum (U.S. Pat. No. 4,774,339; U.S. Pat. No. 5,187,288; U.S. Pat. No. 5,248,782; U.S. Pat. No. 5,274,113; U.S. Pat. No. 5,433,896; U.S. Pat. No. 5,451,663). One particularly useful member of this group is 4,4-difluoro-5,7-dimethyl-4-bora-3a,4a-diaza-s-indacene-3-propionic acid.

Fluorescein, fluorescein derivatives and fluorescein-like molecules such as OREGON GREEN™ and its derivatives, RHODAMINE GREEN™ and RHODOL GREEN™, are coupled to amine groups using the isocyanate, succinimidyl ester or dichlorotriazinyl-reactive groups. The long wavelength rhodamines, which are basically RHODAMINE GREEN™ derivatives with substituents on the nitrogens, are among the most photostable fluorescent labeling reagents known. Their spectra are not affected by changes in pH between 4 and 10, an important advantage over the fluoresceins for many biological applications: This group includes the tetramethylrhodamines, X-rhodamines and Texas Red derivatives. Other preferred fluorophores for derivatizing the peptide according to this invention are those which are excited by ultraviolet light. Examples include cascade blue, coumarin derivatives, naphthalenes (of which dansyl chloride is a member), pyrenes and pyridyloxazole derivatives.

In yet another approach, one or more amino groups is allowed to react with reagents that yield fluorescent products, for example, fluorescamine, dialdehydes to such as o-phthaldialdehyde, naphthalene-2,3-dicarboxylate and anthracene-2,3-dicarboxylate. 7-nitrobenz-2-oxa-1,3-diazole (NBD) derivatives, both chloride and fluoride, are useful to modify amines to yield fluorescent products.

Those skilled in the art will recognize that known fluorescent reagents modify groups other than amines, such as thiols, alcohols, aldehydes, ketones, carboxylic acids and amides. Hence, fluorescent substrates can readily be designed and synthesized using these other reactive groups.

The peptides can also be labeled for detection using fluorescence-emitting metals such as 152 Eu, or others of the lanthanide series. These metals can be attached to the peptide using such metal chelating groups as diethylenetriaminepentaacetic acid (DTPA) or ethylenediaminetetraacetic acid (EDTA). The peptide can be made detectable by coupling it to a chemiluminescent compound. The presence of the chemiluminescent-tagged peptide is then determined by detecting the presence of luminescence that arises during the course of a chemical reaction. Examples of particularly useful chemiluminescers are luminol, isoluminol, theromatic acridinium ester, imidazole, acridinium salt and oxalate ester. Likewise, a bioluminescent compound can be used to label the peptide. Bioluminescence is a type of chemiluminescence found in biological systems in which a catalytic polypeptide increases the efficiency of the chemiluminescent reaction. The presence of a bioluminescent polypeptide is determined by detecting the presence of luminescence. Important bioluminescent compounds for purposes of labeling are luciferin, luciferase and aequorin.

In yet another embodiment, colorimetric detection is used, based on chromogenic compounds (chromophores) with high extinction coefficients.

In situ detection of the labeled peptide can be accomplished by removing a histological specimen from a subject and examining it by microscopy under appropriate conditions to detect the label. Those of ordinary skill will readily perceive that any of a wide variety of histological methods (such as staining procedures) can be modified in order to achieve such in situ detection.

There are many different labels and methods of labeling known to those of ordinary skill in the art. Examples of the types of labels which can be used in the present invention include radioactive isotopes, paramagnetic isotopes, and compounds which can be imaged by positron emission tomography (PET). Those of ordinary skill in the art will know of other suitable labels for binding to the peptides used in the invention, or will be able to ascertain such, by routine experimentation. Furthermore, the binding of these labels to the peptide or derivative can be done using standard techniques known to those of ordinary skill in the art.

For diagnostic in vivo radioimaging, the type of detection instrument available is a major factor in selecting a given radionuclide. The radionuclide chosen should have a type of decay which is detectable by a given type of instrument. In general, any conventional method for visualizing diagnostic imaging can be utilized in accordance with this invention. Another factor in selecting a radionuclide for in vivo diagnosis is that the half-life of a radionuclide be long enough so that it is still detectable at the time of maximum uptake by the target issue, but short enough so that deleterious radiation of the host is minimized. In one embodiment, a radionuclide used for in vivo imaging does not emit particles, but produces a large number of photons in a 140-200 keV range, which can be readily detected by conventional gamma cameras.

For in vivo diagnosis, radionuclides can be bound to peptide either directly or indirectly by using an intermediary functional group. Intermediary functional groups that are often used to bind radioisotopes, which exist as metallic ions, to peptides are the chelating agents, DTPA and EDTA. Examples of metallic ions which can be bound to peptides are $^{99}Tc$, $^{123}I$, $^{111}In$, $^{131}I$, $^{97}Ru$, $^{67}Cu$, $^{67}Ga$, $^{125}I$, $^{68}Ga$, $^{72}As$, $^{89}Zr$, and $^{201}Tl$. Generally, the dosage of peptide labeled for detection for diagnostic use will vary depending on considerations such as age, condition, sex, and extent of disease in the patient, counterindications, if any, and other variables, to be adjusted by the individual physician. Dosage can vary from 0.01 mg/kg to 100 mg/kg.

In another embodiment, the peptides of the present invention are used as affinity ligands for binding the peptide's receptor in assays, preparative affinity chromatography or solid phase separation. Such compositions can also be used to enrich, purify or isolate cells to which the peptide or derivative binds, preferably through a specific receptor-ligand interaction. The peptide or derivative is immobilized using common methods known in the art, e.g. binding to CNBr-activated SEPHAROSE® or AGAROSE®, NHS-AGAROSE® or SEPHAROSE®, epoxy-activated SEPHAROSE® or AGAROSE®, EAH-SEPHAROSE® or AGAROSE®, streptavidin-SEPHAROSE® or AGAROSE® in conjunction with biotinylated peptide or derivatives. In general the peptides or derivatives of the invention can be immobilized by any other method which is capable of immobilizing these compounds to a solid phase for the indicated purposes. See, for example Affinity Chromatography: Principles and Methods (Pharmacia LKB Biotechnology). Thus, one embodiment is a composition comprising any of the peptides, derivatives or peptidomimetics described herein, bound to a solid support or a resin. The compound can be bound directly or via a spacer, such as an aliphatic chain having about 2-12 carbon atoms.

In some embodiments, the present invention provides a method of screening for compounds that bind an Å6-binding polypeptide that includes adding a test compound and a peptide of SEQ ID NO:1 or SEQ ID NO:3 or capped variant to an Å6 binding polypeptide and measuring the competitive binding of the test compound with SEQ ID NO:1. The Å6-binding polypeptide can include any variant of CD44 as discussed above.

The test compounds identified as favorable candidates can be screened for their anti-angiogenic activity in in vitro assay systems, such as the Boyden chamber assay. Boyden introduced this assay for the analysis of leukocyte chemotaxis. The assay is based on a chamber of two medium-filled compartments separated by a microporous membrane. Cells are placed in the upper compartment and are allowed to migrate through the pores of the membrane into the lower compartment, in which one or more chemotactic agents are present. After an appropriate incubation time, the membrane between the two compartments is fixed and stained, and the number of cells that have migrated to the lower side of the membrane is determined. A number of different Boyden chamber devices are available commercially.

In some embodiments the Å6 polypeptides can exist as addition variants which can include any number of additional amino acids added to SEQ ID NO:1 and still maintain at least 20% of its biological activity as a modulator of CD44 binding interaction with hyaluronic acid. Addition variants can include up to 1 additional amino acid, and up to 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 130, 140, 150, 160, 170, 180, 190, and 200 additional amino acids, including any integer in between these values. The addition variant can include additional amino acids at the N-terminus, the C-terminus, or both.

In some embodiments, methods of the invention use peptides based on SEQ ID NO:1 in which one or more amino acid residues has been substituted as long as the peptide still maintains at least 20% of its biological activity as a modulator of CD44 binding interaction with hyaluronic acid. For a detailed description of protein chemistry and structure, see Schulz et al., *Principles of Protein Structure*, Springer-Verlag, New York, N.Y. (1979); and Creighton, *Proteins: Structure and Molecular Principles*, W. H. Freeman & Co., San Francisco, Calif., (1984), which are hereby incorporated by reference. The types of substitutions which can be made in the peptide molecule of the present invention can be conservative substitutions and are defined herein as exchanges within one of the following groups: 1. Small aliphatic, nonpolar or slightly polar residues: e.g., Ala, Ser, Thr, Gly; 2. Polar, negatively charged residues and their amides: e.g., Asp, Asn, Glu, Gln; 3. Polar, positively charged residues: e.g., His, Arg, Lys.

Pro, because of its unusual geometry, tightly constrains the peptide chain. Substantial changes in functional properties are made by selecting substitutions that are less conservative, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain. Most substitutions according to the present invention are those which do not produce radical changes in the characteristics of the peptide molecule. Even when it is difficult to predict the exact effect of a substitution in advance of doing so, one skilled in the art will appreciate that the effect can be evaluated by routine screening assays, preferably the biological assay described below. Modifications of peptide properties including redox or thermal stability, hydrophobicity, susceptibility to proteolytic degradation or the tendency to aggregate with carriers or into multimers are assayed by methods well known to the ordinarily skilled artisan. Additionally, any of the peptides related to SEQ ID NO:1 can be used in any salt form, including pharmaceutically acceptable salt form. Such salt forms may be useful in any in vivo diagnostic for example. SEQ ID NO:1 and its congeners may also be used in a prodrug form as described above.

In some embodiments, a derivative includes peptides in which the amino and carboxyl termini can be blocked or "capped" with acetyl (Ac—, bound to the amino-terminal N; also abbreviated as "Ac") and amido (—$NH_2$ bound to the C-terminal carboxyl group; also abbreviated as "Am"), respectively. Such blocked peptides are also referred to as part of the single letter peptide code indicating the blocking groups as Ac and Am, for example, Ac-KPSSPPEE-Am.

More generally, the N-terminal capping function can be any linkage to the terminal amino group including, for example, formyl, alkanoyl, having from 1 to 10 carbon atoms, such as acetyl, propionyl, butyryl, alkenoyl, having from 1 to 10 carbon atoms, such as hex-3-enoyl, alkynoyl, having from 1 to 10 carbon atoms, such as hex-5-ynoyl, aroyl, such as benzoyl or 1-naphthoyl, heteroaroyl, such as 3-pyrroyl or 4-quinoloyl, alkylsulfonyl, such as methanesulfonyl, arylsulfonyl, such as benzenesulfonyl or sulfanilyl, heteroarylsulfonyl, such as pyridine-4-sulfonyl, substituted alkanoyl, having from 1 to 10 carbon atoms, such as 4-aminobutyryl, substituted alkenoyl, having from 1 to 10 carbon atoms, such as 6-hydroxy-hex-3-enoyl, substituted alkynoyl, having from 1 to 10 carbon atoms, such as 3-hydroxy-hex-5-ynoyl, substituted aroyl, such as 4-chlorobenzoyl or 8-hydroxy-naphth-2-oyl, substituted heteroaroyl, such as 2,4-dioxo-1,2,3,4-tetrahydro-3-methyl-quinazolin-6-oyl, substituted alkylsulfonyl, such as 2-aminoethanesulfonyl, substituted arylsulfonyl, such as 5-dimethylamino-1-naphthalenesulfonyl, substituted heteroarylsulfonyl, such as 1-methoxy-6-isoquinolinesulfonyl, carbamoyl or thiocarbamoyl, substituted carbamoyl (R'—NH—CO) or substituted thiocarbamoyl (R'—NH—CS) wherein R' is alkyl, alkenyl, alkynyl, aryl, heteroaryl, substituted alkyl, substituted alkenyl, substituted alkynyl, substituted aryl, or substituted heteroaryl, substituted carbamoyl (R'—NH—CO) and substituted thiocarbamoyl (R'—NH—CS) wherein R' is alkanoyl, alkenoyl, alkynoyl, aroyl, heteroaroyl, substituted alkanoyl, substituted alkenoyl, substituted alkynoyl, substituted aroyl, or substituted heteroaroyl, all as above defined.

The C-terminal capping function can either be in an amide bond with the terminal carboxyl or in an ester bond with the terminal carboxyl. Capping functions that provide for an amide bond are designated as $NR^1R^2$ wherein $R^1$ and $R^2$ may be independently drawn from the following group: hydrogen, alkyl, preferably having from 1 to 10 carbon atoms, such as methyl, ethyl, isopropyl, alkenyl, preferably having from 1 to 10 carbon atoms, such as prop-2-enyl, alkynyl, preferably having from 1 to 10 carbon atoms, such as prop-2-ynyl, substituted alkyl having from 1 to 10 carbon atoms, such as hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl, substituted alkenyl having from 1 to 10 carbon atoms, such as hydroxyalkenyl, alkoxyalkenyl, mercaptoalkenyl, alkylthioalkenyl, halogenoalkenyl, cyanoalkenyl, aminoalkenyl, alkylaminoalkenyl, dialkylaminoalkenyl, alkanoylalkenyl, carboxyalkenyl, carbamoylalkenyl, substituted alkynyl having from 1 to 10 carbon atoms, such as hydroxyalkynyl, alkoxyalkynyl, mercaptoalkynyl, alkylthioalkynyl, halogenoalkynyl, cyanoalkynyl, aminoalkynyl, alkylaminoalkynyl, dialkylaminoalkynyl, alkanoylalkynyl, carboxyalkynyl, carbamoylalkynyl, aroylalkyl having up to 10 carbon atoms, such as phenacyl or 2-benzoylethyl, aryl, such as phenyl or 1-naphthyl, heteroaryl, such as 4-quinolyl, alkanoyl having from 1 to 10 carbon atoms, such as acetyl or butyryl, aroyl, such as benzoyl, heteroaroyl, such as 3-quinoloyl, OR' or NR'R" where R' and R" are independently hydrogen, alkyl, aryl, heteroaryl, acyl, aroyl, sulfonyl, sulfinyl, or SO$_2$—R''' or SO—R''' where R''' is substituted or unsubstituted alkyl, aryl, heteroaryl, alkenyl, or alkynyl.

Capping functions that provide for an ester bond are designated as OR, wherein R may be: alkoxy; aryloxy; heteroaryloxy; aralkyloxy; heteroaralkyloxy; substituted alkoxy; substituted aryloxy; substituted heteroaryloxy; substituted aralkyloxy; or substituted heteroaralkyloxy.

Either the N-terminal or the C-terminal capping function, or both, may be of such structure that the capped molecule functions as a prodrug (a pharmacologically inactive derivative of the parent drug molecule) that undergoes spontaneous or enzymatic transformation within the body in order to release the active drug and that has improved delivery properties over the parent drug molecule (Bundgaard, (1985)).

Judicious choice of capping groups allows the addition of other activities on the peptide. For example, the presence of a sulfhydryl group linked to the N- or C-terminal cap will permit conjugation of the derivatized peptide to other molecules.

Capping of the peptide is intended primarily to increase plasma half life, as has been demonstrated for many peptides (e.g., Powell et al., *Ann Repts Med. Chem.* 28:285-294 (1993)). Any capping group which serves this function is intended. However, the uncapped form is still useful as a template for peptidomimetic design (see below) and may have equally activity in vitro.

The Å6 polypeptides or the peptide of SEQ ID NO:3 or capped variants used in methods of the present invention can exist as therapeutically acceptable salts. Suitable salts include those formed with both organic and inorganic acids. Such acid addition salts will normally be pharmaceutically acceptable. However, salts of non-pharmaceutically acceptable salts can be of utility in the preparation and purification of the compound in question. Basic addition salts can also be formed and be pharmaceutically acceptable. For a more complete discussion of the preparation and selection of salts, see Stal, *Pharmaceutical Salts: Properties, Selection*, and Use, Wiley-VCHA, Zurich, Switzerland (2002).

Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Basic groups in the peptides of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Salts can also be formed by coordination of the compounds with an alkali metal or alkaline earth ion. Hence, the present invention contemplates sodium, potassium, magnesium, and calcium salts of the compounds of the compounds of the present invention and the like.

Basic addition salts can be prepared during the final isolation and purification of the peptides by reacting a carboxylic acid group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylammonium, dimethylammonium, trimethylammonium, triethylammonium, diethylammonium, ethylammonium, tributylammonium, pyridine, N,N-dimethylanilinium, N-methylpiperidinium, N-methylmorpholinium, dicyclohexylammonium, procaine, dibenzylammonium, N,N-dibenzylphenethylammonium, 1-ephenammonium, and N,N'-dibenzylethylenediammonium. Other representative organic amines useful for the formation of base addition salts include ethylenediamine, ethanolamine, diethanolamine, piperidine, and piperazine.

While the Å6 polypeptides or the peptide of SEQ ID NO:3 or capped variants can be administered as the raw chemical, they can also be administered as a pharmaceutical formulation. A pharmaceutical formulation includes a compound or a pharmaceutically acceptable salt, ester, prodrug or solvate thereof, together with one or more pharmaceutically acceptable carriers thereof and optionally one or more other therapeutic ingredients. The carrier(s) should be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; see for example, Remington's Pharmaceutical Sciences. The pharmaceutical compositions of the present invention may be manufactured in a manner that is itself known, for example, by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. formulations can be prepared by uniformly and intimately bringing into association the active ingredient with liquid carriers or finely divided solid carriers or both and then, if necessary, shaping the product into the desired formulation.

Formulations suitable for oral administration can be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient can also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders, inert diluents, or lubricating, surface active or dispersing agents. Molded tablets can be made by molding in a suitable machine a mixture of the powdered compound moistened with an inert liquid diluent. The tablets can optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions can be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The Å6 polypeptides or the peptide of SEQ ID NO:3 or capped variants can be formulated for parenteral administration by injection, e.g., by bolus injection or continuous infusion. Formulations for injection may be presented in unit dosage form, e.g., in ampoules or in multi-dose containers, with an added preservative. The Å6 polypeptides or the peptide of SEQ ID NO:3 or capped variants may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions can be prepared from sterile powders, granules and tablets of the kind previously described.

Formulations for parenteral administration include aqueous and non-aqueous (oily) sterile injection solutions of the Å6 polypeptides or the peptide of SEQ ID NO:3 or capped variants which can contain antioxidants, buffers, bacteriostats and solutes which render the formulation isotonic with the blood of the intended recipient; and aqueous and non-aqueous sterile suspensions which can include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions.

In addition to the formulations described above, the Å6 polypeptides or the peptide of SEQ ID NO:3 or capped variants can also be formulated as a depot preparation. Such long acting formulations can be administered by implantation (for example subcutaneously or intramuscularly) or by intramuscular injection. Thus, for example, the Å6 polypeptides or the peptide of SEQ ID NO:3 or capped variants can be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the Å6 polypeptides or the peptide of SEQ ID NO:3 or capped variants can take the form of tablets, lozenges, pastilles, or gels formulated in conventional manner. Such compositions can include the active ingredient in a flavored basis such as sucrose and acacia or tragacanth.

The compounds can also be formulated in rectal compositions such as suppositories or retention enemas, e.g., containing conventional suppository bases such as cocoa butter, polyethylene glycol, or other glycerides.

Å6 polypeptides or the peptide of SEQ ID NO:3 or capped variants can be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient can include, for topical administration, from 0.001% to 10% w/w, for instance from 1% to 2% by weight of the formulation. It can however include up to as 10% w/w. In other embodiments it can include less than 5% w/w, or from 0.1% to 1% w/w of the formulation.

Gels for topical or transdermal administration of Å6 polypeptides or the peptide of SEQ ID NO:3 or capped variants can include, a mixture of volatile solvents, nonvolatile solvents, and water. The volatile solvent component of the buffered solvent system can include lower (C1-C6) alkyl alcohols, lower alkyl glycols and lower glycol polymers. In particular embodiments, the volatile solvent is ethanol. The volatile solvent component can act as a penetration enhancer, while also producing a cooling effect on the skin as it evaporates. The nonvolatile solvent portion of the buffered solvent system is selected from lower alkylene glycols and lower glycol polymers. In particular embodiments, propylene glycol is used. The nonvolatile solvent slows the evaporation of the volatile solvent and reduces the vapor pressure of the buffered solvent system. The amount of this nonvolatile solvent component, as with the volatile solvent, can be determined by the particular Å6 polypeptide or SEQ ID NO:3 or capped variant being used. The buffer component of the buffered solvent system can be selected from any buffer commonly used in the art; preferably, water is used. In some embodiments, the ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semi-synthetic cellulose derivatives (such as hydroxypropylmethylcellulose) and synthetic polymers, and cosmetic agents.

Lotions include those suitable for application to the skin or eye. An eye lotion can include a sterile aqueous solution optionally containing a bactericide and can be prepared by methods similar to those for the preparation of drops. Lotions or liniments for application to the skin can also include an agent to hasten drying and to cool the skin, such as an alcohol or acetone, and/or a moisturizer such as glycerol or an oil such as castor oil or arachis oil.

Creams, ointments or pastes are semi-solid formulations of the active ingredient for external application. They can be made by mixing the active ingredient in finely-divided or powdered form, alone or in solution or suspension in an aqueous or non-aqueous fluid, with the aid of suitable machinery, with a greasy or non-greasy base. The base can include hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation can incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops can include sterile aqueous or oily solutions or suspensions and can be prepared by dissolving the active ingredient in a suitable aqueous solution of a bactericidal and/or fungicidal agent and/or any other suitable preservative, and optionally include a surface active agent (surfactant). The resulting solution can then be clarified by filtration, transferred to a suitable container which is then sealed and sterilized by autoclaving or maintaining at 98-100° C. for half an hour. Alternatively, the solution can be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles including the active ingredient in a basis such as gelatin and glycerin or sucrose and acacia.

For administration by inhalation the Å6 polypeptides or the peptide of SEQ ID NO:3 or capped variants are conveniently delivered from an insufflator, nebulizer pressurized packs or other convenient means of delivering an aerosol spray. Pressurized packs can include a suitable propellant such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Alternatively, for administration by inhalation or insufflation, the Å6 polypeptides or the peptide of SEQ ID NO:3 or capped variants can take the form of a dry powder composition, for example a powder mix of the compound and a suitable powder base such as lactose or starch. The powder composition can be presented in unit dosage form, in for example, capsules, cartridges, gelatin or blister packs from which the powder may be administered with the aid of an inhaler or insufflator.

In some embodiments, unit dosage formulations are those containing an effective dose, as described above, or an appropriate fraction thereof, of the active ingredient.

It should be understood that in addition to the ingredients particularly mentioned above, the formulations of this invention can include other agents conventional in the art having regard to the type of formulation in question, for example those suitable for oral administration may include flavoring agents.

The an Å6 polypeptides or the peptide of SEQ ID NO:3 or capped variants used in the methods of the invention may be prepared using recombinant DNA technology. However, given their length, they are preferably prepared using solid-phase synthesis, such as that generally described by Merrifield, *J. Amer. Chem. Soc.*, 85:2149-2154 (1963), although other equivalent chemical syntheses known in the art are also useful. Solid-phase peptide synthesis may be initiated from the C-terminus of the peptide by coupling a protected alpha-amino acid to a suitable resin. Such a starting material can be prepared by attaching an alpha-amino-protected amino acid by an ester linkage to a chloromethylated resin or to a hydroxymethyl resin, or by an amide bond to a BHA resin or MBHA resin.

The preparation of the hydroxymethyl resin is described by Bodansky et al., (1966). Chloromethylated resins are commercially available from BioRad Laboratories, Richmond, Calif. and from Lab. Systems, Inc. The preparation of such a resin is described by Stewart et al., (1969). BHA and MBHA resin supports are commercially available and are generally used only when the desired polypeptide being synthesized has an unsubstituted amide at the C-terminus.

The amino acids can be coupled to the growing peptide chain using techniques well known in the art for the formation of peptide bonds. For example, one method involves converting the amino acid to a derivative that will render the carboxyl group of the amino acid more susceptible to reaction with the free N-terminal amino group of the growing peptide chain. Specifically, the C-terminal of the protected amino acid can be converted to a mixed anhydride by the reaction of the C-terminal with ethyl chloroformate, phenyl chloroformate, sec-butyl chloroformate, isobutyl chloroformate, or pivaloyl chloride or the like acid chlorides. Alternatively, the C-terminal of the amino acid can be converted to an active ester, such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole. Another coupling method involves the use of a suitable coupling agent, such as N,N'-dicyclohexylcarbodiimide or N,N'-diisopropylcarbodiimide. Other appropriate coupling agents, apparent to those skilled in the art, are disclosed in Gross et al. (1979), which is hereby incorporated by reference.

The alpha-amino group of each amino acid employed in the peptide synthesis can be protected during the coupling reaction to prevent side reactions involving their active alpha-amino function. Certain amino acids contain reactive side-chain functional groups (e.g., sulfhydryl, amino, carboxyl, and hydroxyl) and such functional groups can also be protected with suitable protecting groups to prevent a chemical reaction from occurring at either (1) the alpha-amino group site or (2) a reactive side chain site during both the initial and subsequent coupling steps.

In the selection of a particular protecting group to be used in synthesizing the peptides, the following general rules are typically followed. Specifically, an alpha-amino protecting group (1) should render the alpha-amino function inert under the conditions employed in the coupling reaction, (2) should be readily removable after the coupling reaction under conditions that will not remove side-chain protecting groups and will not alter the structure of the peptide fragment, and (3) should substantially reduce the possibility of racemization upon activation, immediately prior to coupling.

On the other hand, a side-chain protecting group (1) should render the side chain functional group inert under the conditions employed in the coupling reaction, (2) should be stable under the conditions employed in removing the alpha-amino protecting group, and (3) should be readily removable from the desired fully-assembled peptide under reaction conditions that will not alter the structure of the peptide chain.

It will be apparent to those skilled in the art that the protecting groups known to be useful for peptide synthesis vary in reactivity with the agents employed for their removal. For example, certain protecting groups, such as triphenylmethyl and 2-(p-biphenyl)isopropyloxycarbonyl, are very labile and can be cleaved under mild acid conditions. Other protecting groups, such as t-butyloxycarbonyl (BOC), t-amyloxycarbonyl, adamantyl-oxycarbonyl, and p-methoxybenzyloxycarbonyl, are less labile and require moderately strong acids for their removal, such as trifluoroacetic, hydrochloric, or boron trifluoride in acetic acid. Still other protecting groups, such as benzyloxycarbonyl (CBZ or Z), halobenzyloxycarbonyl, p-nitrobenzyloxycarbonyl cycloalkyloxycarbonyl, and isopropyloxycarbonyl, are even less labile and require even stronger acids, such as hydrogen fluoride, hydrogen bromide, or boron trifluoroacetate in trifluoroacetic acid, for their removal. Suitable protecting groups, known in the art are described in Gross et al. (1981).

Among the classes of amino acid protecting groups useful for protecting the alpha-amino group or for protecting a side chain group are included the following. (1) For an alpha-amino group, three typical classes of protecting groups are: (a) aromatic urethane-type protecting groups, such as fluorenylmethyloxycarbonyl (FMOC), CBZ, and substituted CBZ, such as, p-chlorobenzyloxycarbonyl, p-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type protecting groups, such as BOC, t-amyloxycarbonyl, isopropyloxycarbonyl, 2-(p-biphenyl)isopropyloxycarbonyl, allyloxycarbonyl and the like; and (c) cycloalkyl urethane-type protecting groups, such as cyclopentyloxycarbonyl, adamantyloxycarbonyl, and cyclohexyloxycarbonyl.

In some embodiments, the alpha-amino protecting groups are BOC and FMOC. (2) For the side chain amino group present in Lys, protection may be by any of the groups mentioned above in (1) such as BOC, 2-chlorobenzyloxycarbonyl and the like. (3) For the guanidino group of Arg, protection may be provided by nitro, tosyl, CBZ, adamantyloxycarbonyl, 2,2,5,7,8-pentamethylchroman-6-sulfonyl, 2,3,6-trimethyl-4-methoxyphenylsulfonyl, or BOC groups. (4) For the hydroxyl group of Ser or Thr, protection may be, for example, by t-butyl; benzyl (BZL); or substituted BZL, such as p-methoxybenzyl, p-nitrobenzyl, p-chlorobenzyl, o-chlorobenzyl, and 2,6-dichlorobenzyl. (5) For the carboxyl group of Asp or Glu, protection may be, for example, by esterification using such groups as BZL, t-butyl, cyclohexyl, cyclopentyl, and the like. (6) For the imidazole nitrogen of His, the benzyloxymethyl (BOM) or tosyl moiety is suitably employed as a protecting group. (7) For the phenolic hydroxyl group of Tyr, a protecting group such as tetrahydropyranyl, tert-butyl, trityl, BZL, chlorobenzyl, 4-bromobenzyl, and 2,6-dichlorobenzyl are suitably employed. The preferred protecting group is bromobenzyloxycarbonyl. (8) For the side chain amino group of Asn or Gln, xanthyl (Xan) is preferably employed. (9) For Met, the amino acid is preferably left unprotected. (10) For the thio group of Cys, p-methoxybenzyl is typically employed.

The first C-terminal amino acid of the growing peptide chain, e.g., Glu, is typically protected at the alpha-amino position by an appropriately selected protecting group such as BOC. The BOC-Glu-(y-cyclohexyl)-OH can be first coupled to a benzylhydrylamine resin using isopropylcarbodiimide at about 25° C. for two hours with stirring or to a chloromethylated resin according to the procedure set forth in Horiki et al., (1978). Following the coupling of the BOC-protected amino acid to the resin support, the alpha-amino protecting group is usually removed, typically by using trifluoroacetic acid (TFA) in methylene chloride or TFA alone. The alpha-amino group de-protection reaction can occur over a wide range of temperatures, but is usually carried out at a temperature between about 0° C. and room temperature.

Other standard alpha-amino group de-protecting reagents, such as HCl in dioxane, and conditions for the removal of specific alpha-amino protecting groups are within the skill of those working in the art, such as those described in Lubke et al., (1975), which is hereby incorporated by reference. Following the removal of the alpha-amino protecting group, the unprotected alpha-amino group, generally still side-chain protected, can be coupled in a stepwise manner in the intended sequence.

An alternative to the stepwise approach is the fragment condensation method in which pre-formed peptides of short length, each representing part of the desired sequence, are coupled to a growing chain of amino acids bound to a solid phase support. For this stepwise approach, a particularly suitable coupling reagent is N,N'-dicyclohexylcarbodiimide or diisopropylcarbodiimide. Also, for the fragment approach, the selection of the coupling reagent, as well as the choice of the fragmentation pattern needed to couple fragments of the desired nature and size are important for success and are known to those skilled in the art.

Each protected amino acid or amino acid sequence is usually introduced into the solid-phase reactor in amounts in excess of stoichiometric quantities, and the coupling is suitably carried out in an organic solvent, such as dimethylformamide (DMF), $CH_2Cl_2$ or mixtures thereof. If incomplete coupling occurs, the coupling procedure is customarily repeated before removal of the N-amino protecting group in preparation for coupling to the next amino acid. Following the removal of the alpha-amino protecting group, the remaining alpha-amino and side-chain-protected amino acids can be coupled in a stepwise manner in the intended sequence. The success of the coupling reaction at each stage of the synthesis may be monitored. One method of monitoring the synthesis is by the ninhydrin reaction, as described by Kaiser et al., (1970). The coupling reactions can also be performed automatically using well-known commercial methods and devices, for example, a Beckman 990 Peptide Synthesizer.

Upon completion of the desired peptide sequence, the protected peptide can be cleaved from the resin support, and all protecting groups can be removed. The cleavage reaction and removal of the protecting groups is suitably accomplished concomitantly or consecutively with de-protection reactions. When the bond anchoring the peptide to the resin is an ester bond, it can be cleaved by any reagent that is capable of breaking an ester linkage and of penetrating the resin matrix. One especially useful method is by treatment with liquid anhydrous hydrogen fluoride. This reagent will usually not only cleave the peptide from the resin, but will also remove all acid-labile protecting groups and, thus, will directly provide the fully de-protected peptide. When additional protecting groups that are not acid-labile are present, additional de-protection steps can be carried out. These steps can be performed either before or after the hydrogen fluoride treatment described above, according to specific needs and circumstances.

When a chloromethylated resin is used, the hydrogen fluoride cleavage/de-protection treatment generally results in the formation of the free peptide acids. When a benzhydrylamine resin is used, the hydrogen fluoride treatment generally results in the free peptide amides. Reaction with hydrogen fluoride in the presence of anisole and dimethylsulfide at 0° C. for one hour will typically remove the side-chain protecting groups and, concomitantly, release the peptide from the resin.

When it is desired to cleave the peptide without removing protecting groups, the protected peptide-resin can be subjected to methanolysis, thus yielding a protected peptide in which the C-terminal carboxyl group is methylated. This methyl ester can be subsequently hydrolyzed under mild alkaline conditions to give the free C-terminal carboxyl group. The protecting groups on the peptide chain can then be removed by treatment with a strong acid, such as liquid hydrogen fluoride. A particularly useful technique for methanolysis is that of Moore et al., (1977), in which the protected peptide-resin is treated with methanol and potassium cyanide in the presence of a crown ether.

Other methods for cleaving a protected peptide from the resin when a chloromethylated resin is employed include (1) ammoniolysis and (2) hydrazinolysis. If desired, the resulting C-terminal amide or hydrazide can be hydrolyzed to the free C-terminal carboxyl moiety, and the protecting groups can be removed conventionally. The protecting group present on the N-terminal alpha-amino group may be removed either before, or after, the protected peptide is cleaved from the support. Purification of the peptides of the invention is typically achieved using chromatographic techniques, such as preparative HPLC (including reverse phase HPLC), gel permeation, ion exchange, partition chromatography, affinity chromatography (including monoclonal antibody columns), and the like, or other conventional techniques such as countercurrent distribution or the like.

In some embodiments, the invention provides peptides based on SEQ ID NO:1 in which one or more amino acid residues has been removed and a different residue inserted in its place for example, SEQ ID NO:3 or capped variant. For a detailed description of protein chemistry and structure, see Schulz et al., *Principles of Protein Structure*, Springer-Verlag, New York, N.Y. (1979) and Creighton, *Proteins: Structure and Molecular Principles*, W. H. Freeman & Co., San Francisco, Calif. (1984), which are hereby incorporated by reference. The types of substitutions which may be made in the peptide molecule of the present invention can be conservative substitutions and are defined herein as exchanges within one of the following groups: 1. Small aliphatic, non-polar or slightly polar residues: e.g., Ala, Ser, Thr, Gly; 2. Polar, negatively charged residues and their amides: e.g., Asp, Asn, Glu, Gin; 3. Polar, positively charged residues: e.g., His, Arg, Lys.

Pro, because of its unusual geometry, tightly constrains the peptide chain. Substantial changes in functional properties are made by selecting substitutions that are less conservative, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain. Most substitutions according to the present invention are those which do not produce radical changes in the characteristics of the peptide molecule. Even when it is difficult to predict the exact effect of a substitution in advance of doing so, one skilled in the art will appreciate that the effect can be evaluated by routine screening assays, preferably the biological assay described below. Modifications of peptide properties including redox or thermal stability, hydrophobicity, susceptibility to proteolytic degradation or the tendency to aggregate with carriers or into multimers are assayed by methods well known to the ordinarily skilled artisan.

In some embodiments, SEQ ID NO:1 or SEQ ID NO:3 or capped variant can be formulated as a peptidomimetic as known in the art including, but not limited to, peptide-like molecules that contain a constrained amino acid, a non-peptide component that mimics peptide secondary structure, or an amide bond isostere. A peptidomimetic that contains a constrained, non-naturally occurring amino acid can include, without limitation, an α-methylated amino acid; α,α-dialkylglycine or α-aminocycloalkane carboxylic acid; an $N^\alpha$—$C^\alpha$ cyclized amino acid; an $N^\alpha$-methylated amino acid; αβ- or γ-amino cycloalkane carboxylic acid; an α,β-unsaturated amino acid; a β,β-dimethyl or β-methyl amino acid; a β-substituted-2,3-methano amino acid; an N—$C^\delta$ or $C^\alpha$—$C^\delta$ cyclized amino acid; a substituted proline or another amino acid mimetic. A peptidomimetic that mimics peptide secondary structure can contain, without limitation, a nonpeptidic β-turn mimic; γ-turn mimic; mimic of β-sheet structure; or mimic of helical structure, each of which is well known in the art. As non-limiting examples, a peptidomimetic also can be a peptide-like molecule that contains an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., *Acta Crystallogr.* 35:2331 (1979)). This structural depository is continually updated as new crystal structures are determined and can be screened for compounds having suitable shapes, for example, the same shape as a peptide of the invention, as well as potential geometrical and chemical complementarity to a target molecule. Where no crystal structure of a peptide of the invention is available, a structure can be generated using, for example, the program CONCORD (Rusinko et al., *J. Chem. Inf. Comput. Sci.* 29:251 (1989)). Another database, the Available Chemicals Directory (Molecular Design Limited, Informations Systems; San Leandro, Calif.), contains about 100,000 compounds that are commercially available and also can be searched to identify potential peptidomimetics of a peptide of the invention.

It is understood that modifications which do not substantially affect the activity of the various embodiments of this invention are also included within the definition of the invention provided herein. Accordingly, the following examples are intended to illustrate but not limit the present invention.

Example I

Immunoprecipitation of Å6CbioXL Polypeptides I

This Example shows immunoprecipitation of Å6CbioXL polypeptides including immunoblotting with anti-CD44.

Figure 2:
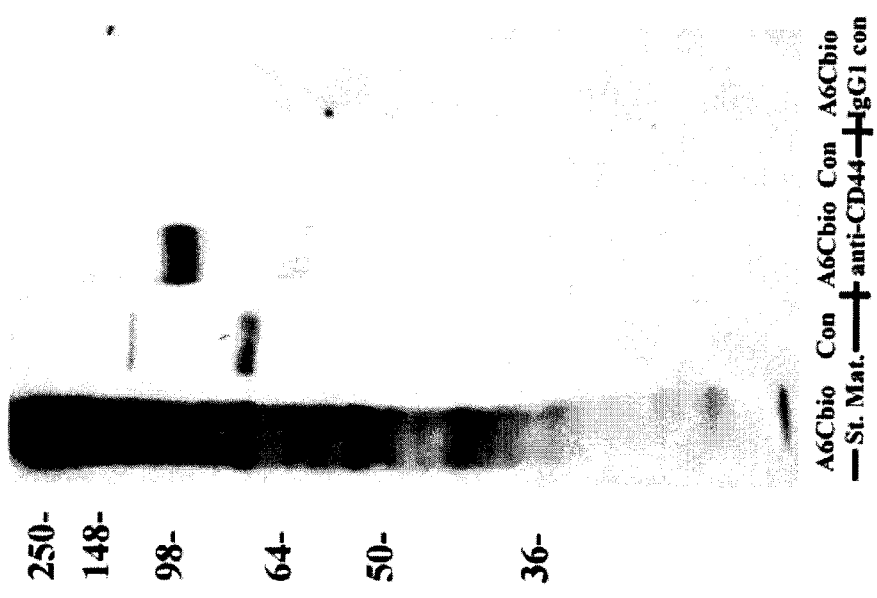
FIG. 2 shows immunoprecipitation of Å6CbioXL polypeptides using HRP-SA blotting confirming CD44 as a target.

In FIGS. 1 and 2 SKOV3 cells were incubated with or without 100 μM Å6Cbiotin (Å6CbioXL and ConXL, respectively) for 30 min at 4° C. The cells were then crosslinked with 5 mM bis(sulfosuccinimidyl) suberate (Sulfo-DSS or BS$^3$) for 30 min at 4° C. and Triton X-100 lysates generated. The lysates were pre-cleared by incubating with Protein A-agarose for 2 hr at room temperature. Aliquots representing 100 μg of the cleared lysates were then incubated overnight at room temperature with 20 μL of Protein A-agarose plus 2 μg of anti-Tenascin R (TnR; E-18, Santa Cruz Biotech.), anti-Tenascin C (TnC; 300-3, Santa Cruz Biotech.), anti-CD44 (DF1485, Santa Cruz Biotech.), anti-Plexin-A1 (PlA1; H-60, Santa Cruz Biotech.) or murine IgG1 (Sigma Chem. Co.). After washing 5 times with lysis buffer, the immunoprecipitated polypeptides were eluted from the Protein A-agarose by boiling in SDS-PAGE sample buffer. The eluted material and 2 μg aliquots of the starting material were then subjected to SDS-PAGE, transfer to PVDF membranes and blotting with chemiluminescent horseradish peroxidase (HRP)-conjugated streptavidin (HRP-SA). The results in FIG. 1 show that the Å6 peptide of SEQ ID NO:1 targets CD44 as indicated by the observed band in the "A" lane under CD44. FIG. 2 shows the same gel with intervening TnR, TnC, and PlA1 lanes cut out to facilitate comparison with the starting material (labeled "St. Mat.") and the molecular weight indications.

Example II

Immunoprecipitation of Å6CbioXL Polypeptides II

This Example shows further immunoblotting experiments confirming CD44 as the target of Å6

Figure 3:
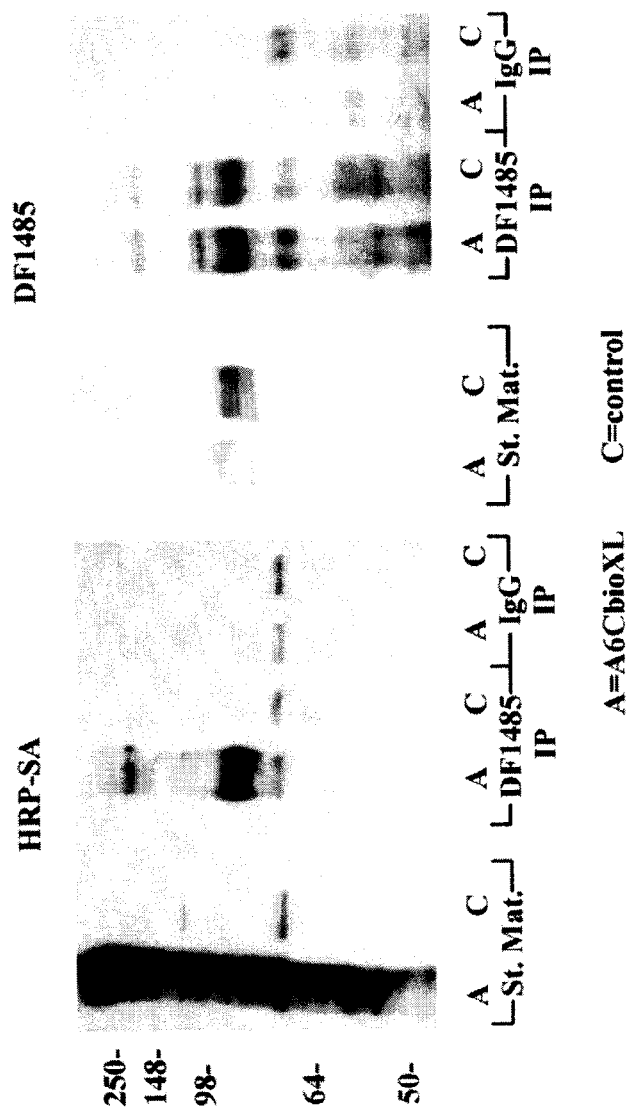
FIG. 3 shows further immunoprecipitation of Å6CbioXL polypeptides using HRP-SA blotting.

In FIG. 3 SKOV3 cells were incubated with or without 100 μM Å6Cbiotin (Å6CbioXL and control, respectively) for 30 minutes at 4° C. The cells were then crosslinked with 5 mM BS3 for 30 min at 4° C. Triton X-100 lysates generated and pre-cleared by incubating with Protein A-agarose for 2 hr at room temperature. Aliquots representing 100 μg of the cleared lysates were then incubated overnight at room temperature with 20 μL of Protein A-agarose plus 2 μg of anti-CD44 (DF1485, Santa Cruz Biotech) or murine IgG1 (Sigma Chem. Co.). After washing 5 times with lysis buffer, the immunoprecipitated polypeptides were eluted from the Protein A-agarose by boiling in SDS-PAGE sample buffer. The eluted material and 5 μg aliquots of the starting material were then subjected to SDS-PAGE, transfer to PVDF membranes and blotting with HRP-SA. The panel on the left of FIG. 3 shows probing with anti-SA, while the panel on the right show probing with anti-CD44. This experiment serves to confirm CD44 as the target of the Å6 peptide.

Example III

Å6 Inhibits the Binding of DF1485 Anti-CD44 to SKOV3 Cells

This Example shows FACs analysis of anti-CD44 (DF1485) Binding to SKOV3 Cells in the Presence of Å6.

Figure 4:
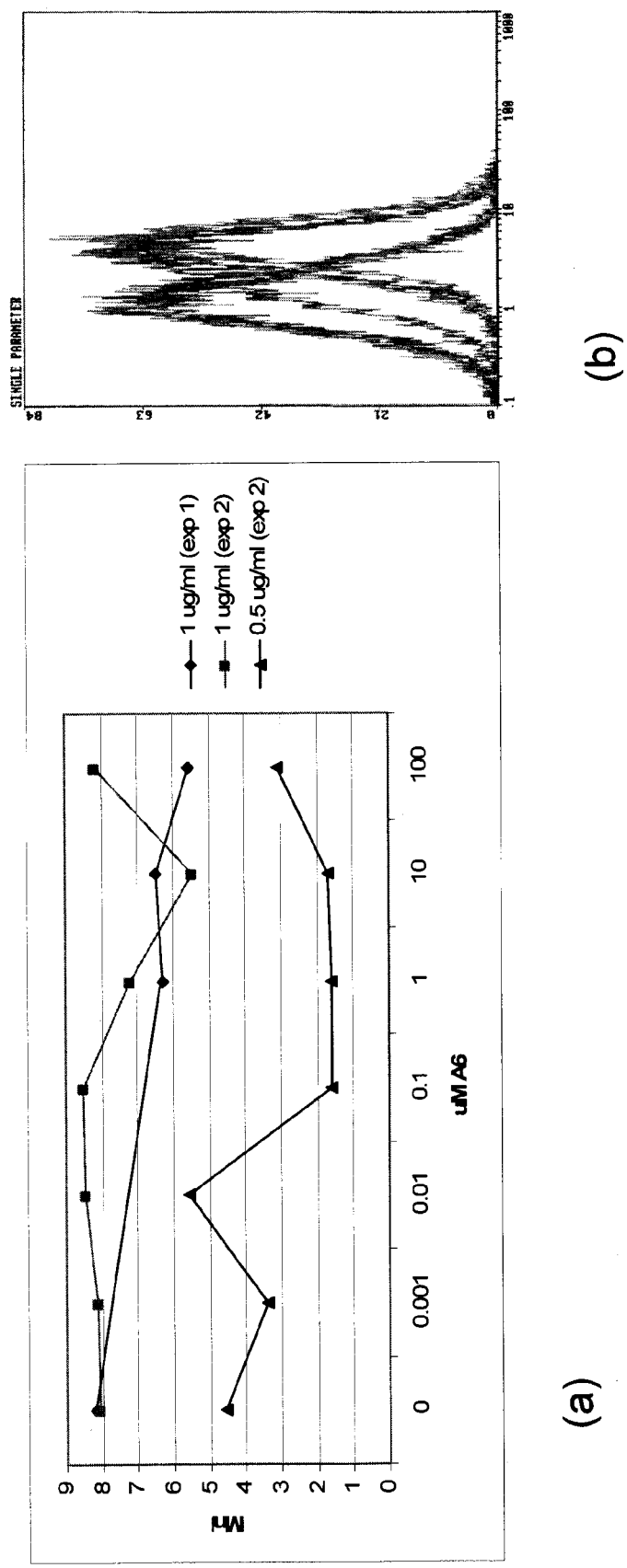
FIGS. 4a and 4b show FACs analysis of anti-CD44 (DF1485) binding to SKOV3 cells in the presence of the peptide of SEQ ID NO:1.
Figure 5:
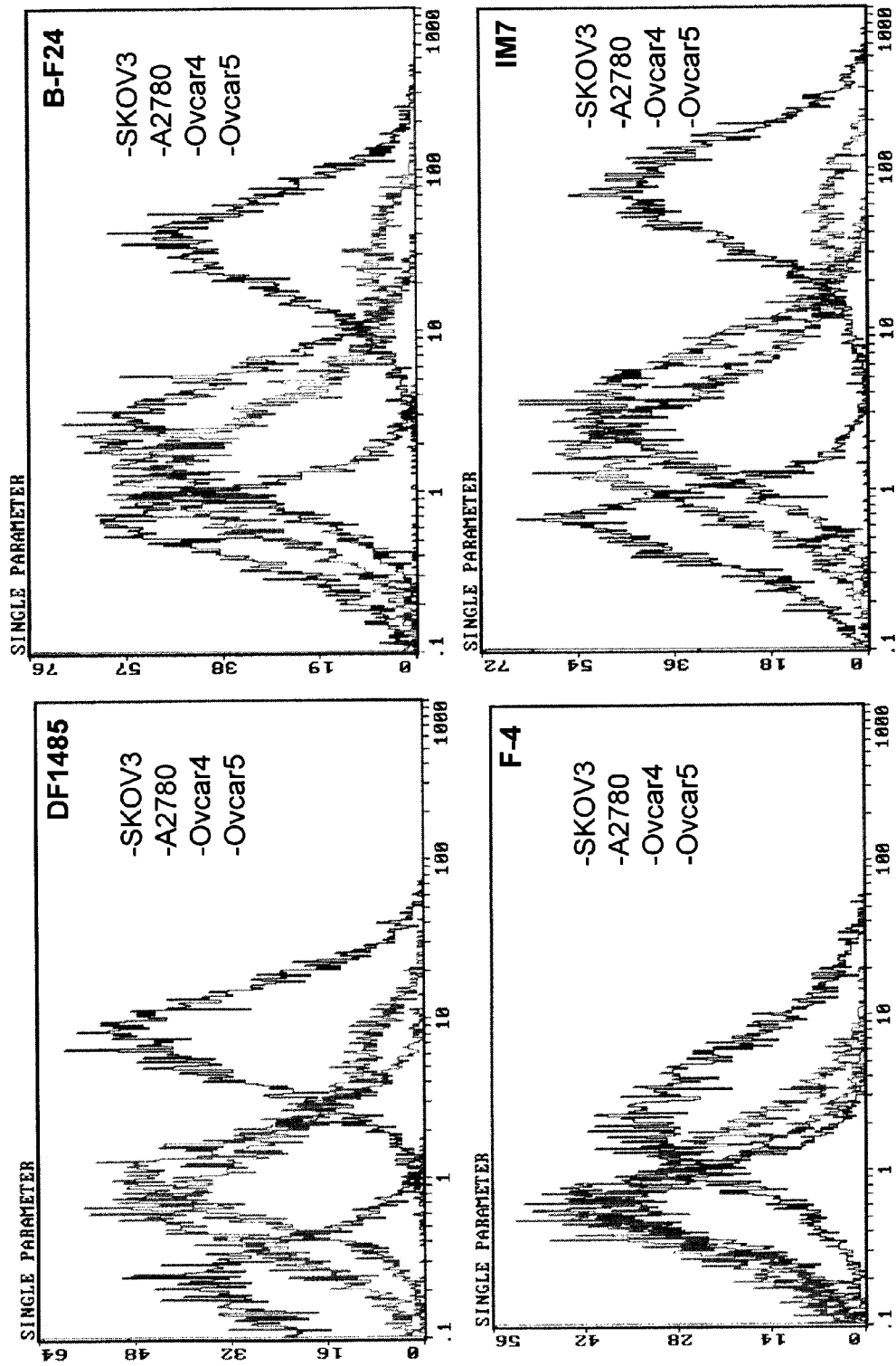
FIG. 5 shows CD44 expression in ovarian cancer lines using FACs analysis.
Figure 6:
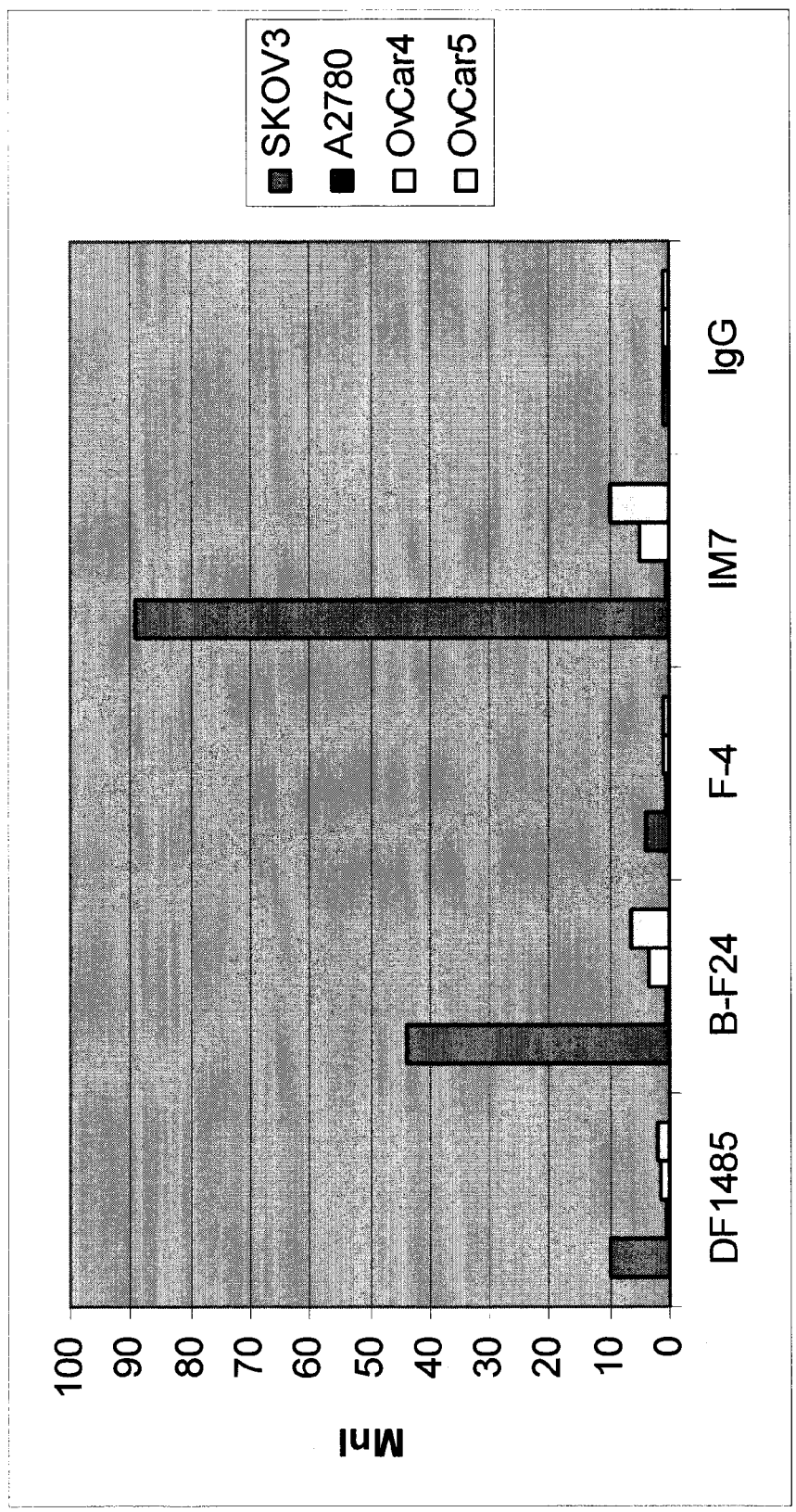
FIG. 6 shows a summary of FACs MnI values for CD44 expression in ovarian cancer lines.

In FIG. 4 SKOV3 cells were detached from their culture flasks by brief trypsinization, washed twice with DPBS and incubated on ice with the indicated concentrations of Å6 for 10 min (exp. 1) or 30 min (exp. 2). Anti-CD44 (DF1485; Santa Cruz Biotech.) or its isotype control were then added to final concentrations of 1 μg/ml (exp. 1) or 1 and 0.5 μg/ml (exp. 2) and the cells incubated for 1 hr on ice. The cells were washed once and incubated with FITC-conjugated donkey anti-mouse IgG (H+L) for 30 minutes on ice and then subjected to FACS analysis with a Beckman Coulter Epics XL-MCL cytofluorimeter. Data analysis was performed using the Coulter Epics software. Note: Data are presented as mean fluorescence intensities (MnI) obtained with the MnI of the negative control in each experiment adjusted to <0.5 during data collection. The results show Å6 inhibits the binding of DF1485 anti-CD44 to SKOV3 cells. Similar CD44 expression in ovarian cancer lines using different anti-CD44 antibodies is assessed in FIG. 5, for which the MnI values are summarized in FIG. 6. These results with other antibodies are representative of results seen in SKOV3 cells.

Binding of one of the anti-CD44 antibodies is inhibited by pre-incubation with Å6. Because the antibody does not recognize Å6 this result indicates that Å6 binding is causing steric hindrance, or Å6 binding is changing the conformation of CD44 so the antibody epitope is longer recognized. A change in CD44 conformation can alter susceptibility of CD44 to proteolysis.

Example IV

Anti-CD44 (DF1485) Immunoblot Analysis of Å6CbioXL Polypeptides and Å6-BSA

This Example shows DF1485 anti-CD44 does not recognize Å6 either as Å6Cbio crosslinked to SKOV3 polypeptides or coupled to BSA.

Figure 7:
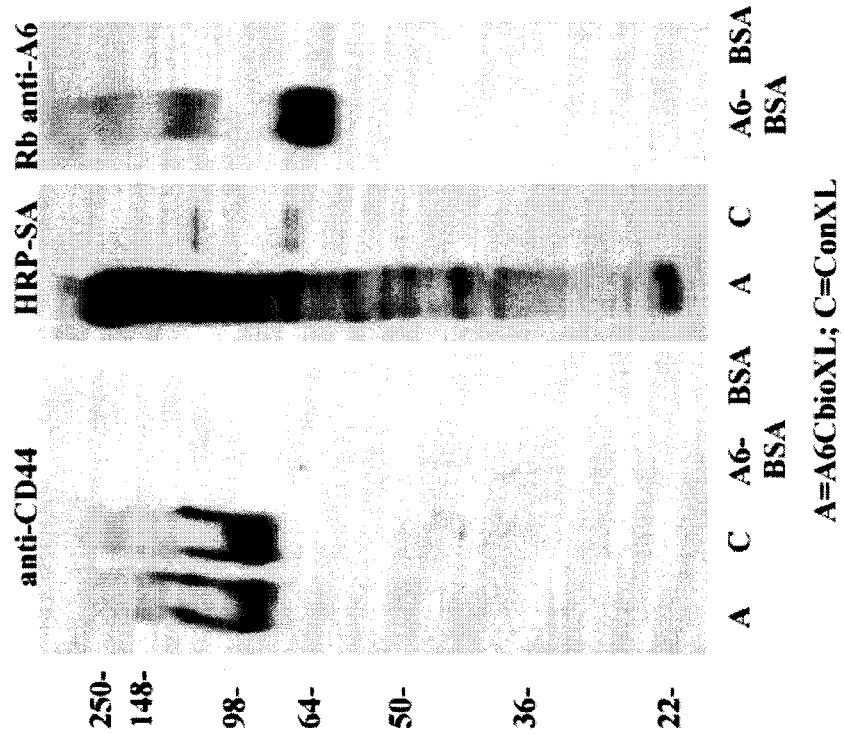
FIG. 7 shows anti-CD44 (DF1485) immunoblot analysis of Å6CbioXL polypeptides and Å6-BSA.

In FIG. 7 30 μg aliquots of Å6CbioXL and control (ConXL) SKOV3 lysates, as well as 2 μg aliquots of Å6-crosslinked BSA (Å6-BSA) and BSA, were subjected to immunoblot analysis using the DF1485 anti-CD44 antibody (Santa Cruz Biotech). The DF1485 blots were stained with HRP-conjugated sheep anti-Mouse IgG; heavy and light chain specific (GE Health Sciences). The rabbit anti-A6 blot was stained with HRP-conjugated donkey anti-rabbit IgG; heavy and light chain specific (Jackson Immunoresearch). Stained bands were visualized by the ECL-plus chemiluminescence reagent (GE Health Sciences) and exposure to Hyperfilm ECL film (GE). In panel 1, anti-CD44 produced bands in the Å6CbioXL (A lane) and control (C) lane. As indicated by the band intensity reduction, Å6CbioXL reduces the binding of anti-CD44 to CD44. No cross reactivity is observed with the Å6-BSA conjugate or BSA as shown in lanes 3 and 4 of panel 1. In addition, 2 μg aliquots of the Å6CbioXL and ConXL lysates were concurrently blotted with HRP-streptavidin to identify polypeptides labeled with Å6Cbio, and shown in panel 2. 2 μg of Å6-BSA and BSA were also blotted with Rb anti-Å6 to confirm the presence of Å6 on the Å6-BSA, as shown in the third panel of FIG. 7. The A6-BSA conjugate shows a band indicating the presence of Å6 on the conjugate. The control lane with BSA does not show this band.

Example V

Å6 ELISA Assessing the Ability of Anti-CD44 (DF1485) Ability to Bind Å6 or Inhibit Rb Anti-Å6-KLH Binding This Example shows DF1485 anti-CD44 does not bind Å6 directly nor inhibit the binding of Rb anti-Å6KLH in the Å6 ELISA.

Figure 8:
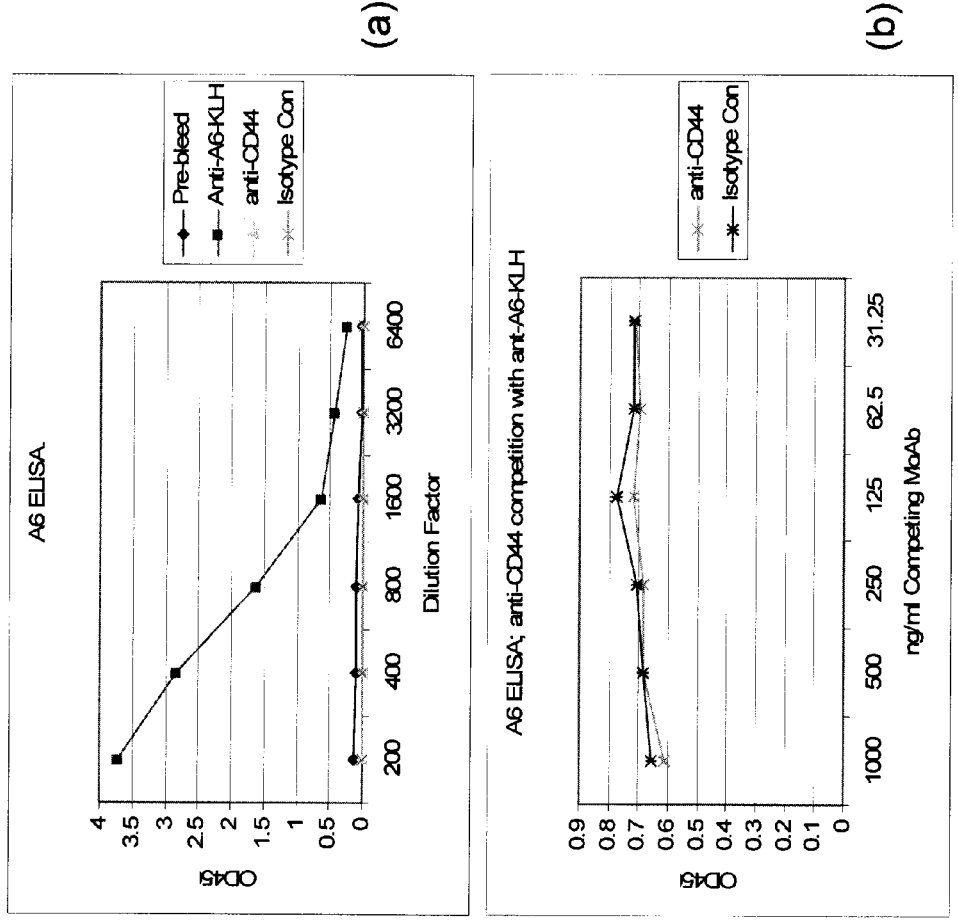
FIGS. 8a and 8b show Å6 ELISA assessing the ability of anti-CD44 (DF1485) ability to bind the peptide of SEQ ID NO:1 or inhibit Rb anti-Å6-KLH binding.

In FIG. 8a Å6 peptide (10 µg/ml in PBS; 100 µL/well) was absorbed onto microtiter wells overnight at 4° C. After blocking with 1% BSA for 1 hr at room temperature, the indicated dilutions of Rb anti-Å6-KLH, its pre-bleed control, anti-CD44 (DF1485) or its isotype control were added to duplicate wells and incubated for 1 hr at room temperature. Antibody binding was detected with 1/7,500 dilutions of HRP-conjugated donkey anti-Rb IgG (H+L; Jackson Imm. Research) or goat anti-mouse IgG (H+L; GE Health Sciences), followed by color development with TMB stabilized substrate (Invitrogen, Carlsbad, Calif.). FIG. 8a shows that anti-CD44 and its isotype control do not bind to the Å6 peptide. In contrast, anti-Å6-KLH shows dilution dependent optical density at 450 nm (OD450) demonstrating its binding to the Å6 peptide. Control with the pre-bleed also indicates the lack of pre-existing antibodies that recognize the Å6 peptide. In FIG. 8b the binding of Rb anti-Å6-KLH (1/1600 dil) in the presence of the indicated concentrations of DF1485 anti-CD44 or its isotype control was assessed as described above. Significantly, the binding of Rb anti-Å6-KLH was not competitively inhibited by DF1485 anti-CD44 or its isotype.

Example VI

CD44 Expression In Ovarian Cancer Lines

This Example shows CD44 expression in ovarian cancer lines using immunoblot analysis.

Figure 9:
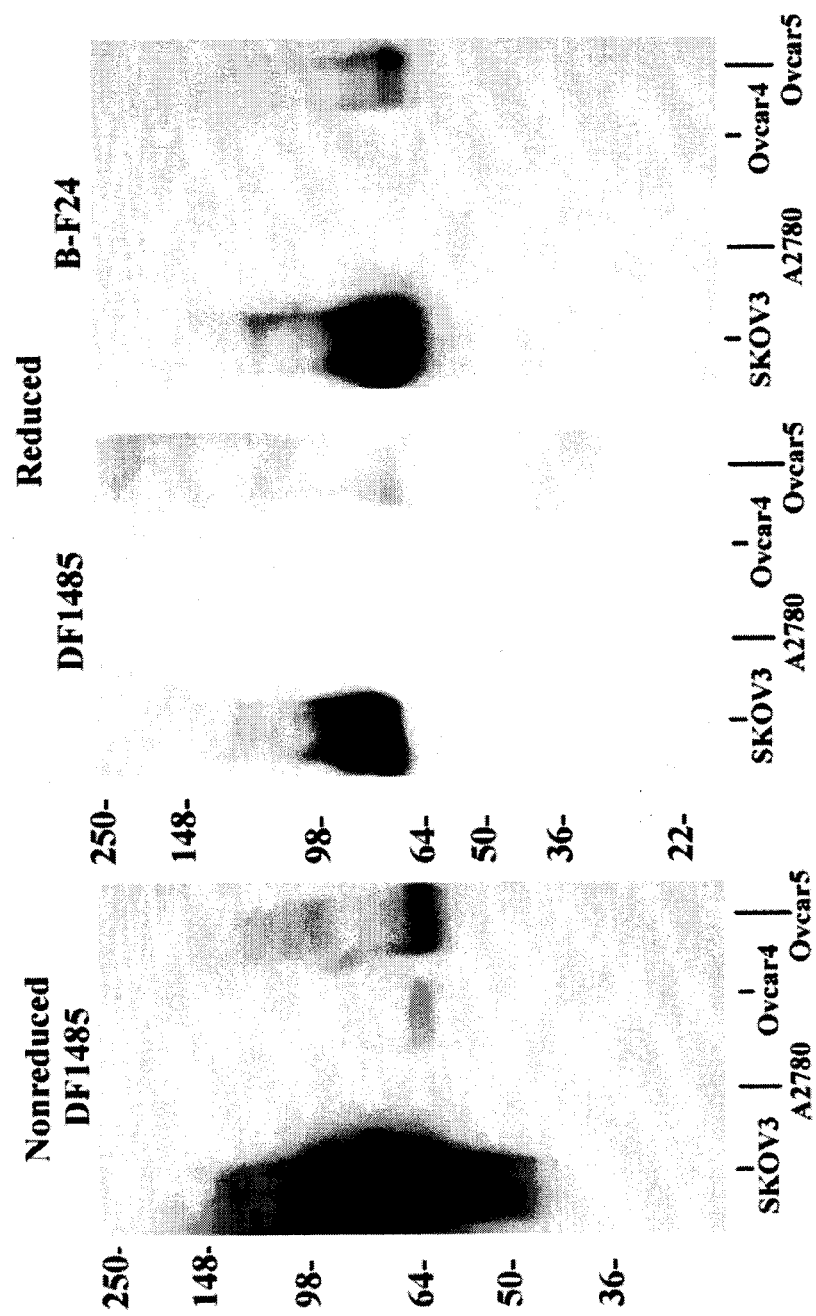
FIG. 9 shows CD44 expression in ovarian cancer lines using immunoblot analysis.

In FIG. 9 Triton X-100 lysates of confluent cultures of SKOV3, A2780, Ovcar4 and Ovcar5 cells were further solubilized in SDS-PAGE sample buffer in the absence (left panel) or presence (middle and right panels) of 5% beta-mercaptoethanol reducing agent. 30 µg aliquots were subjected to SDS-PAGE and immunoblot analysis with the anti-CD44 monoclonal antibodies DF1485 (left and middle panels) and B-F24 (right panel). Note, the band in the SKOV3 lane persists even under reducing conditions. These results show that SKOV3 cells show significantly higher CD44 expression than other ovarian cell lines.

Example VII

Effect of Å6 on the Chemotaxis of A2780 and SKOV3 Cells

This Example shows the effects of Å6 on chemotaxis in two different ovarian cancer cell lines.

Figure 10:
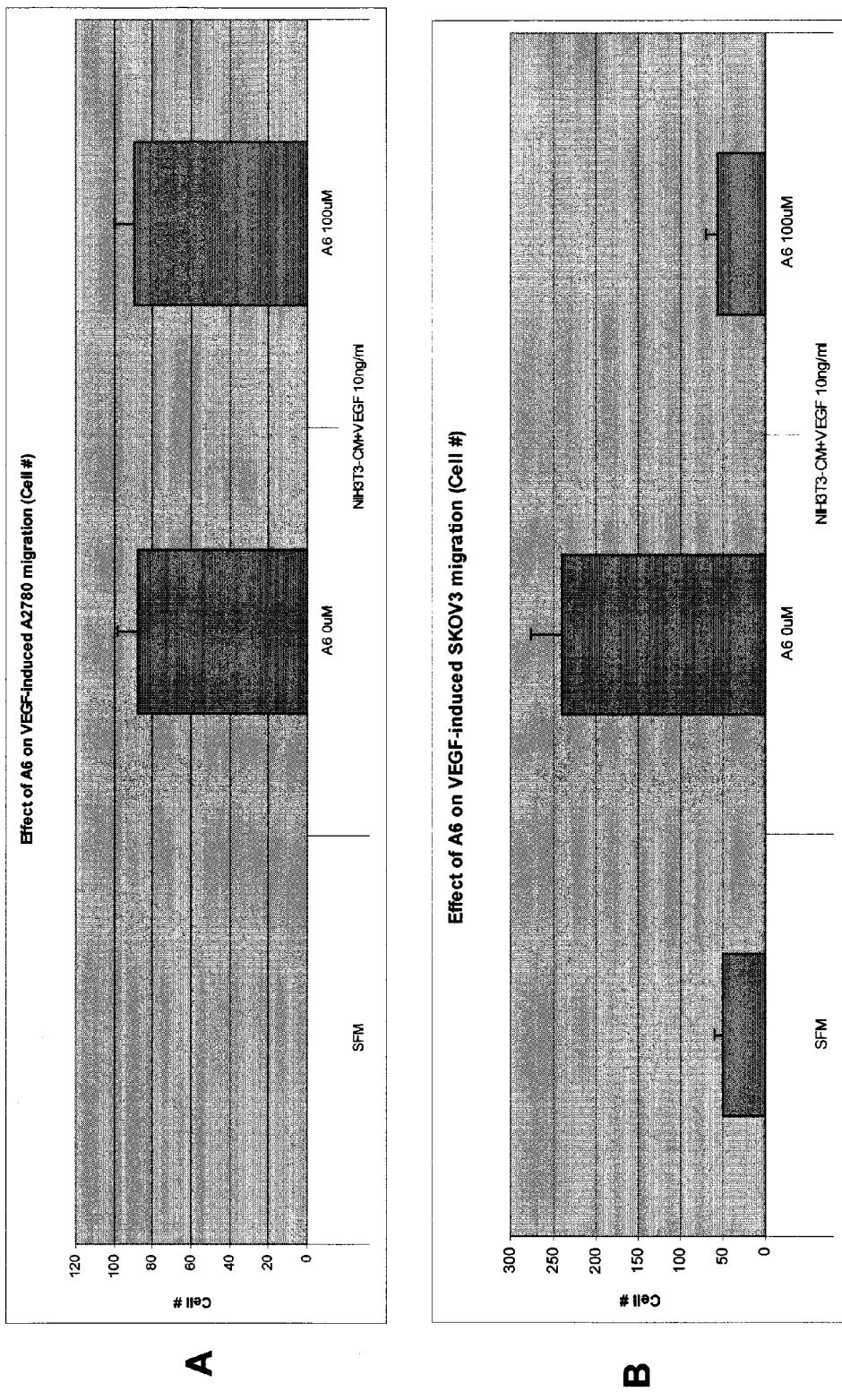
FIG. 10 shows the effect of the peptide of SEQ ID NO:1 on the chemotaxis of A2780 (10A) and SKOV3 (10B) cells.

A2780 (FIG. 10a) and SKOV3 (FIG. 10b) cells were incubated with the indicated concentrations of Å6 peptide for 30 min at 37° C. Aliquots representing 6,000 cells were placed on quadruplicate, CnI-coated filters (8 µm pores) in Boyden chambers and the cells allowed to migrate overnight in response to 10 ng/ml VEGF in NIH3T3-conditioned media containing the indicated concentrations of Å6. Upon completion of migration, the apical surfaces of the membranes were wiped clean and the migrating cells on the basal surface were stained with Geimsa stain and the cells present in representative fields of the membranes counted. Data represent the averages+/−standard deviations obtained from the replicate filters. FIG. 10a shows that migration of A2780 is essentially unaffected by the presence of the Å6 peptide. By contrast, FIG. 10b shows strong inhibition of SKOV3 migration in the presence of the Å6 peptide. This provides further confirmation that CD44 is the target for the Å6 peptide.

Example VIII

Adhesion of SKOV3 Cells to Hyaluronic Acid

This Example shows ovarian cancer cell line SKOV3 adhesion with hyaluronic acid.

Figure 11:
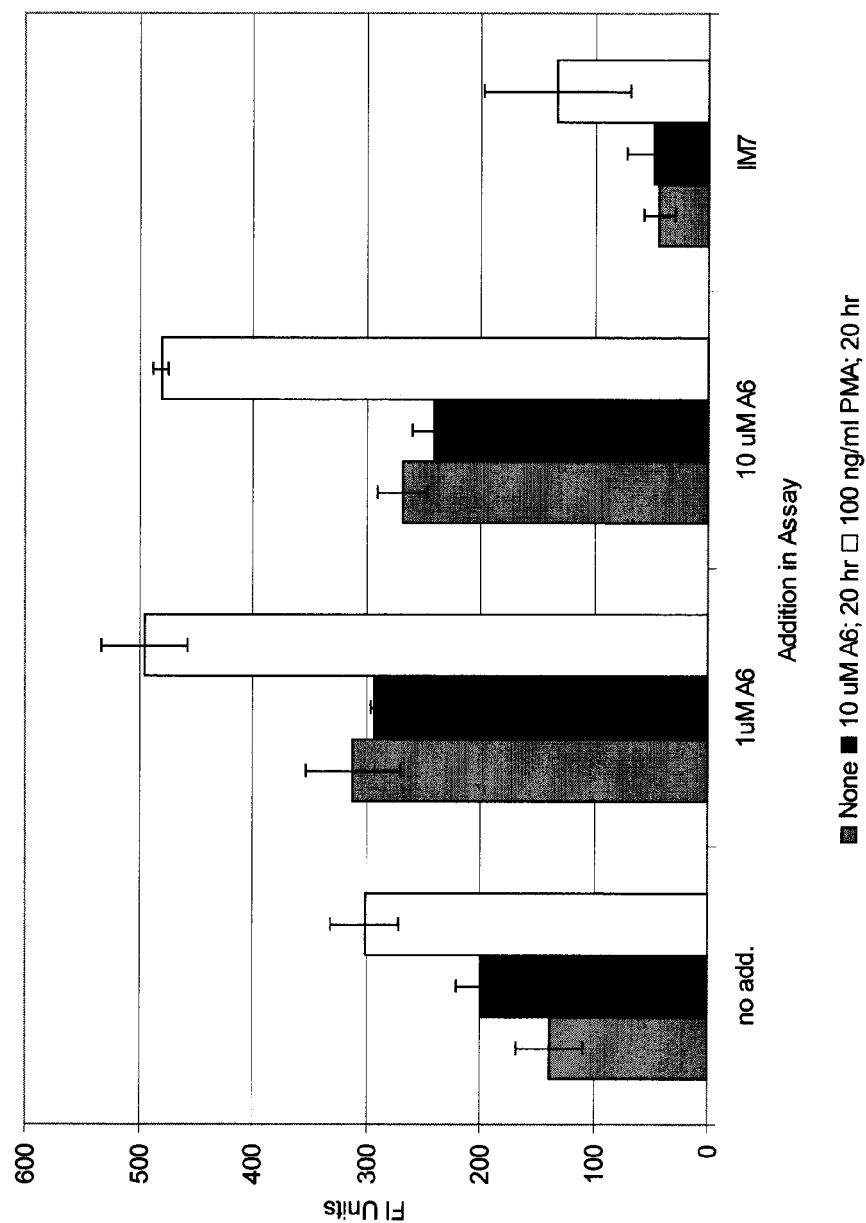
FIG. 11 shows the adhesion of SKOV3 cells to hyaluronic acid in the presence and absence of the peptide of SEQ ID NO:1.

In FIG. 11 SKOV3 cells were cultured overnight with or without 10 µM Å6 or 100 ng/ml PMA. The cells were then detached, washed and loaded with 20 µg/ml CFDA-SE for 30 min at 37° C. After washing, the cells were resuspended in PBS containing 10% FCS and triplicate aliquots representing 100,000 cells incubated for 30 min at room temperature with no additions, 1 or 10 uM Å6 or with 20 ng/ml IM7, a blocking anti-CD44 rat monoclonal antibody. The cells were then placed into microtiter wells that had been coated with 50 µL of 1 mg/mL HA overnight and blocked for 30 min with 10% FCS. The cells were allowed to adhere at room temperature for 30 minutes after which, the wells were decanted and washed 3 times. The fluorescence in each well was assessed (excit./emiss.: 460/536 nm) and the mean fluorescence values (+/standard deviation) of the triplicate determinations calculated. These results indicate that SKOV3 binding to HA is enhanced by the Å6 peptide, although there is little effect in a 10-fold increase in concentration of the Å6 peptide (middle two sets of graphs). The control experiment with IM7 (graphs on far right) indicates inhibition of SKOV3 binding to HA in the presence of this anti-CD44, which indicates a role for CD44 in binding HA. These results indicate that the Å6 peptide has a role in modulating the interaction between CD44 and HA.

Example IX

Adhesion of A2780 Cells to Hyaluronic Acid

This Example shows ovarian cancer cell line A2780 adhesion with hyaluronic acid.

Figure 12:
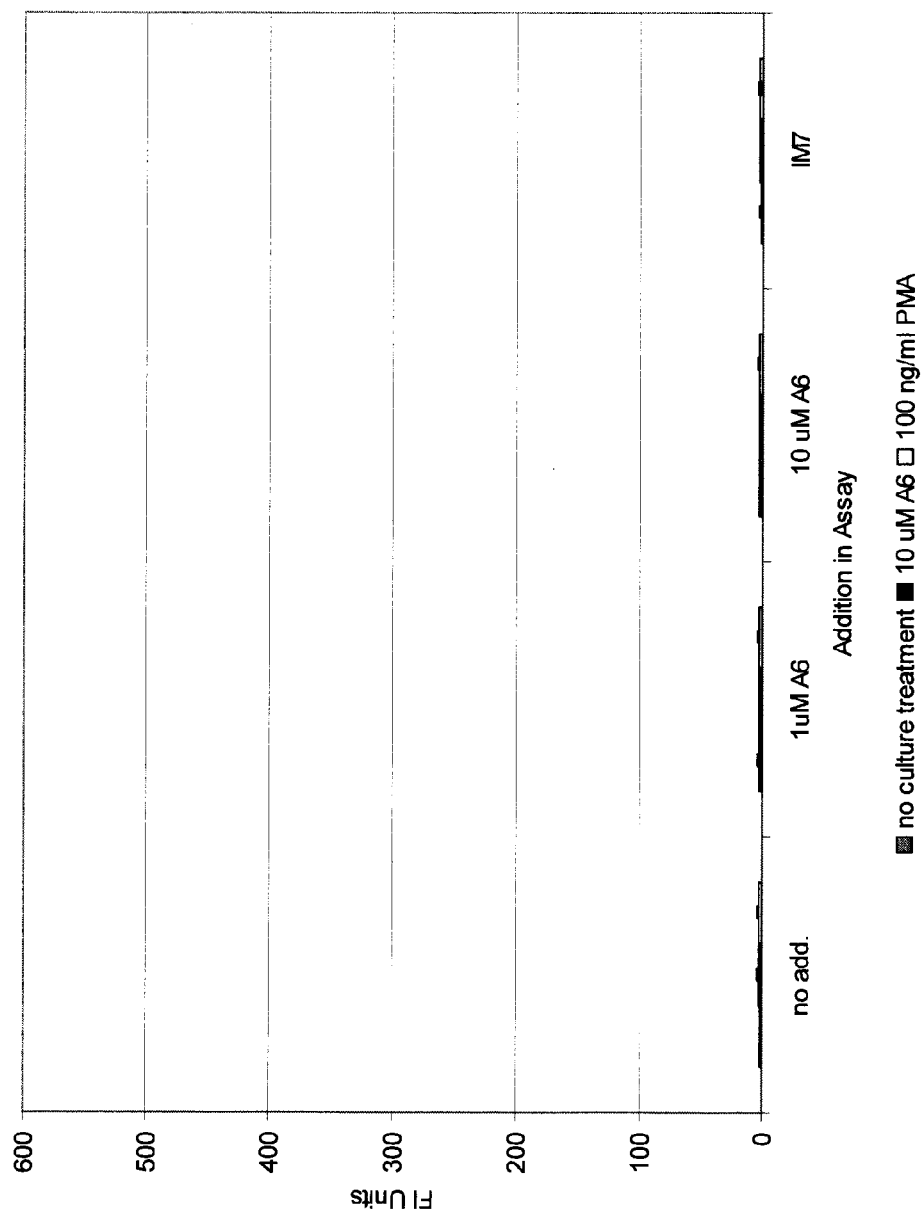
FIG. 12 shows the adhesion of A2780 cells to hyaluronic acid in the presence and absence of the peptide of SEQ ID NO:1.

In FIG. 12 A2780 cells were cultured overnight with or without 10 µM Å6 or 100 ng/ml PMA. The cells were then detached, washed and loaded with 20 µg/ml CFDA-SE for 30 min at 37° C. After washing, the cells were resuspended in PBS containing 10% FCS and triplicate aliquots representing 100,000 cells incubated for 30 min at room temperature with no additions, 1 or 10 µM Å6 or with 20 ng/ml IM7, a blocking anti-CD44 rat monoclonal antibody. The cells were then placed into microtiter wells that had been coated with 50 ul of 1 mg/ml HA overnight and blocked for 30 min with 10% FCS. The cells were allowed to adhere at room temperature for 30 min after which, the wells were decanted and washed 3 times. The fluorescence in each well was assessed (excit./emiss.: 460/536 nm) and the mean fluorescence values (+/standard deviation) of the triplicate determinations calculated. The results indicate that A2780 cells, which lack CD44, do not bind HA. Furthermore, the Å6 peptide does not substantially modulate the binding of this cell line to HA.

Example X

Dimerization of CD44 in Response to Culture with Å6

This Example shows that higher molecular weight bands are formed in SKOV3 cells cultured in the presence of Å6.

Figure 13:
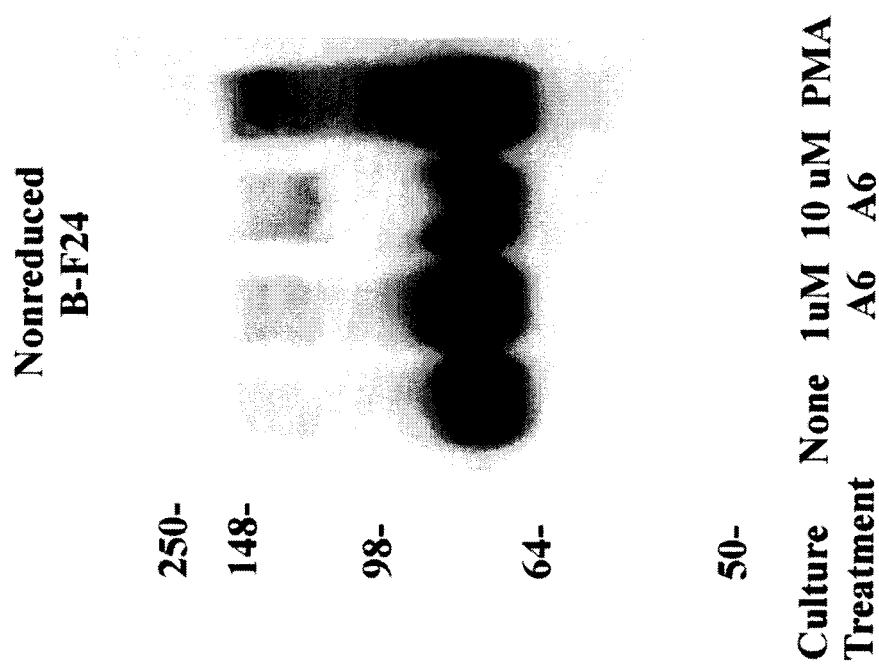
FIG. 13 shows an immunoblot analysis indicating the formation of higher molecular weight bands indicating CD44 dimerization in the presence of the peptide of SEQ ID NO:1.

In FIG. 13 SKOV3 cells were cultured for 20 hr with no additions, 1 or 10 µM Å6 or 100 ng/ml PMA. Triton X-100 lysates were generated and further solubilized in SDS-PAGE sample buffer under non-reducing conditions. Aliquots representing 7.5 µg of cellular protein were subjected to SDS-PAGE followed by immunoblot analysis with the anti-CD44 murine monoclonal B-F24. The presence of stained higher molecular weight bands can be indicative of CD44 dimers and/or oligomers.

Example XI

IM7 Binding to SKOV3 Cells

This Example shows IM7 binding to SKOV3 cells in the presence and absence of Å6.

Figure 14:
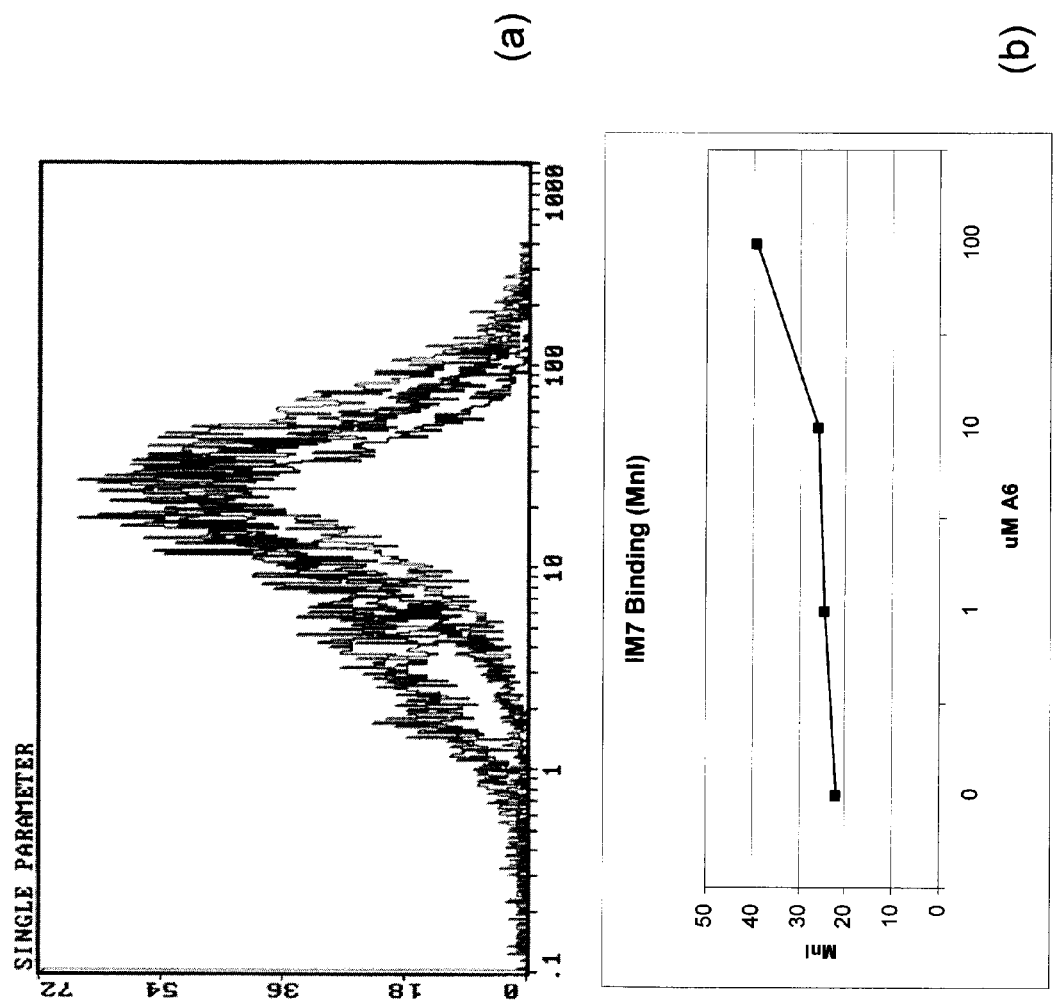
FIGS. 14a and 14b show IM7 binding to SKOV3 cells in the presence and absence of the peptide of SEQ ID NO:1.

In FIGS. 14a and 14b SKOV3 cells were incubated with the indicated concentrations of Å6 for 30 min at 4° C. IM7 (1 µg/ml) was then added and allowed to bind for 30 min at 4° C., after which the cells were washed and incubated with FITC-donkey anti-rat IgG for 30 min at 4° C. The cells were washed once and then subjected to FACs analysis. The results show an increase in antibody binding with increasing concentration of the Å6 peptide. This demonstrates that the Å6 peptide mediates binding to the CD44 specific antibody.

Example XII

Inhibition of Metastasis

This Example show the inhibition of metastasis in a melanoma lung metastasis model.

The B16 melanoma metastasis is well known in the art. A typical protocol for assessing the inhibitory effect of a compound on metastasis is described below. Such a protocol was followed to assess the effect of Å6 on metastasis.

Figure 15:
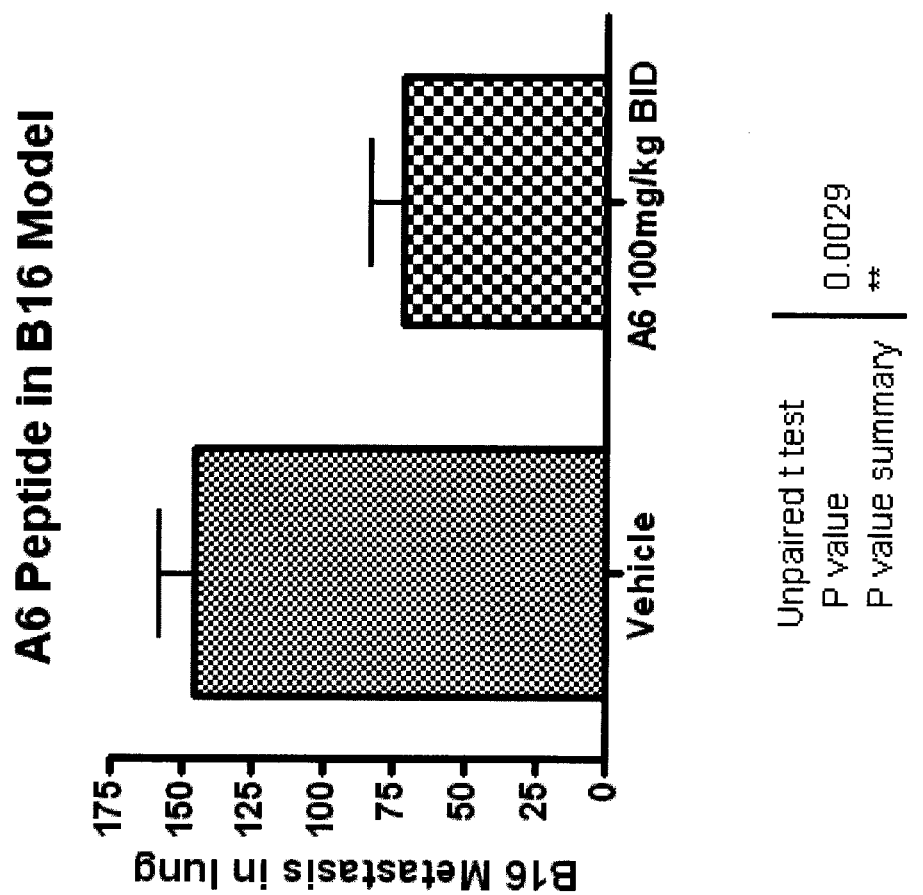
FIG. 15 shows the inhibition of metastasis in a melanoma lung metastasis model in the presence of Å6 or with vehicle alone.

Briefly, B16 melanoma cells can be cultured in RPMI-1640 with 10% fetal bovine serum at 37° C. in an atmosphere of 95% air and 5% $CO_2$. C57BL/6J mice of six to eight weeks can be purchased from commercial suppliers. For the lung metastasis model, about $1\times10^5$ melanoma cells suspended in 100 µl saline were injected in the tail vein in the presence or absence of Å6. The results are shown in FIG. 15. Administration of the Å6 peptide inhibited the lung metastasis by 50% or more.

Example XIII

NASAPPEE Peptide Inhibits SKOV3 Migration

This Example shows NASAPPEE peptide (SEQ ID NO:3) inhibited NIH3T3-CM/VEGF induced SKOV3 migration. The inhibition range was from 69 to 83%.

SKOV3 cells are harvested by trypsinization and washed once with RPMI–0.5% BSA. Next, the cells are re-suspended in RPMI+0.5% BSA @ 6E4/mL (6000 cells/100 µL). The peptide is pre-treated with 500 µL of cells added to 500 µL peptide NASAPPEE (2× concentration, final conc. at 100, 10, 1, 0.1, 0.01, 0.001 uM) and the mixture incubated 30 minutes at 37° C., under 5% $CO_2$. The Boyden chamber is assembled by: Placing in the bottom chambers: 220 µL of serum/BSA free DMEM or NIH3T3CM+10 ng/ml VEGF or NIH3T3CM+10 ng/ml VEGF+peptide. Place 8 µm filters on the top of the bottom chambers. The 8 µm filters are coated with 1 mg/ml collagen I at 4° C. overnight, washed with PBS twice, air dry before use. Add 200 µL of cells with or without peptide pretreatment to the top of Boyden chamber. Note that the peptide is in both top and bottom chambers. Cells migrate overnight at 37° C., under 5% CO2 in incubator. Next, Boyden chambers are disassembled the and filters collected. The cells on the filters after collection are treated with −20° C. methanol for 3 minutes at room temperature and stained with 30% Geimsa for 7 minutes at room temperature, and washed with water twice. The filters are mounted on slides, air dried and the cells counted.

Figure 18:
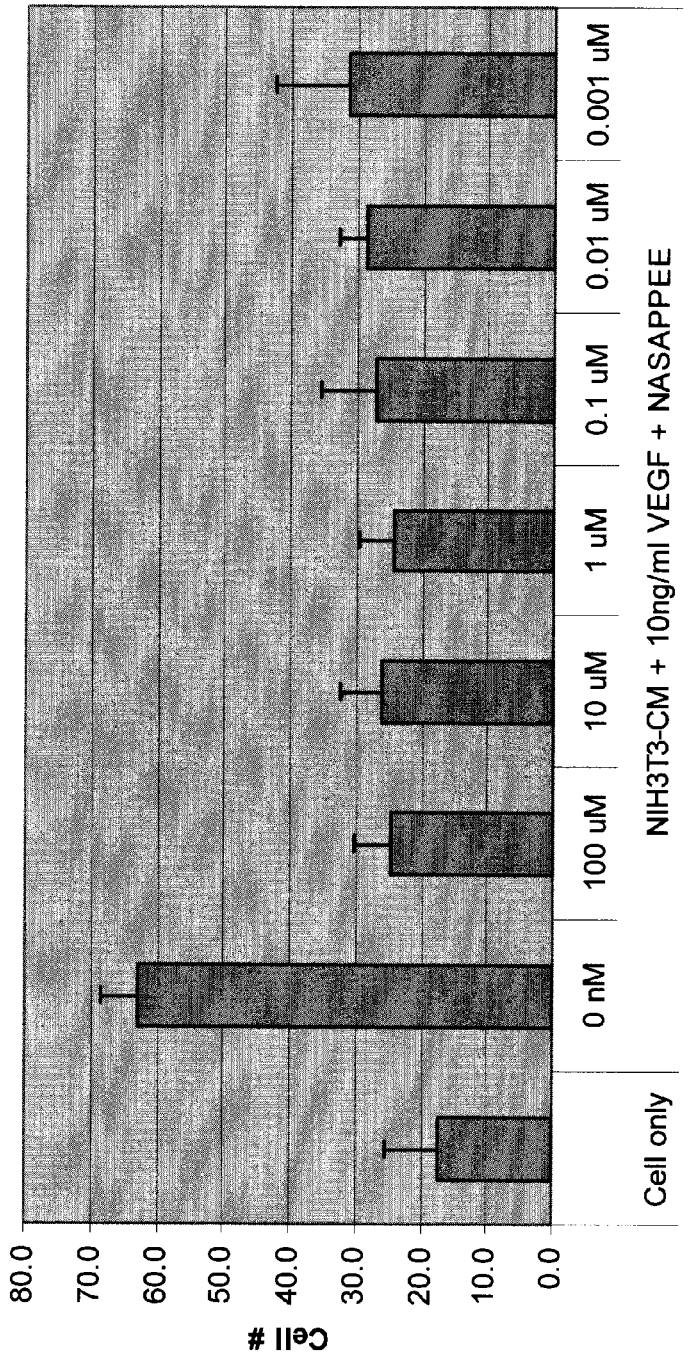
FIG. 18 shows the inhibition of SKOV3 migration in the presence of the peptide of SEQ ID NO:3.

Cell numbers were obtained by counting the cells in four fields of filters using a 40× objective. The cells migrating into the bottom chambers were also counted as follows: a) 200 µL fluid in the bottom chamber was transferred to a well of 96-well plate; b) The plate was centrifuged at 1200 rpm for 5 minutes; c) 180 µL of supernatant was removed; d) The cell pellet was resuspended with the remaining 20 µL fluid and the cells counted using a hemocytometer. The results are shown in FIG. 18. Cell migration inhibition is achieved with comparable effectiveness between 100 µM and 1 nM concentrations. This compares favorably to the Å6 peptide which is effective between 5 µM and 100 nM.

Example XIV

Intracellular Signaling Response to Å6

This Example shows the effects of HA and the Å6 peptide on the state of phosphorylation of FAK, ERK1/2, MEK, and PKCalpha in SKOV3 cells.

Å6 Peptide

The capped Å6 peptide (acetyl-Lys-Pro-Ser-Ser-Pro-Pro-Glu-Glu-$NH_2$) was synthesized, purified and prepared as a 100 mg/ml solution in sterile phosphate buffered saline by Altheas Technologies, Incorporated.

Cell Culture

All culture reagents were obtained from Cellgro Mediatech, Inc. (Manassas, Vt.). SKOV3 cells were cultured in McCoy's 5A medium and A2780 cells were cultured in RPMI 1640. All media were supplemented with 10% fetal bovine sera (FBS), 1000 U/ml penicillin, 100 ug/ml streptomycin and 4 mM 1-glutamine. Detachment for experiments and/or sub-culture was performed by brief trypsinization in 0.25% Trypsin, 2.21 mM EDTA in Hank's buffered saline solution.

Pre-Treatment with Hyaluronic Acid; Treatment with A6

Cells were detached from their culture vessels by brief trypsinization, suspended in complete media and centrifuged at 250×g for 10 min at room temperature. The cell pellets were suspended in Dulbeco's phosphate buffered saline (DPBS) and re-centrifuged for a total of three washes. The cells were then re-suspended at 3.33E5/ml in 24 ml of either RPMI containing 0.5% BSA (Sigma Chem. Co. #A0336) (RPMI/BSA) or the conditioned media of growing NIH3T3 fibroblasts (10% FBS in DMEM) supplemented with 10 ng/ml vascular endothelial growth factor (VEGF) (CMN). The cells were then treated with or without 100 ug/ml soluble hyaluronic acid (HA; human umbilical, Calbiochem #385902) for 30 min at 37° C. under 5% CO2. Aliquots representing 2E6 cells were then plated into 10 cm culture dishes and A6 added to yield final concentrations of 0, 10, 100 and 1000 nM. The cells were cultured overnight (18 hr) at 37° C. under 5% CO2.

Lysate Generation.

After 18 hr of treatment, the media were aspirated from the 10 cm dishes and saved. The plates were washed 3 times with 4 ml of ice-cold DPBS which were pooled with the reserved non-adherent cells. The non-adherent cells were centrifuged at 250×g for 10 min at 4° C., washed twice with cold DPBS, drained and lysed in 50 ul of cold RIPA buffer (ThermoScientific #89901) containing cocktails of broad spectrum phosphatase inhibitors (Calbiochem #524625; used at 2× final concentration) and protease inhibitors (Sigma #P8340) (RIPA/inh.). The 10 cm dishes were drained of remaining wash and the adherent cells lysed by scraping in 200 µL of cold RIPA/inh. For each test condition, the lysates of the non-adherent and adherent populations were combined, vortexed and then centrifuged at 14,000 rpm at 4° C. for 20 min. Aliquots of the cleared lysates were frozen at −80° C. immediately. A small aliquot was reserved for total protein analysis using a BCA Protein Assay Kit (Calbiochem #71285-3).

Immunoblot Analysis.

Samples representing 20 µg of total protein of each lysate were solubilized in the presence of 50 mM Tris pH 6.8, 10% glycerol, 2% SDS and 100 mM DTT for 5 min at 95° C. and then loaded onto 10-20% acrylamide gels (BioRad #345-0044, Tris-HCl, 1 mm, 26 well, 15 µL/well). Electrophoresis was performed using Laemli electrophoresis buffer (0.1% SDS, 25 mM Tris, 192 mM glycine) at 200 V, constant voltage, for one hour. Upon completion of electrophoresis, the proteins were transferred to Immun-Blot PVDF membranes (BioRad #162-0238) in ice-cold 20% methanol in 25 mM Tris, 192 mM glycine for 2 hr at 0.5 Amps, constant current/blotting apparatus. The membranes were then cut vertically between molecular weight markers and in half at the 64 kDa marker to generate pieces for screening of higher molecular weight proteins (e.g., FAK) and lower molecular weight proteins (e.g., MEK and GAPDH). The blots were then blocked for a minimum of 4 hrs at room temperature in 3% bovine serum albumin (Sigma A0336) in 50 mM Tris, pH 7.4, 145 mM NaCl, 0.05% Tween-20 (TTBS) containing 0.05% sodium azide.

The blots were then stained for 4 hr at room temperature in dilutions of primary antibody in 3% BSA in TTBS with azide (Table A).

TABLE A

Primary Antibodies

| Antibody | Source | Catalog # | Dilution |
|---|---|---|---|
| Rabbit anti-FAK | Cell Signaling Tech. | 3285 | 1/500 |
| Rabbit anti-pFAK (Y397) | Cell Signaling Tech. | 3283 | 1/1000 |
| Rabbit anti-pFAK (Y576/577) | Cell Signaling Tech. | 3281 | 1/1000 |
| Rabbit anti-pFAK (Y925) | Cell Signaling Tech. | 3284 | 1/500 |
| Rabbit anti-MEK 1/2 (47E6 monoclonal) | Cell Signaling Tech. | 9126 | 1/1000 |
| Rabbit anti-pMEK (S217/221) (41G9 monoclonal | Cell Signaling Tech. | 9154 | 1/1000 |
| Mouse MoAb anti-GAPDH (6C5) | CalBiochem. | CB1001 | 2.5 ug/ml |

Upon completion of the primary antibody incubation, the blots were washed three times for 10 min in TTBS and then incubated with 1/25,000 dilutions of peroxidase-conjugated donkey anti-mouse IgG (Jackson ImmunoResearch #715-035-150) or peroxidase-conjugated donkey anti-rabbit IgG (Jackson ImmunoResearch #711-035-152) in TTBS containing 3% BSA for one hour at room temperature. After washing, stained bands were visualized by incubation with ECL-plus substrate (GE) and exposure to Hyperfilm high performance chemiluminescence film (GE). The films of the blots were digitally photographed and processed identically by rendering into gray scale images and auto-adjusting the color level using the GIMP software.

Densitometry.

The integrated densities (id) of the bands of interest were measured using Image J software (NIH). The id of the anti-FAK and anti-MEK stained bands of each RIPA lysate were normalized to the id obtained for the mouse-anti-GAPDH signal of the lysate. For each lysate, the ids obtained for the anti-pFAK- and anti-pMEK stained bands were normalized to the id of the anti-FAK and anti-MEK stained bands, respectively.

Figure 19:
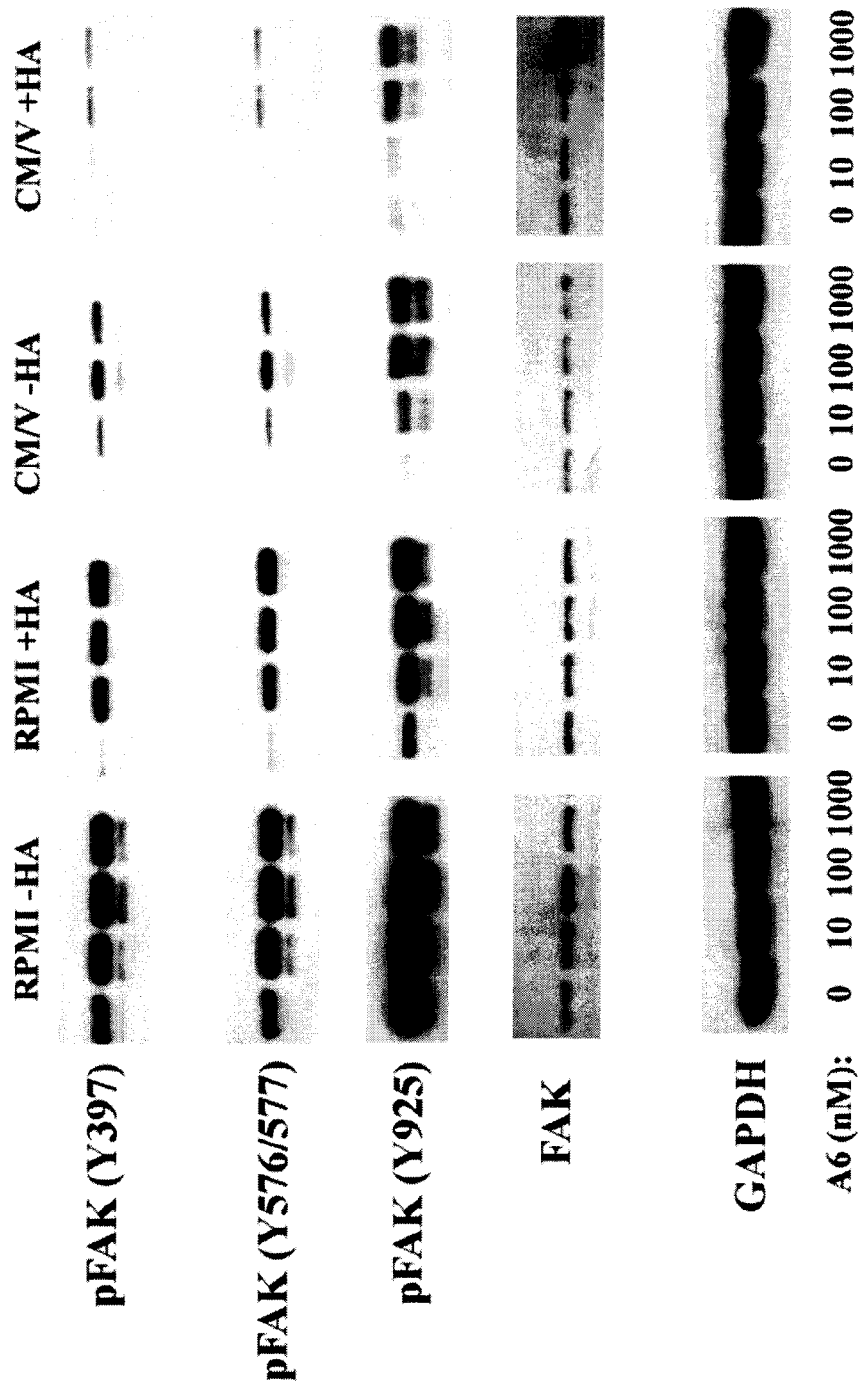
FIG. 19 shows FAK and pFAK expression in SKOV3 cells, with and without pre-treatment with HA and with and without the Å6 peptide.

Referring now to FIG. 19, SKOV3 cells were detached from their culture vessel, washed and re-suspended in RPMI containing 0.5% BSA (RPMI/BSA) or in the conditioned media of growing NIH3T3 fibroblasts supplemented with 10 ng/ml VEGF. Soluble hyaluronic acid (HA) was added at 0 and 100 ug/ml (− and +, respectively) and the cells incubated for 30 min at 37° C. The cells were then plated into culture dishes, 0 or 100 nM Å6 added (− and +, respectively) and cultured overnight. Lysates were generated and subjected to immunoblot analyses with antibodies specific for GAPDH, FAK and determinants generated when FAK is phosphorylated on tyrosine residues 397, 576/577 and 925. As shown in FIG. 19, Å6 enhanced pFAK/FAK ratios in a dose-dependent manner under all conditions while HA reduced pFAK/FAK. All pFAK sites are affected by Å6 and HA, which indicates antagonistic effects upstream to FAK activation or antagonistic effects on phosphatase activity that regulates FAK phosphorylation.

Figure 20:
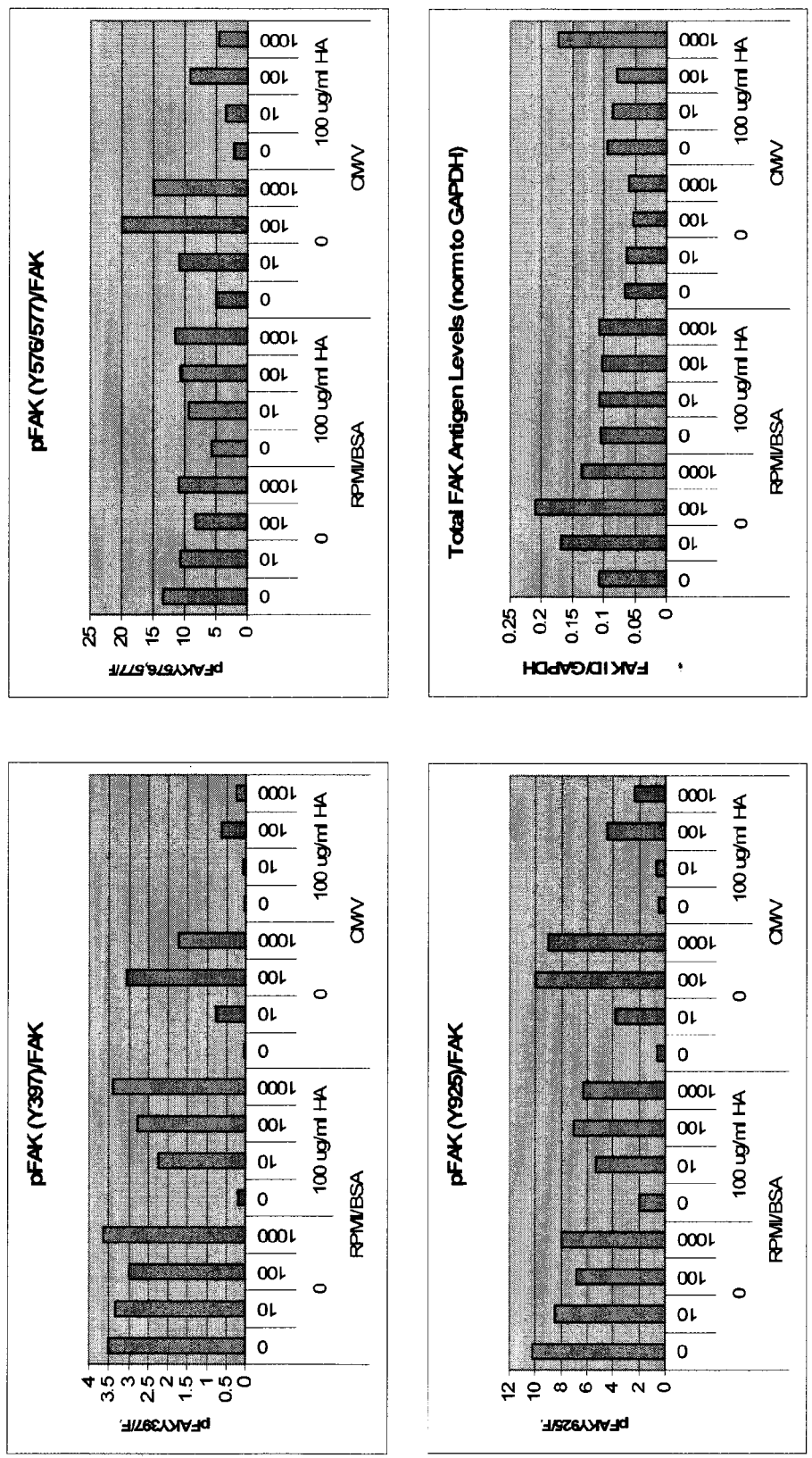
FIG. 20 shows densitometric analysis of pFAK and FAK in SKOV3 cells with and without pre-treatment with HA in the presence of the Å6 peptide.

Referring now to FIG. 20, for each lysate analyzed, the integrated densities (id) of the anti-pFAK stained bands of the immunoblots were obtained using NIH Image J software and normalized to the id of the anti-FAK stained band obtained. The id of the anti-FAK stained band of each lysate stained was normalized to the id obtained for the anti-GAPDH stained band.

As shown in FIG. 20, in RMPI/BSA Å6 restored FAK phosphorylation in the presence of HA. In CM/V media, Å6 also enhanced FAK phosphorylation. Without being bound by theory, it has been indicated that the increase in FAK phosphorylation can be the result of FAK inhibition causing upregulation of its phosphorylation. This effect was more evident in the absence of HA. Focal adhesions are found at the cell membrane where the cytoskeleton interacts with proteins of the extracellular matrix. Å6 can desensitize the cell, dissociating focal adhesions, leading to an induction of FAK to overcome the observed decrease. The clustering of integrins at focal adhesions results in the recruitment of numerous proteins that initiate intracellular regulatory processes including, for example, cell migration and anchorage-dependent differentiation. Focal adhesion kinase (FAK) is a protein tyrosine kinase which is recruited at an early stage to focal adhesions and mediates many downstream responses. The kinase activity of FAK is activated by the Src non-receptor tyrosine kinase, which is recruited at an SH2 binding site generated on FAK by autophosphorylation. FAK subsequently interacts with a number of down-stream signaling proteins, including the adaptor protein Grb2 and the p85-subunit of phosphatidylinositol 3 kinase (PI3 kinase).

Figure 21:
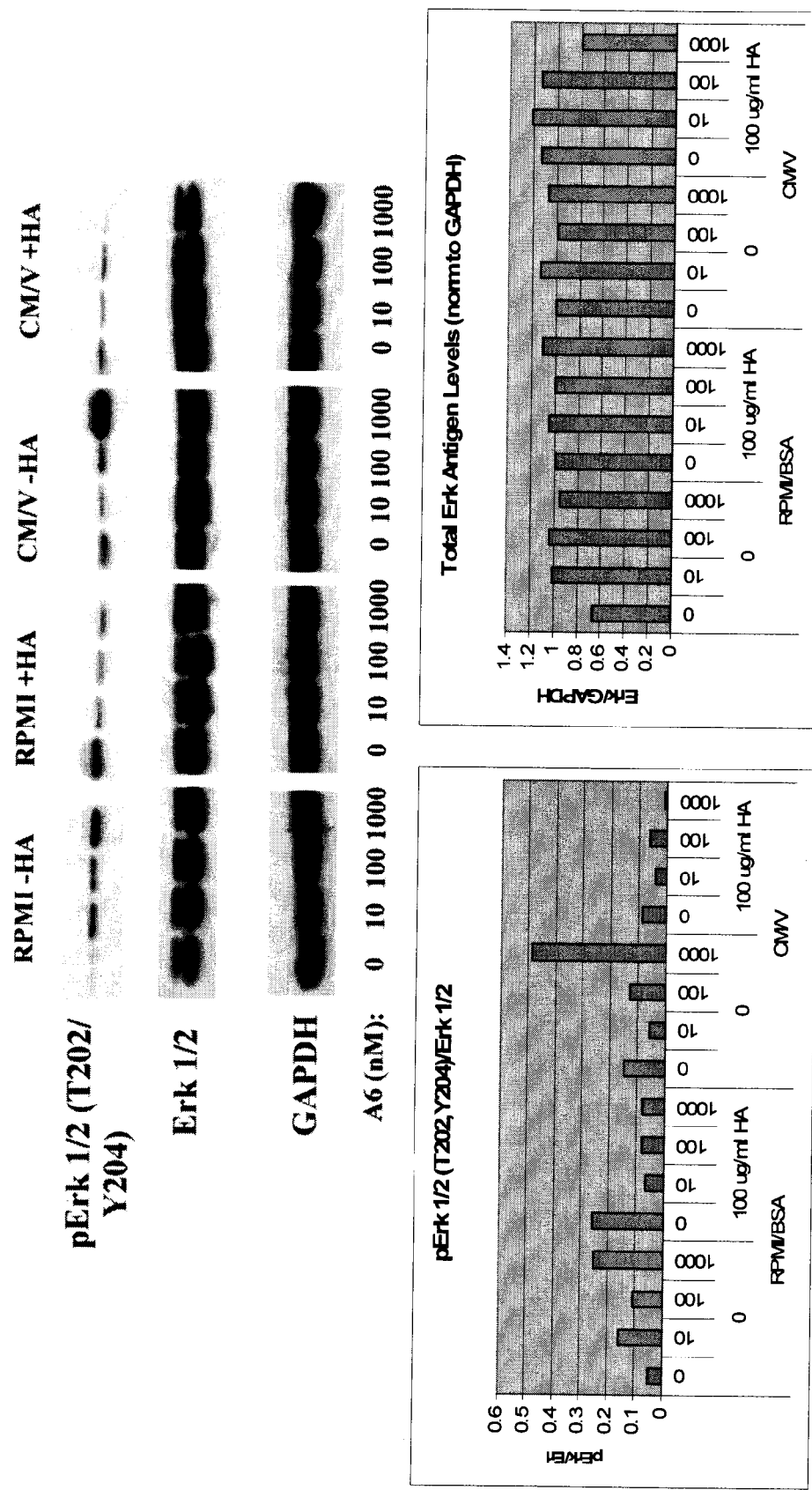
FIG. 21 shows ERK 1/2 and pERK 1/2 (T202/Y204) expression in SKOV3 cells, with and without pre-treatment with HA and with and without the Å6 peptide.

As shown in FIG. 21, Å6 increased pERK/Erk in a dose dependent manner in basal media (RPMI/BSA), while HA increased pErk/Erk. Å6 decreased this response to HA.

CM/V increased pErk/Erk as compared to basal media. Å6 appears to have increased pErk/Erk in CM/V, while Å6 decreased pERK/Erk in CM/V with HA present.

Figure 22:
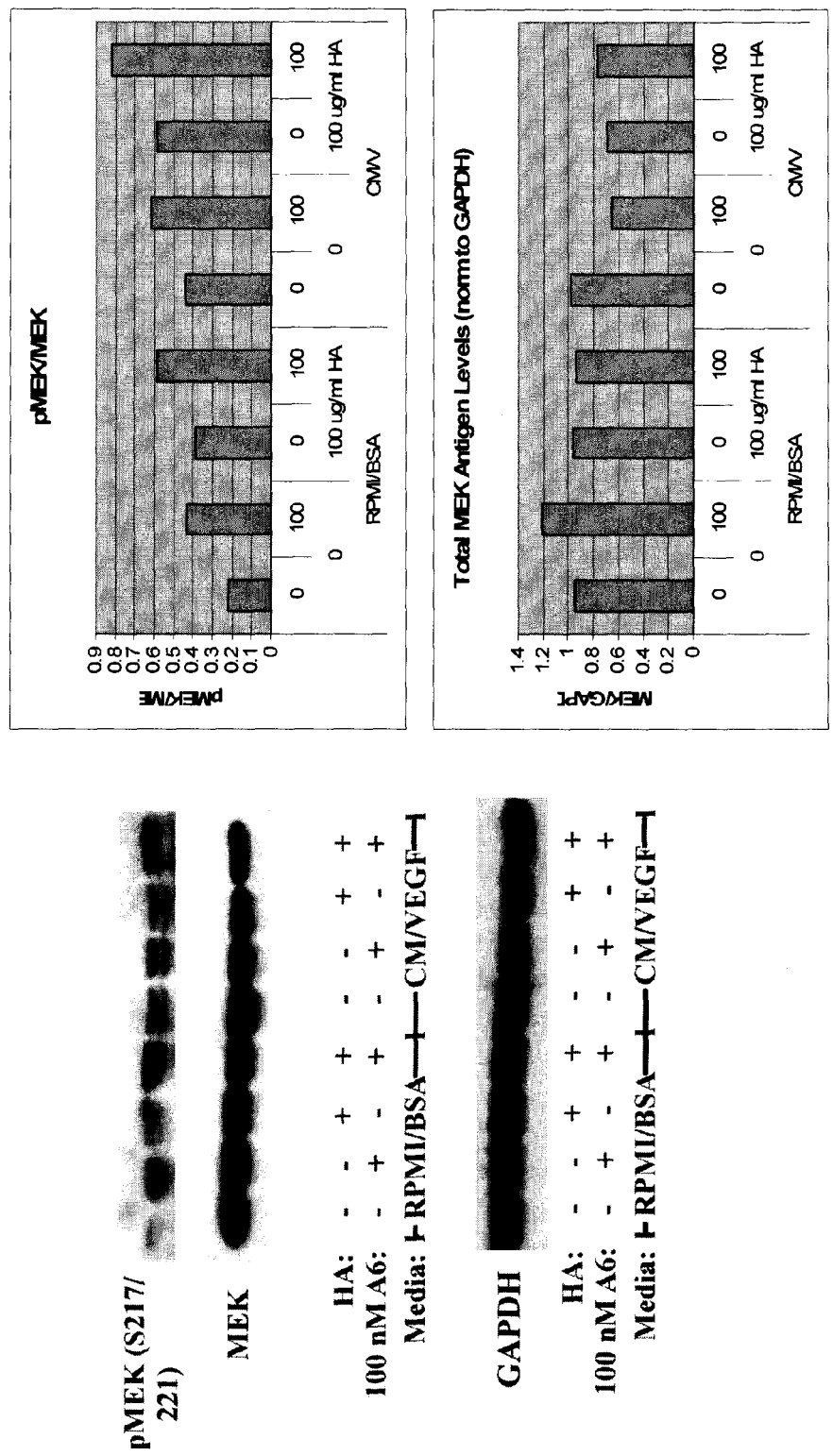
FIG. 22 shows MEK and pMEK (S217/221) expression in SKOV3 Cells, with and without pre-treatment with HA and with and without the Å6 peptide.

Referring now to FIG. 22, SKOV3 cells were detached from their culture vessel, washed and re-suspended in RPMI containing 0.5% BSA (RPMI/BSA) or in the conditioned media of growing NIH3T3 fibroblasts supplemented with 10 ng/ml VEGF. Soluble hyaluronic acid (HA) was added at 0 and 100 ug/ml (− and +, respectively) and the cells incubated for 30 min at 37° C. The cells were then plated into culture dishes, 0 or 100 nM Å6 added (− and +, respectively) and cultured overnight. Lysates were generated and subjected to immunoblot analyses with antibodies specific for GAPDH, MEK and determinants generated when MEK is phosphorylated on serine residues 217 and 221. For each lysate analyzed the integrated densities (id) of the anti-pMEK stained bands of the immunoblots were obtained using NIH Image J software and normalized to the id of the anti-MEK stained band obtained. The id of the anti-MEK stained band of each lysate stained was normalized to the id obtained for the anti-GAPDH stained band. As shown in FIG. 22, Å6 enhanced pMEK/MEK under all conditions, while HA increased pMEK/MEK under all conditions. CM/V increased pMEK/MEK ratios and Å6 potentiated this response. HA appears to have decreased total MEK levels, while CM/V appears to have potentiated this response.

Figure 23:
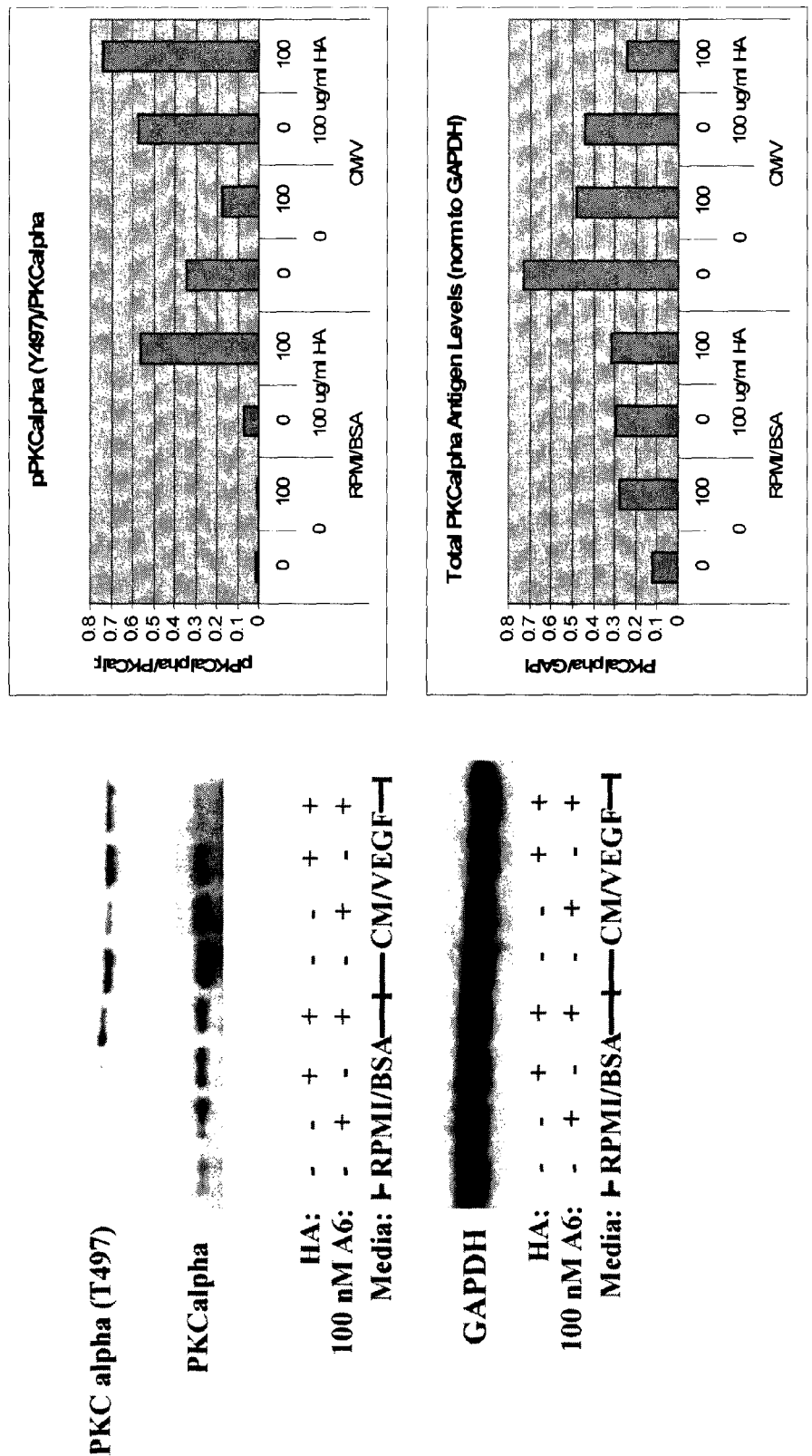
FIG. 23 shows PKCalpha and pPKCalpha expression in SKOV3 cells, with and without pre-treatment with HA and with and without the Å6 peptide.

As shown in FIG. 23, HA appears to have enhanced pPCKa/PKCa, opposite to what was observed for FAK. Å6 appears to have further enhanced pPKCa/PKCa in the presence of HA. Å6 decreased pPKCa/PKCa in CM/V in the absence of HA. Although variable total PKCalpha levels were observed, Å6 decreased total PKCalpha in the CM/V cultured samples.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A method of treating a disease characterized by aberrant cell migration and/or invasion comprising administering to a subject an effective amount of an isolated peptide to modulate a FAK signal transduction pathway, thereby treating the disease, wherein said peptide comprises no more than 20 amino acid residues in length and an amino acid sequence comprising SEQ ID NO:3, wherein said disease is selected from the group consisting of ovarian cancer, lung cancer, breast cancer, prostate cancer and melanoma.

2. The method of claim 1, wherein the FAK signal transduction pathway is modulated by altering the phosphorylation of FAK.

3. The method of claim 1, wherein said peptide comprises no more than 15 amino acid residues in length.

4. The method of claim 1, wherein said peptide comprises no more than 14 amino acid residues in length.

5. The method of claim 1, wherein said peptide comprises no more than 13 amino acid residues in length.

6. The method of claim 1, wherein said peptide comprises no more than 12 amino acid residues in length.

7. The method of claim 1, wherein said peptide comprises no more than 11 amino acid residues in length.

8. The method of claim 1, wherein said peptide comprises no more than 10 amino acid residues in length.

9. The method of claim 1, wherein said peptide comprises no more than 9 amino acid residues in length.

10. The method of claim 1, wherein said peptide consists of the amino acid sequence of SEQ ID NO:3.

11. The method of claim 1, wherein said peptide is capped.

12. The method of claim 11, wherein said capped peptide consists the sequence Am-NASAPPEE-Ac (SEQ ID NO:4).

13. The method of claim 1, wherein said disease comprises cell metastasis, invasion or growth of metastases or tumor formation.

14. The method of claim 13, wherein said ovarian cancer, lung cancer, breast cancer or prostate cancer comprises a carcinoma a sarcoma.

15. The method of claim 1, wherein said disease comprises cell metastasis.

16. The method of claim 15, wherein said cell metastasis is metastasis of a neoplastic cell or cancerous cell.

17. The method of claim 1, wherein said disease comprises invasion or growth of metastases.

18. The method of claim of claim 1, wherein said disease is ovarian cancer.

19. The method of claim of claim 1, wherein said disease is lung cancer.

20. The method of claim of claim 1, wherein said disease is breast cancer.

21. The method of claim of claim 1, wherein said disease is prostate cancer.

22. The method of claim of claim 1, wherein said disease is melanoma.

* * * * *

SEQUENCE LISTING

```
<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: peptide which potentiates the binding of CD44
      polypeptide expressing cells to hyaluronic acid (HA)
<220> FEATURE:
<221> NAME/KEY: ACETYLATION
<222> LOCATION: 1
<223> OTHER INFORMATION: Xaa = acetyl(Ac)-Lys
<220> FEATURE:
<221> NAME/KEY: AMIDATION
<222> LOCATION: 8
<223> OTHER INFORMATION: Xaa = amido(Am)-Glu

<400> SEQUENCE: 1

Xaa Pro Ser Ser Pro Pro Glu Xaa
1               5

<210> SEQ ID NO 2
<211> LENGTH: 8
<212> TYPE: PRT
<213> ORGANISM: Artificial Sequence
<220> FEATURE:
<223> OTHER INFORMATION: peptide which potentiates the binding of CD44
      polypeptide expressing cells to hyaluronic acid (HA)

<400> SEQUENCE: 2

Lys Pro Ser Ser Pro Pro Glu Glu
1               5

<210> SEQ ID NO 3
<211> LENGTH: 8
<212> TYPE: PRT
<213> ORGANISM: Artificial Sequence
<220> FEATURE:
<223> OTHER INFORMATION: peptide which potentiates the binding of CD44
      polypeptide expressing cells to hyaluronic acid (HA)

<400> SEQUENCE: 3
```

```
Asn Ala Ser Ala Pro Pro Glu Glu
1               5

<210> SEQ ID NO 4
<211> LENGTH: 8
<212> TYPE: PRT
<213> ORGANISM: Artificial Sequence
<220> FEATURE:
<223> OTHER INFORMATION: peptide which potentiates the binding of CD44
      polypeptide expressing cells to hyaluronic acid (HA)
<220> FEATURE:
<221> NAME/KEY: ACETYLATION
<222> LOCATION: 1
<223> OTHER INFORMATION: Xaa = Acetyl(Ac)-Asn
<220> FEATURE:
<221> NAME/KEY: AMIDATION
<222> LOCATION: 8
<223> OTHER INFORMATION: Xaa = amido (Am)-Glu

<400> SEQUENCE: 4

Xaa Ala Ser Ala Pro Pro Glu Xaa
1               5

<210> SEQ ID NO 5
<211> LENGTH: 159
<212> TYPE: PRT
<213> ORGANISM: Artificial Sequence
<220> FEATURE:
<223> OTHER INFORMATION: CD44 HA binding domain
<220> FEATURE:
<221> NAME/KEY: DOMAIN
<222> LOCATION: (13)...(108)
<223> OTHER INFORMATION: CD44 Link module

<400> SEQUENCE: 5

Ala Gln Ile Asp Leu Asn Ile Thr Cys Arg Phe Ala Gly Val Phe His
1               5                   10                  15

Val Glu Lys Asn Gly Arg Tyr Ser Ile Ser Arg Thr Glu Ala Ala Asp
            20                  25                  30

Leu Cys Lys Ala Phe Asn Ser Thr Leu Pro Thr Met Ala Gln Met Glu
        35                  40                  45

Lys Ala Leu Ser Ile Gly Phe Glu Thr Cys Arg Tyr Gly Phe Ile Glu
    50                  55                  60

Gly His Val Val Ile Pro Arg Ile His Pro Asn Ser Ile Cys Ala Ala
65                  70                  75                  80

Asn Asn Thr Gly Val Tyr Ile Leu Thr Ser Asn Thr Ser Gln Tyr Asp
                85                  90                  95

Thr Tyr Cys Phe Asn Ala Ser Ala Pro Pro Glu Glu Asp Cys Thr Ser
            100                 105                 110

Val Thr Asp Leu Pro Asn Ala Phe Asp Gly Pro Ile Thr Ile Thr Ile
        115                 120                 125

Val Asn Arg Asp Gly Thr Arg Tyr Val Gln Lys Gly Glu Tyr Arg Thr
    130                 135                 140

Asn Pro Glu Asp Ile Tyr Pro Ser Asn Pro Thr Asp Asp Val
145                 150                 155
```